US010487819B2

(12) United States Patent
Gould et al.

(10) Patent No.: US 10,487,819 B2
(45) Date of Patent: Nov. 26, 2019

(54) PERISTALTIC MICROPUMP AND RELATED SYSTEMS AND METHODS

(71) Applicant: VANDERBILT UNIVERSITY, Nashville, TN (US)

(72) Inventors: Parker A. Gould, Cambridge, MA (US); Loi T. Hoang, Antioch, TN (US); Joseph R. Scherrer, Nashville, TN (US); William J. Matloff, Paradise Valley, AZ (US); Kevin T. Seale, Nashville, TN (US); Erica L. Curtis, Atlanta, GA (US); David K. Schaffer, Nashville, TN (US); Douglas J. Hall, Chesterfield, MO (US); Ayeeshik Kole, Columbia, MD (US); Ronald S. Reiserer, Nashville, TN (US); Hunter Tidwell, Nashville, TN (US); Philip C. Samson, Nashville, TN (US); John P. Wikswo, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/820,506

(22) Filed: Nov. 22, 2017

(65) Prior Publication Data

US 2018/0209552 A1 Jul. 26, 2018

Related U.S. Application Data

(62) Division of application No. 13/877,925, filed as application No. PCT/US2011/055432 on Oct. 7, 2011, now abandoned.

(Continued)

(51) Int. Cl.
- *F04B 43/12* (2006.01)
- *F04B 43/00* (2006.01)
- *B01L 3/00* (2006.01)

(52) U.S. Cl.
CPC ...... *F04B 43/1269* (2013.01); *F04B 43/0054* (2013.01); *F04B 43/0072* (2013.01);
(Continued)

(58) Field of Classification Search
CPC .............. F04B 43/1253; F04B 43/1269; F04B 43/0054; F04B 43/0072
See application file for complete search history.

(56) References Cited

U.S. PATENT DOCUMENTS

| | | | | |
|---|---|---|---|---|
| 2,920,578 A | * | 1/1960 | Schaurte | ................. F04B 43/14 417/477.7 |
| 5,813,842 A | * | 9/1998 | Tamari | ................ A61M 1/3621 417/477.1 |
| 2009/0053085 A1 | * | 2/2009 | Thompson | .......... A61M 5/1413 417/477.2 |

* cited by examiner

*Primary Examiner* — Peter J Bertheaud
(74) *Attorney, Agent, or Firm* — Locke Lord LLP; Tim Tingkang Xia, Esq.

(57) ABSTRACT

A peristaltic micropump includes one or more flexible channels configured to transfer one or more pumped fluids, and an actuator configured to engage the one or more flexible channels and rotate about a central axis. The actuator includes a plurality of rolling elements and a driving element configured such that the driving element operably rotates about the central axis and each rolling element operably rolls about a respective axis that is not parallel to the central axis. The plurality of rolling elements is disposed between the one or more flexible channels and the driving element. The driving element includes a cage configured to capture the plurality of rolling elements such that the plurality of rolling elements is located at different radii from a center of the cage.

3 Claims, 43 Drawing Sheets

Related U.S. Application Data

(60) Provisional application No. 61/390,982, filed on Oct. 7, 2010.

(52) U.S. Cl.
CPC .......... *F04B 43/12* (2013.01); *F04B 43/1253* (2013.01); *F04B 43/1292* (2013.01); *B01L 3/50273* (2013.01); *B01L 2300/0819* (2013.01); *B01L 2300/123* (2013.01)

Table 1 - Mixer Valving

| C - Closed, O - Open | Valve Number: | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Series Load | C | O | C | O | C | C | O | C | C | C | O | C | C |
| Parallel Load | C | C | C | C | C | O | O | O | O | O | O | C | C |
| Series Circulation | C | O | C | O | C | C | C | C | C | C | C | O | O |
| Parallel Circulation | O | C | O | C | O | C | C | C | C | C | C | C | C |
| Series Unload | C | O | C | O | C | C | O | C | C | C | C | C | C |
| Parallel Unload | C | C | O | C | C | O | O | C | O | C | C | C | C |

Mixing Modes:

Alternate Representation:

| X - Closed, O - Open | Valve Number: | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Series Load | X | O | X | O | X | X | O | X | X | X | O | X | X |
| Parallel Load | X | X | X | X | X | O | O | O | O | O | O | X | X |
| Series Circulation | X | O | X | O | X | X | X | X | X | X | X | O | O |
| Parallel Circulation | O | X | O | X | O | X | X | X | X | X | X | X | X |
| Series Unload | X | O | X | O | X | X | O | X | X | X | X | X | X |
| Parallel Unload | X | X | O | X | X | O | O | X | O | X | X | X | X |

Mixing Modes:

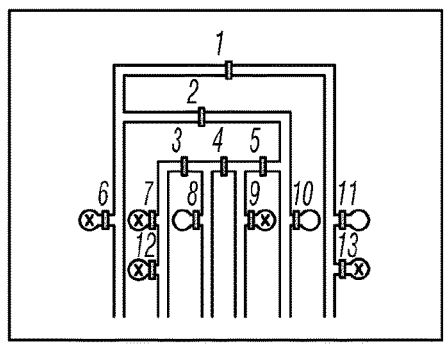

Inset: Valve Numbering

FIG. 18B

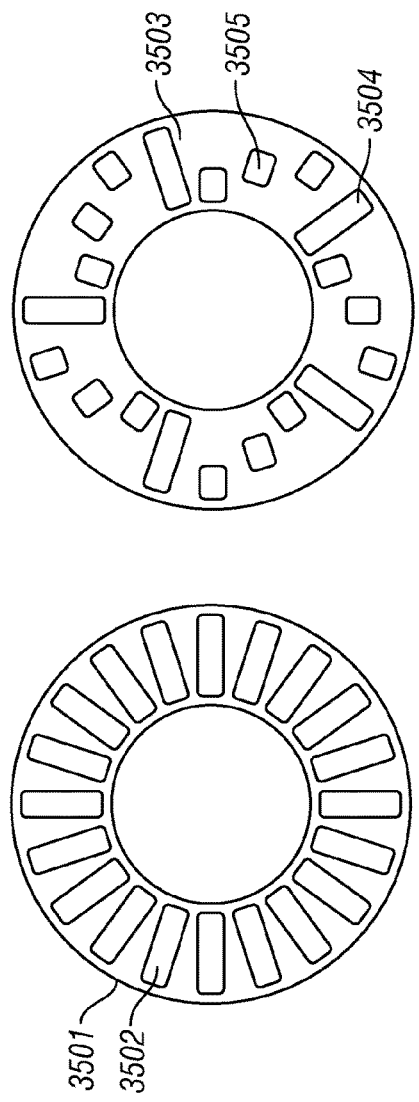
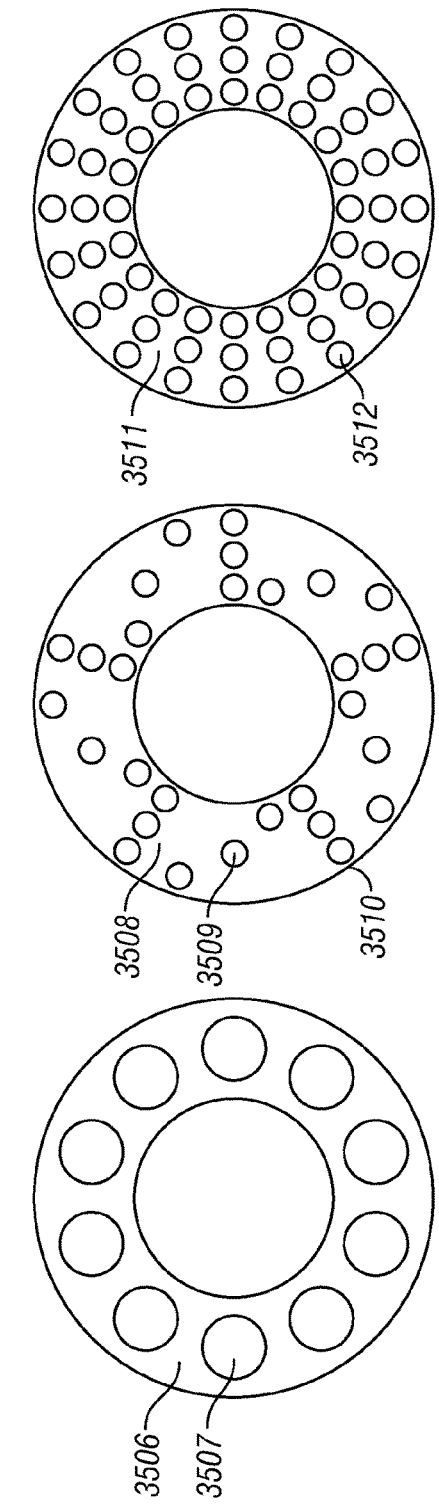
FIG. 35A
FIG. 35B
FIG. 35C
FIG. 35D
FIG. 35E

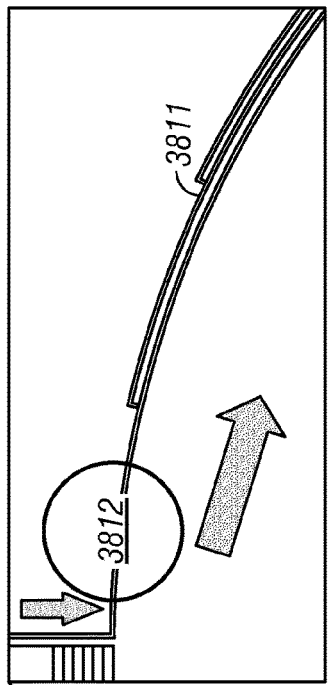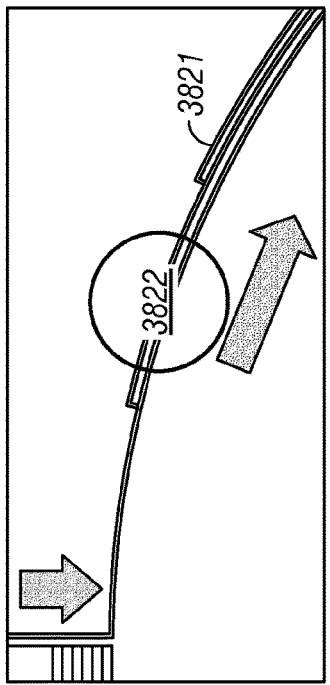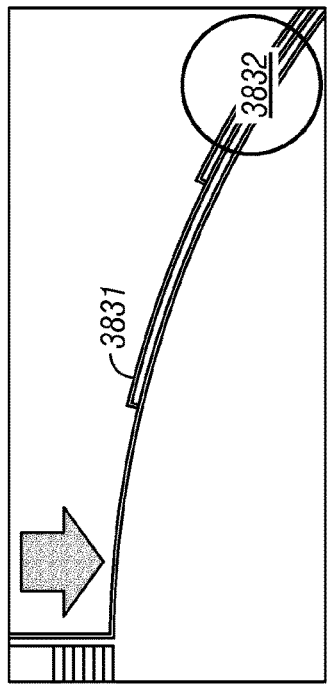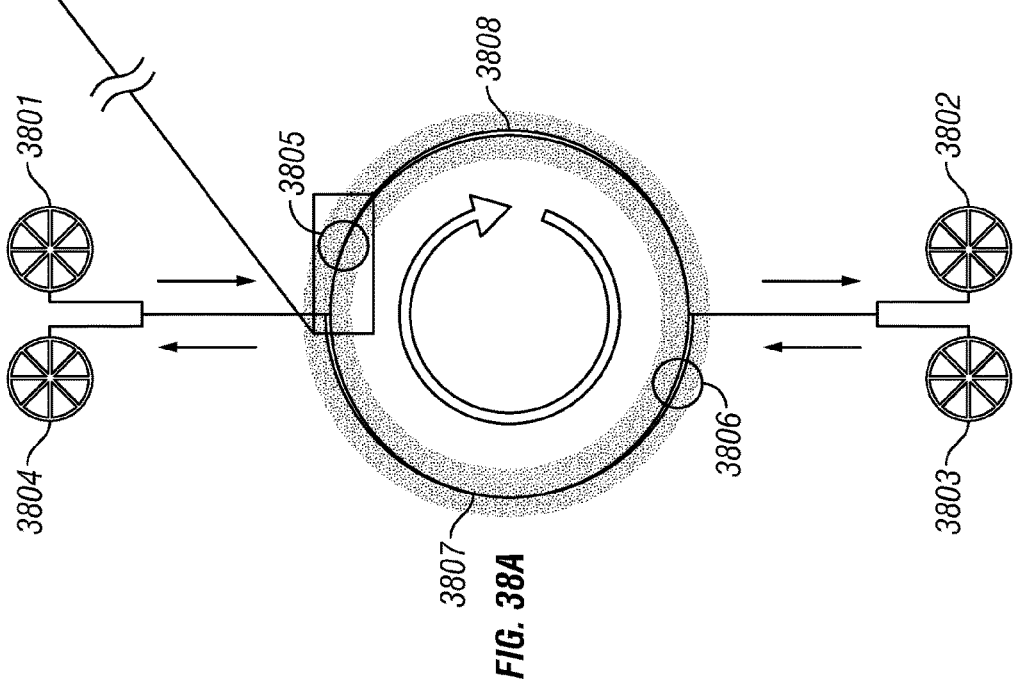

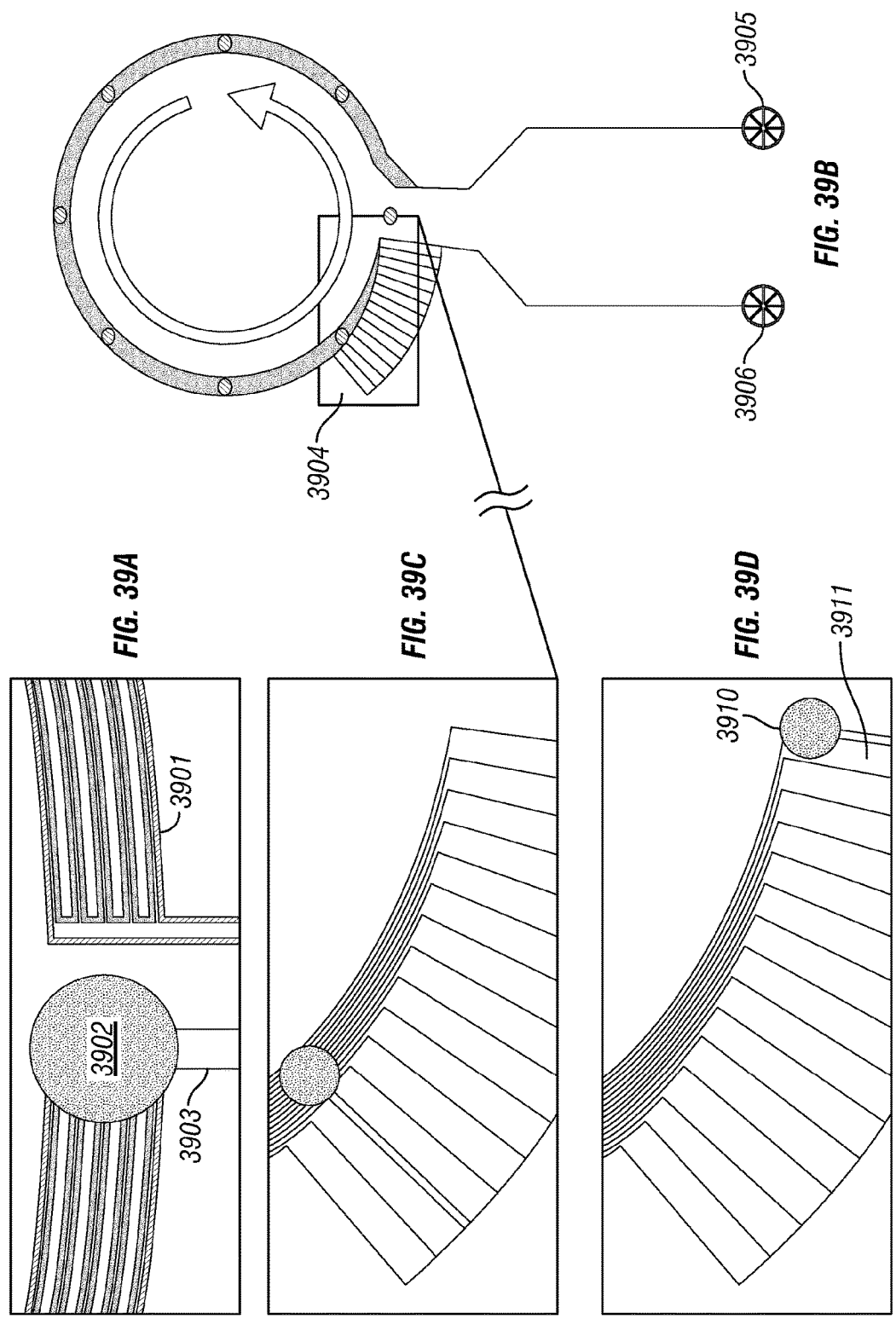

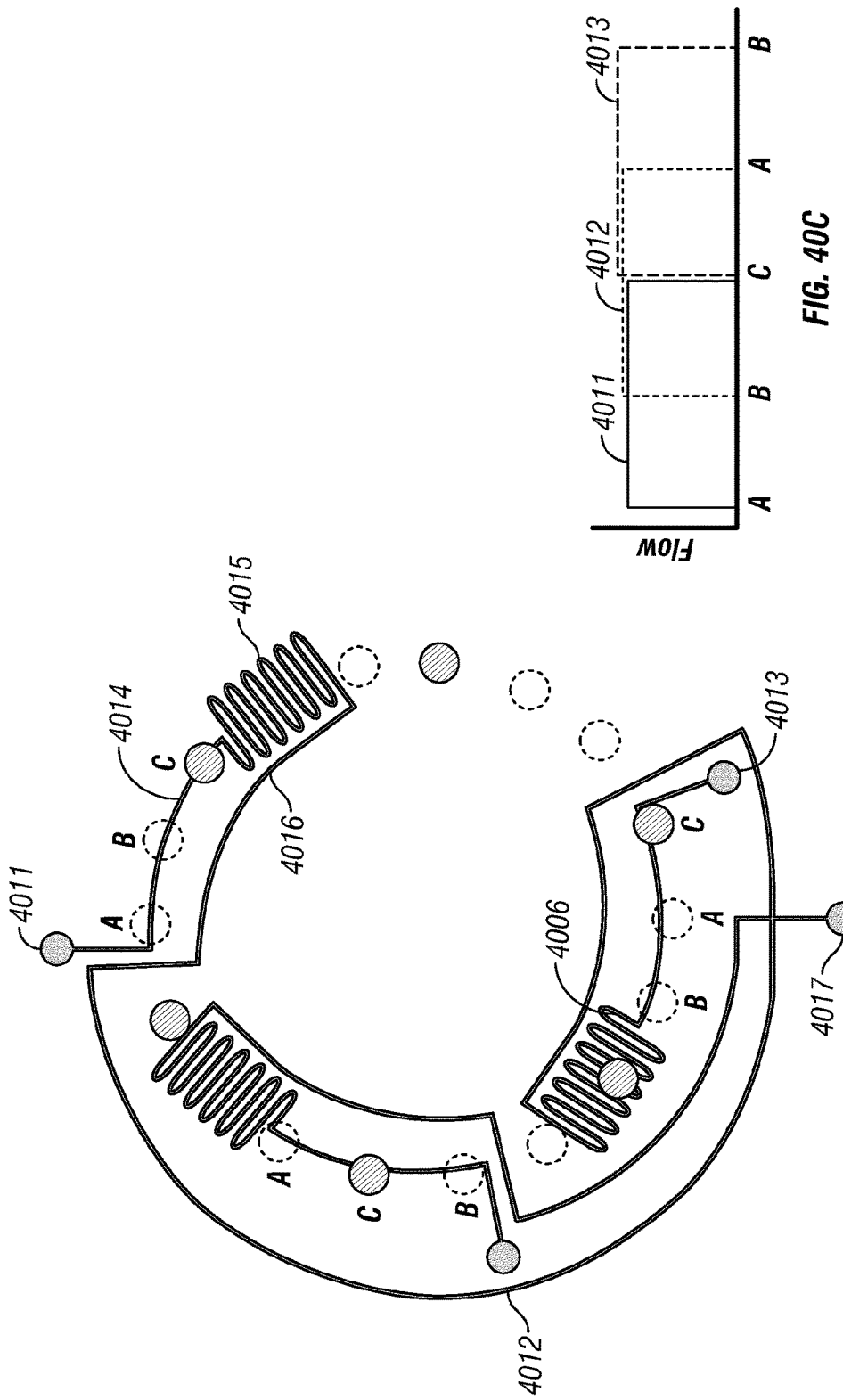

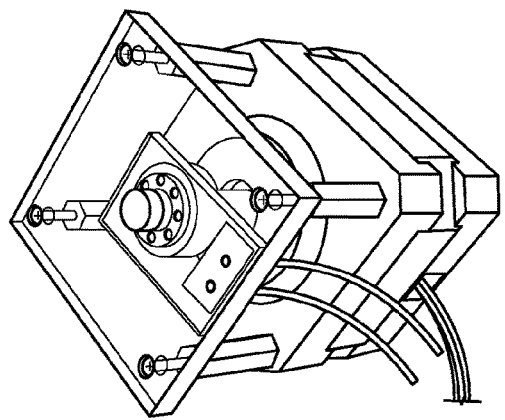
FIG. 41E
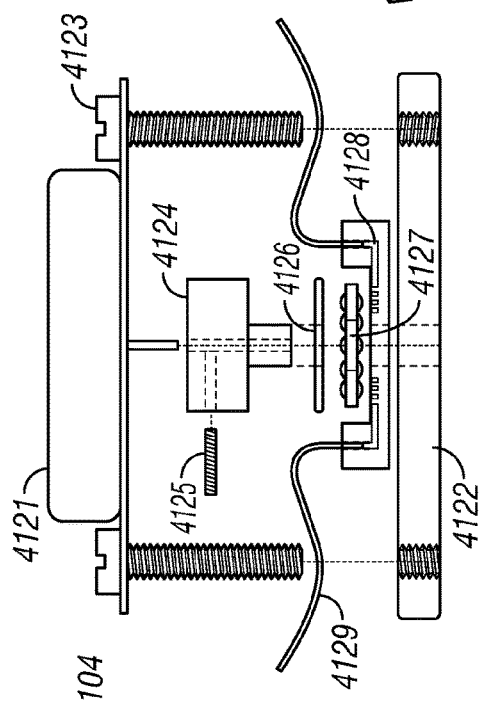
FIG. 41C
FIG. 41D
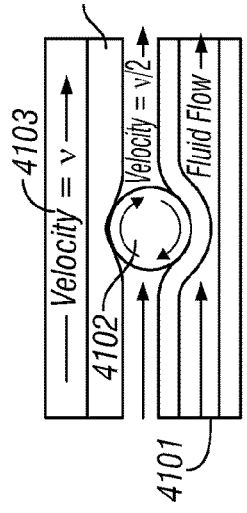
FIG. 41A
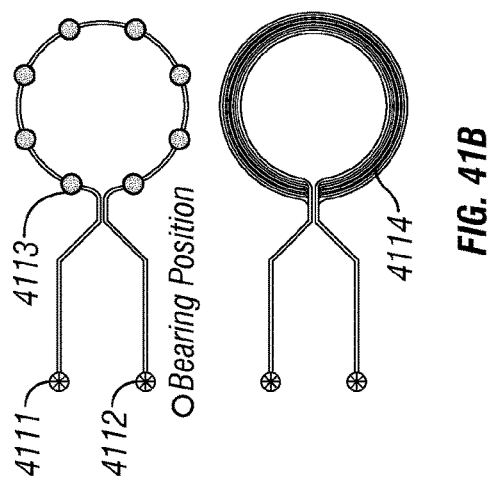
FIG. 41B

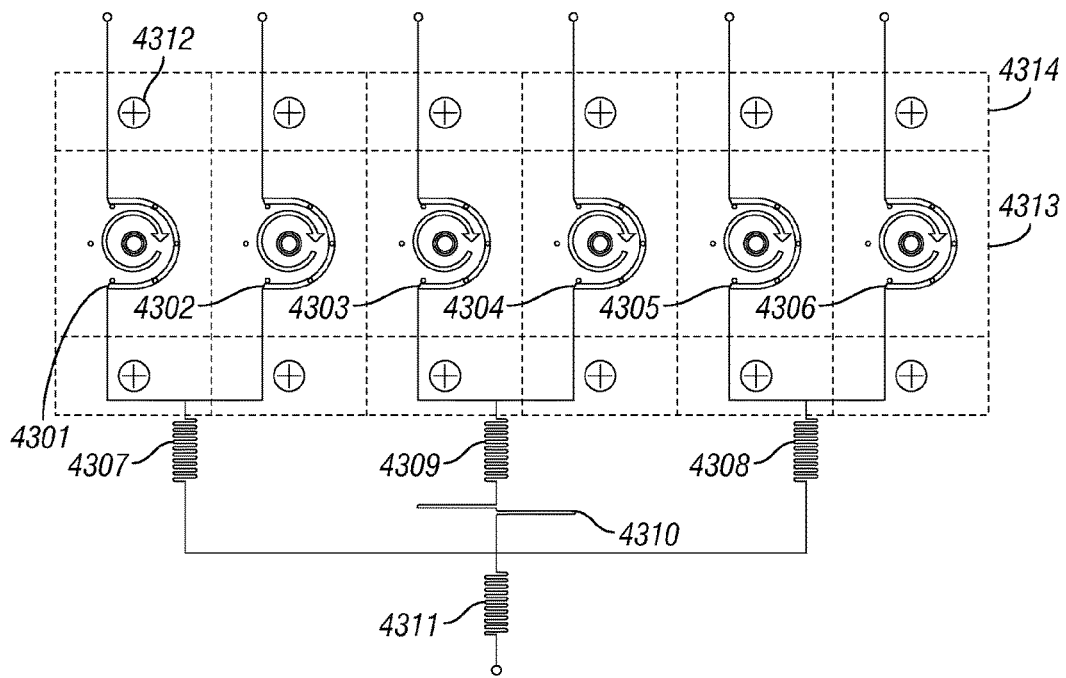
FIG. 43A
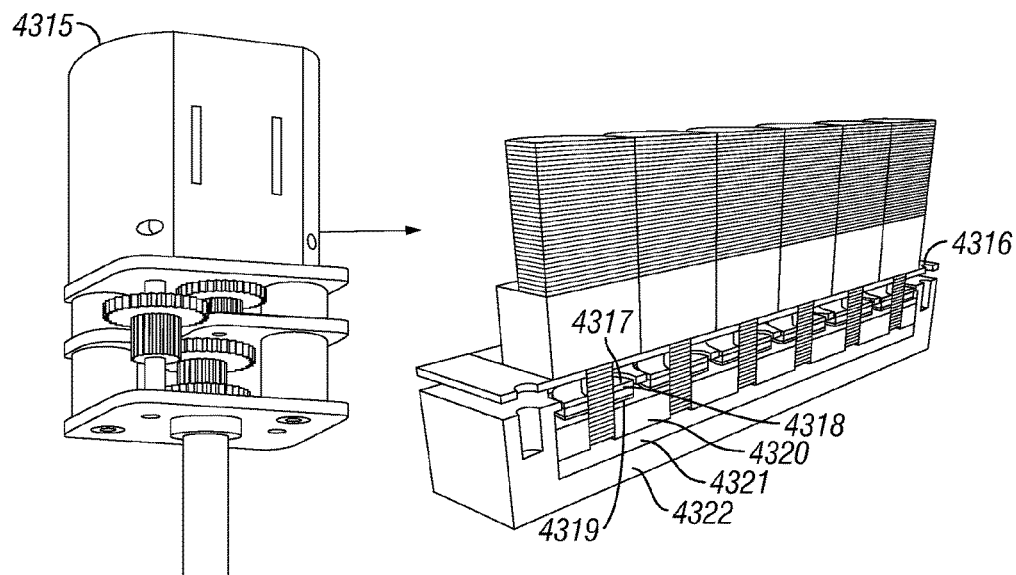
FIG. 43B
FIG. 43C

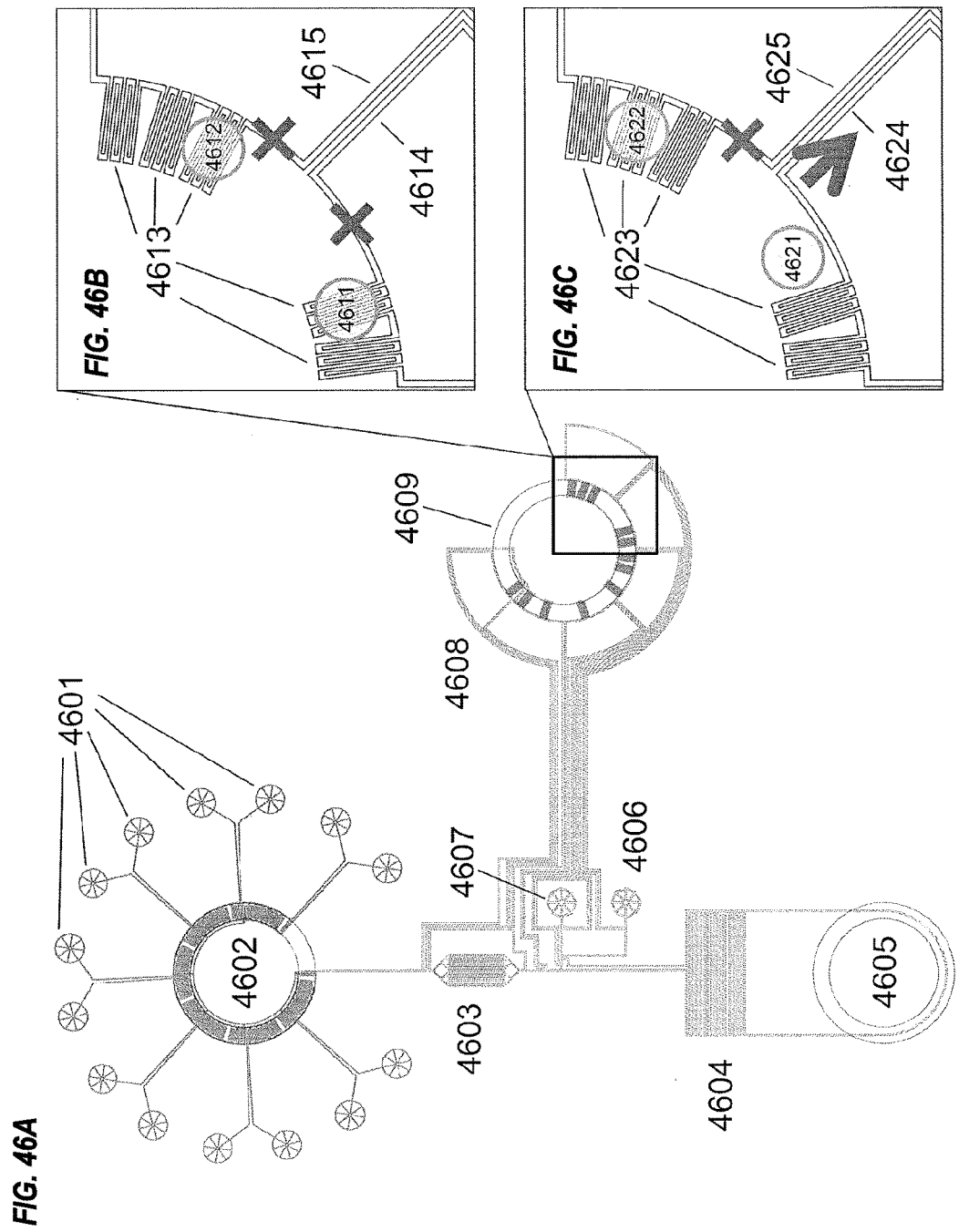

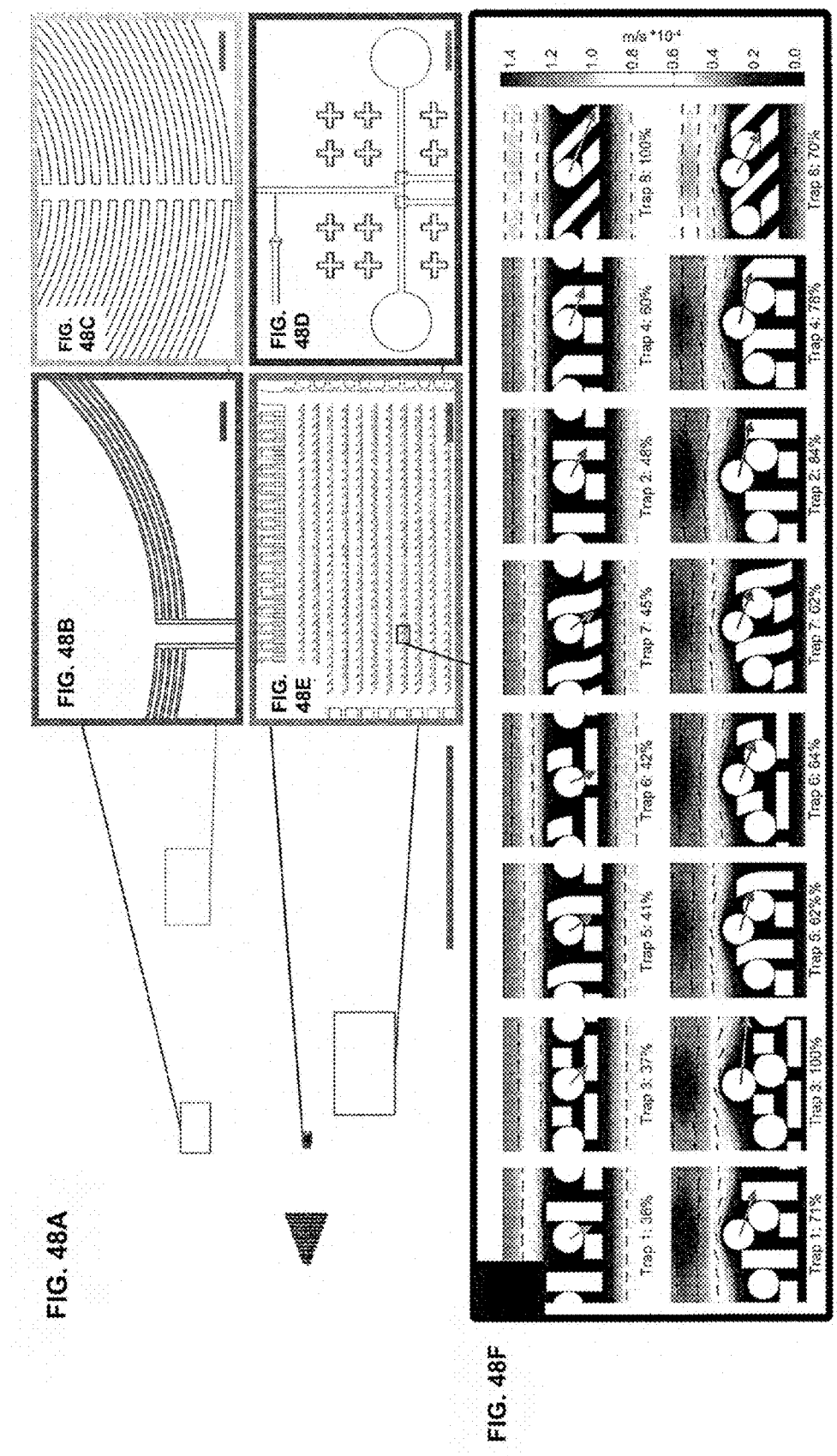

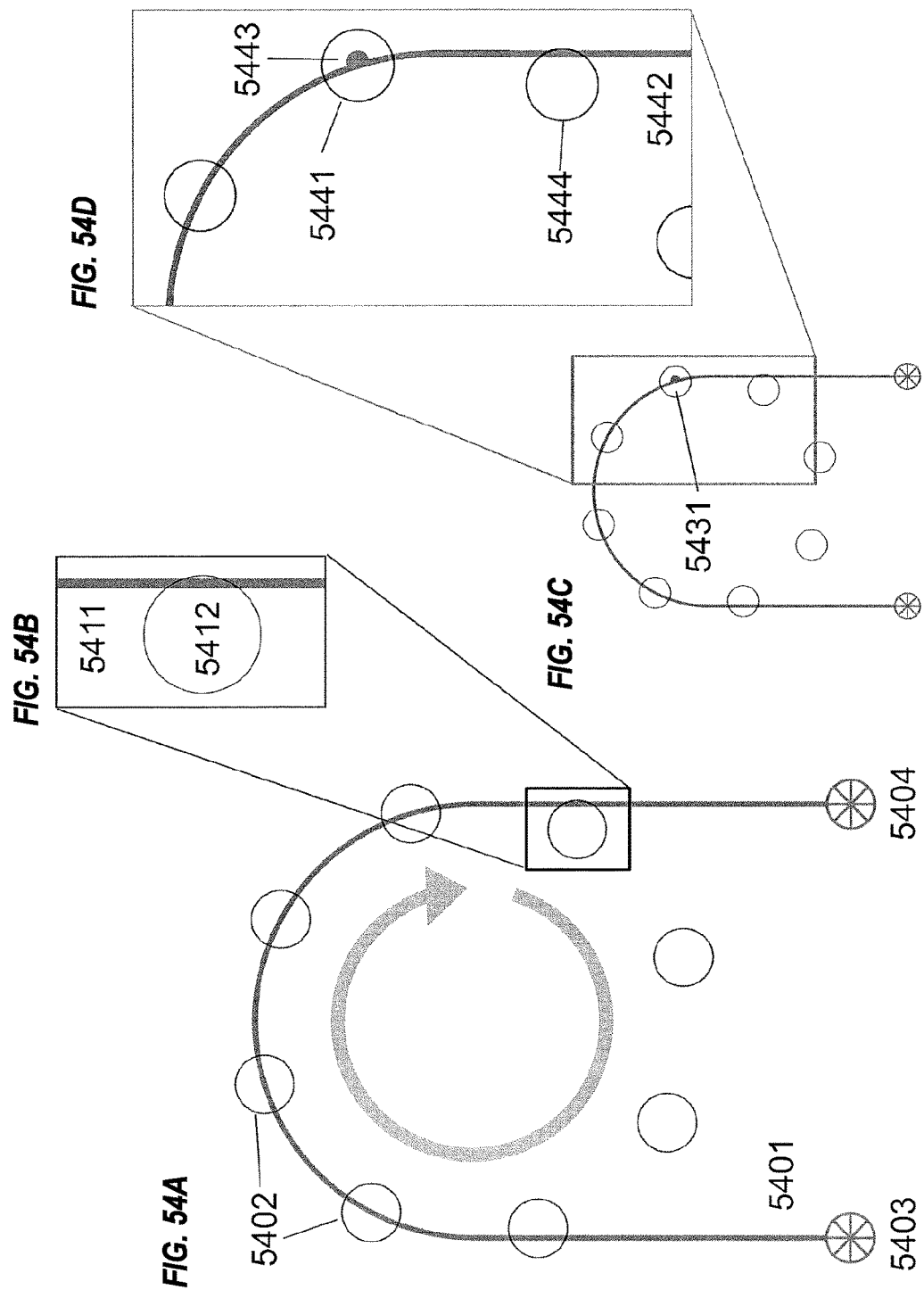

PERISTALTIC MICROPUMP AND RELATED SYSTEMS AND METHODS

CROSS-REFERENCE TO RELATED APPLICATIONS

This application is a divisional patent application of U.S. patent application Ser. No. 13/877,925, filed Jul. 16, 2013, which itself is a U.S. national phase application under 35 U.S.C. § 371 of International Patent Application No. PCT/US2011/055432, filed Oct. 7, 2011, and claims priority to U.S. Provisional Patent Application Ser. No. 61/390,982, filed Oct. 7, 2010, the entire contents of which are incorporated herein by reference.

FIELD OF THE INVENTION

The present disclosure relates generally to peristaltic micropumps and valves and related systems and methods, including microformulators, mixers, and other valved systems incorporating peristaltic micropumps.

BACKGROUND INFORMATION

Fluid flow in microfluidic devices can be driven and controlled by a variety of mechanisms, including differences in external hydrostatic pressure between inputs and outputs of a device, the use of electric forces with either dielectrophoresis or electroosmosis, actuation by pistons and/or valves, or by peristaltic action induced by a moving compressional wave induced in an elastic fluidic conduit.

Microfluidic devices for chemical or biological research offer the promise of automated complex analysis with fast reaction times and small sample consumption. For example, optimization of chemical synthesis pathways or formulation of chemical solutions on a chip is potentially very fast since many alternatives can be explored in a short time period, and only very small quantities of expensive or rare drugs or reagents are required. In addition, drug discovery experiments in which many chemical compounds and/or combinations thereof are screened by the strength of a cellular response may be conducted with greater speed and reliability. There is virtually an infinite number of potential applications of microfluidic devices since in theory any biological assay may be reduced in scale, even very complex functions that would normally be studied in vivo. For example, Harvard researchers have recently published extensive work on a lung on a chip that breathes, has its own blood circulation, and mounts its own immune response to bacterial invasion (see "Reconstituting Organ-Level Lung Functions on a Chip" Dongeun Huh, Benjamin D. Matthews, Akiko Mammoto, Martin Montoya-Zavala, Hong Yuan Hsin and Donald E. Ingber, Science, 328, 1662-1668, 2010).

However, for this type of technology (commonly referred to as "Lab on a Chip") to be integral components of real, marketable devices, it is important to be able to control and move many discrete small volumes of fluid on the chip with little dead space and without long time delays. It has been demonstrated that the exemplary embodiments of rotary planar peristaltic micropumps (RPPM) are capable of pumping a wide range of flows that are appropriate for microfluidic experiments. An RPPM can also be readily incorporated directly into a microfluidic chip, and its functionality when integrated with microfluidic networks will be enhanced by a proximal and reliable means of switching fluidic inputs upstream or fluidic outputs downstream from the pump body. An on-chip pump with switchable inputs and outputs lends flexibility to microfluidic design and allows the construction of more complex devices capable of more sophisticated sample-processing tasks.

There are many examples of microvalves in the scientific literature (see Oh et al., A Review of Microvalves, J. Micromech. Microeng., 16, R13-R39, 2006, incorporated by reference herein) that utilize a wide variety of materials and actuators. Embodiments of a rotary planar valve (RPV) described herein are a unique extension of RPPM technology. In certain embodiments, the actuator comprises a caged thrust bearing with rolling elements turned by a motor, crank or other rotational device. While similarities exist between the technologies, one difference between RPPM and RPV embodiments includes the geometry of the microfluidic channels that are compressed by the rolling elements. Unlike prior art devices, certain exemplary embodiments of the present invention utilize the concept of a rolling element being rolled in a circle over one or more channels in an elastomeric material by a rotating flange that has a matched, elastomeric driving surface.

Exemplary embodiments of the RPV described herein are small and can be located near an on-chip pump such as the RPPM. This enables the design of low volume fluidic circuits with rapid transit times, low dead volumes, and the possibility of recirculation and feedback. Although popular existing technology using pressurized, pneumatic control channels is also small-volume (see Unger, et al., Monolithic Microfabricated Valves and Pumps by Multilayer Soft Lithography, Science, 288, 113-116, 2000; and Melin, et al., Microfluidic Large-Scale Integration: The Evolution of Design Rules for Biological Automation, Annu. Rev. Biophys. Biomol. Struct., 36, 213-231, 2007, each incorporated by reference herein) exemplary embodiments of RPPM/RPV technology have an advantage of being driven by electric motors—a small, inexpensive, relatively simple, robust and mature technology, in contrast to the solenoid bank and source of pressurized gas for the pneumatic valve controller. While the pneumatic valves can be configured so that in the absence of gas pressure the valve can either be normally open or normally closed, the design determines the resting and activated conductances—these pneumatic valves cannot be toggled to remain in either state arbitrarily without the continual application of pressurized gas to maintain one of the two states.

In contrast, embodiments of a motor-driven RPPM can function as a valve when the motor is stopped. In certain embodiments, the RPV is an extension of this concept in which multiple (e.g., up to sixteen or more) separate fluidic channels or conduits are routed through the compression zone of the thrust bearing of an RPPM. In any given rotational position, the rolling element at rest compresses and occludes a predetermined number of channels, and rotation of the bearing into a set of rotational positions actuates the valve. Importantly, the fluidic channels can be oriented and sized so as to eliminate or minimize fluid displacement during actuation of the RPV. Complete elimination of displacement removes the possibility of errors in downstream chemical composition that may arise from residual volumes of displaced fluid.

One type of valve that can be created from this mechanism is an N-to-1 valve in which N input channels may be switched to connect to one output channel. Reversed, the same device connects one input to one of N outputs. This is similar in concept to a mux, demux or mux/demux combination switch in electronics (an abbreviation of multiplexers and demultiplexers). In the standard pneumatically actuated microfluidic valve, multiple solenoids are required to control multiple inputs. In this RPV embodiment, a single motor can control sixteen or more inputs. Other more specialized valve constructions that perform the microfluidic equivalent of a large number of combinations of multi-pole, multi-throw electronic switches can be built from the basic RPV platform.

In certain embodiments, RPVs can be configured wherein precise angular control of the caged bearing is provided by, for example, a stepper motor or a DC gear-head motor with an angular encoder, so that the balls or other rolling elements can be positioned exactly over a particular channel at a particular time. In some implementations, the balls would be rotated intermittently in a single direction, whereas in others, the motion would be alternately over a small angle to move a ball back and forth against a particular channel. In that latter case, a means of determining the exact position of the balls may improve the performance of the device.

In other implementations, the continuous rotation of the ball cage provides intermittent connection to multiple channels, so that the exact angle is not as important as the angular velocity. In these cases, a simple DC motor or a DC motor with gear head but no encoder would be sufficient.

One feature of exemplary embodiments of the RPPM and the RPV is that no pneumatic connection is required to control the microfluidic device. Hence this approach is particularly suited for applications wherein a disposable microfluidic cassette is inserted into, for example, a point-of-care reader, and a lever or other mechanical actuation means is provided to move the rolling elements into contact with the PDMS or other elastomeric device such that the underlying channels are compressed to allow pumping and valving operations.

This disclosure includes a variety of designs that can be implemented by various combinations of RPPMs and RPVs, or RPPMs with pneumatic valves. Several of these implementations demonstrate that the RPV and/or RPPM can be used to provide a concentration of a chemical that varies in time either in a sinusoidal manner or with some other chosen waveform, for example, to allow large-amplitude, different-frequency modulation of various chemical concentrations in a chemical reaction network to identify reactions whose rates are determined by the product of two or more concentrations. This would be difficult to achieve with conventional peristaltic pumps and on-chip microvalves.

Exemplary embodiments of the present invention include devices and methods of peristaltic pumping. In the classical, macroscopic peristaltic pump (FIG. 1), a pump body (101) constrains a deformable plastic tube (102) that is compressed by three or more rollers (103). The rollers are caused to rotate by coupling to a central rotor (104), which is caused to rotate about an axis (105). As a result, fluid is drawn into one end of the tubing (106) and expelled from the other (107). Many different techniques have been developed to simplify and streamline this method of fluidic pumping. In microfabricated devices, however, there have been only a limited number of implementations of peristaltic pumps.

In Darby et al. (2010), this system is implemented in a microfluidic device using either a rotating cam with the "tubing" wrapped around the cam, or a linear screw drive pressed against a series of microfluidic channels (FIGS. 2A and 2B). In the rotating cam version, encapsulated channels (201) are created by bonding together two thin layers (202) and (203) of a deformable polydimethylsiloxane (PDMS) polymer (one flat layer and one layer with channels). These encapsulated channels are analogous to the classic peristaltic pump's tubing, and are wrapped around a thin cylindrical mandrel and then cast in a thick PDMS layer (204) that provides mechanical support and serves as the pump body (101) in FIG. 1. After curing, a cam with an oval-shaped cross section (205), with a transverse diameter greater than that of the diameter of the original cylindrical cam, is fitted into the cylindrical hole left by the original mandrel, producing two points of compression (206 and 207). As this cam is turned (208), the two points of compression drive fluid along the channels, achieving peristaltic flow from 209 to 210. With the linear screw model, the difficult process of wrapping the channels is eliminated. The basic pumping concept is similar to the rotating cam version. A screw (211) is placed such that its major axis is parallel to the fluid channels (212), and fluid flow is then achieved by rotating the screw (213). The screw is held in place over the channels by a cast layer of PDMS (214), which also provides the requisite compression (215 and 216). As the screw rotates, the threads move along the channels, producing flow from 217 to 218.

Two other early implementations of peristaltic pumps in microfluidic devices use either an array of solenoid-actuated pins that sequentially compress zones along a microfluidic channel cast in PDMS (Gu et al., 2004, and Takayama et al., 2010) (FIG. 3), or three or more pneumatically actuated membranes that also provide sequential compression of a channel (Chou et al., 2001) (FIG. 4). In the former, a PDMS microfluidic device mounted on a rigid substrate (301) has one or more channels (302) that are compressed by pins (303-305) that are driven by solenoids, often using an apparatus found in a tactile Braille-reader head. The sequential compression of the pins draws fluid into the channels (306) and drives fluid out of the other side (307). As for the latter, the pins' functions are replaced by pneumatically actuated channels (401-403) contained in a second PDMS membrane (404) bonded to the membrane (405) containing the channels (406) to be compressed. Pressure applied to channels in the second membrane causes the channel to expand (401) and depress the membrane that forms the bottom of the upper channel, and therefore induce compression (407) along the lower channel within a microfluidic device backed by a rigid substrate (408). When adjacent channels in the upper membrane are sequentially actuated, a compression wave moves along the channels in the lower membrane and fluid is drawn from 409 to 410. In the event that pumping is not desired, both approaches require the dissipation of power to keep at least one channel closed to prevent passive flow or backflow through the pump.

Another method of inducing peristaltic compression is to drive a roller linearly across the microfluidic channel (FIG. 5). (Lim et al., 2004) When downward pressure (501) is applied to the roller (502), a point of compression is created (503), which is then made to move along a PDMS channel (504) by moving (505) the roller with a motorized actuator (506). This technique requires a large mechanical setup along with a fairly large roller. Also, the roller's path is restricted linearly, which limits possible channel geometries and eliminates the possibility of continuous or recirculating flow.

One way to create continuous flow is to use magnets and steel balls to create a circular compression zone that rotates along a circular pathway (FIG. 6). Yobas et al. (2008), and subsequently Du et al. (2009), present a peristaltic design that achieves compression (601) by magnetically attracting small steel balls (602) through a thin, channeled PDMS substrate (603) backed by a rigid poly(methyl methacrylate) layer (604). The magnets (605) are made to rotate (606) using a DC motor, which causes the balls to roll in a circular trajectory (607) along the circular PDMS channel, inducing flow from 608 to 609. However, this design has many limitations. The total number of balls that can run along a channel is limited by the minimum spacing needed to avoid adverse magnetic interactions between the individual balls and the magnet array. Rotating the balls at higher speeds (Yobas reported maximum rotation speeds of 320 RPM) introduces the problem of the magnetic field not providing the requisite centripetal force, thereby allowing the balls to disengage from the device. The amount of magnetic restoring force provided is limited by the strength of the magnet and the separation distance (device thickness) from the balls and the ball-to-ball spacing, and this force cannot be reliably scaled higher without an increase in fabrication complexity via thinner device layers or operational complexity via the introduction of electromagnets. Using permanent magnets also defines a single compression level for the channels, which must be tuned to provide enough compression for flow, but not enough that frictional forces hinder ball movement. Electromagnets would require ferromagnetic cores, would produce heat that would need to be dissipated, and would require electrical power both to operate and to prevent passive flow or backflow through the device when pumping is not desired.

SUMMARY

Exemplary embodiments include a peristaltic micropump comprising one or more conduits configured to transfer one or more pumped fluids, wherein each conduit comprises: an inlet; an outlet; and a central portion between the inlet and the outlet. Exemplary embodiments can also comprise an actuator configured to engage the central portions of the one or more conduits. In certain embodiments, the actuator is configured to rotate about a central axis, and the central portions of the one or more conduits form concentric partial rings about the central axis. In particular embodiments, the peristaltic micropump comprises at least two conduits in fluid communication with each other, while in other embodiments, none of the one or more conduits are in fluid communication with each other.

In particular embodiments, the concentric partial rings are partial circles, while in other embodiments the concentric partial rings are non-circular configurations. In specific embodiments, the actuator comprises one or more ball bearings, cylindrical rollers, or conical rollers. In certain embodiments, the central portions of the one or more conduits are arranged in a circumferential pattern so that the actuator engages the central portions as the actuator rotates. In particular embodiments, each of the one or more conduits is a different length. In certain embodiments, the ratios of the lengths of each of the one or more conduits are a non-integer fraction. In specific embodiments, the one or more conduits are configured to form an aperiodic pattern. In particular embodiments, the aperiodic pattern is a Penrose Tile design.

In certain embodiments, the actuator comprises a driving element and one or more rolling elements. In particular embodiments, the one or more rolling elements comprise one or more cylindrical rolling elements, and at least two of the cylindrical rolling elements have different lengths. In specific embodiments, the one or more rolling elements comprise one or more conical rolling elements. In particular embodiments, the driving element comprises a cage configured to capture the one or more rolling elements. In specific embodiments, the one or more rolling elements comprises one or more spherical rolling elements or cylindrical rolling elements; and the one or more rolling elements are located at substantially the same radius from the center of the cage. In particular embodiments, the one or more rolling elements comprise one or more spherical rolling elements or cylindrical rolling elements, and the one or more rolling elements are located at different radii from the center of the cage. In certain embodiments, the actuator comprises a rotating drive mechanism and a centering component configured to center the cage with respect to the rotating drive mechanism. In particular embodiments, each of the one or more rolling elements is configured to rotate about an axle.

Certain embodiments further comprise one or more valves configured to control flow of one or more pumped fluids in the one or more conduits. In specific embodiments, a first conduit of the one or more conduits comprises a bypass line configured to allow fluid to flow from the outlet of the first conduit to the inlet of the first conduit.

In particular embodiments, the one or more conduits contain at least a first fluid and a second fluid; the one or more valves can be opened and closed to control a flow rate of the first and second fluids during operation of the peristaltic micropump; and the outlets of the one or more conduits are in fluid communication such that the first and second fluids can be mixed in varying proportions. In specific embodiments, a conduit comprises an expanded area configured to reduce pulsatility. In particular embodiments, the one or more conduits are configured to reduce pulsatility. In certain embodiments, the one or more conduits are configured to provide sinusoidal or other output concentration waveforms.

Specific embodiments comprise a peristaltic microformulator comprising: a generally circumferential conduit; an actuator configured to engage the generally circumferential conduit; one or more inlets in fluid communication with the generally circumferential conduit; an outlet in fluid communication with the generally circumferential conduit, wherein the outlet comprises an outlet valve; and a bypass conduit coupling the outlet and a first inlet of the one or more inlets, wherein the bypass conduit comprises a bypass valve and the first inlet comprises an inlet valve.

In certain embodiments, the generally circumferential conduit is configured as a circle. In particular embodiments, the generally circumferential conduit is configured as a circle, triangle, square, pentagon, hexagon, heptagon, or octagon. In certain embodiments, each of the one or more inlets comprises a valve; the one or more inlets are configured to deliver at least a first fluid and a second fluid to the generally circumferential conduit; and the valves of the one or more inlets can be opened and closed to control the amount of the first and second fluid that is pumped through the outlet during operation.

Particular embodiments include a peristaltic micropump comprising: a conduit configured to transfer a pumped fluid; and an actuator configured to rotate about a central axis, wherein: the actuator comprises a rolling element and a driving element; the rolling element is disposed between the conduit and the driving element; and the driving element and the conduit have a coefficient of friction that is substantially similar. In certain embodiments, the driving element and the conduit are comprised of a flexible polymeric compound. In particular embodiments, the driving element and the conduit are comprised of polydimethylsiloxane (PDMS).

Specific embodiments include a peristaltic micropump comprising: a conduit configured to transfer a pumped fluid; and an actuator configured to rotate about a central axis, wherein: the actuator comprises a rolling element and a driving element; the rolling element is disposed between the conduit and the driving element; and the driving element and the conduit have coefficients of both elasticity and friction that are substantially similar. In particular embodiments, the driving element and the conduit are comprised of a flexible polymeric compound. In certain embodiments, the driving element and the conduit are comprised of polydimethylsiloxane (PDMS).

Specific embodiments include a peristaltic micropump comprising: a circumferential conduit; an external conduit comprising one or more valves, wherein the one or more valves are in fluid communication with the circumferential conduit; and a rotating actuator comprising one or more rolling elements configured to engage the circumferential conduit and actuate the one or more valves, wherein the one or more valves are configured to control a fluid flow in the external conduit. In certain embodiments, the circumferential conduit comprises one or more ports in fluid communication with the one or more valves, and wherein the spacing of the ports on the circumferential conduit can be used to control the fluid flow in the external conduit.

In particular embodiments, the one or more valves are normally closed, and a valve is opened when a rolling element engages a port on the circumferential conduit. In specific embodiments, during use the actuator rotates at a constant rotational speed and the fluid flow in the external conduit varies over time.

Particular embodiments include a microvalve comprising: a first conduit comprising an inlet and an outlet; an actuator configured to rotate about a central axis; and one or more rolling elements coupled to the actuator, wherein the one or more rolling elements are configured to rotate about the central axis at a first radius, wherein: a first portion of the first conduit is located at the first radius from the central axis; and a second portion of the first conduit is located at a second radius from the central axis.

In specific embodiments, the actuator comprises a driving element, the rolling element is disposed between the first conduit and the driving element, and the driving element and the first conduit have a coefficient of friction that is substantially similar. In particular embodiments, the driving element and the conduit are comprised of a flexible polymeric compound.

In certain embodiments, the actuator comprises a driving element; the rolling element is disposed between the first conduit and the driving element; and the driving element and the first conduit have a coefficient of elasticity that is substantially similar. In particular embodiments, each of the one or more rolling elements is configured to rotate about an axle. In certain embodiments, the one or more conduits are configured to provide sinusoidal or other output concentration waveforms. In certain embodiments, the one or more conduits are configured to provide droplets of a first fluid encased in a second fluid. In particular embodiments, during operation the one or more rolling elements engage the first portion of the first conduit as the rolling element rotates about the central axis. In specific embodiments, the one or more rolling elements are configured to occlude a fluid flow between the inlet and the outlet of the first conduit when the one or more rolling elements engage the first portion of the conduit. Particular embodiments comprise a second conduit extending between an inlet and an outlet, wherein a first portion of the second conduit is located at the first radius from the central axis; and a second portion of the second conduit is located at a second radius from the central axis.

In certain embodiments, the first and second conduits comprise multiple portions at the first radius from the central axis and multiple portions at the second radius from the central axis. In specific embodiments, the outlet of the first conduit and the outlet of the second conduit are in fluid communication. In particular embodiments, a rotation of the actuator controls a first fluid flow in the first conduit and a second fluid flow in the second conduit. In certain embodiments, the first conduit and the second conduit each comprise multiple portions at the first radius from the central axis. In particular embodiments, the rolling element is a ball bearing, a cylindrical roller, or a conical roller. In particular embodiments, the driving element comprises a cage configured to capture the one or more rolling elements.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 18B is a table showing one exemplary configuration of the valves for the multipath-design mixer of FIG. 18A.

FIGS. 35A-35E show schematically a variety of cage designs for custom thrust bearings, according to certain embodiments of the invention.

FIGS. 38A-38D show schematically the design and operation of a variable flow rate RPPM, according to one embodiment of the invention.

FIGS. 39A-39D illustrate schematically a pulse-regulating device, according to one embodiment of the invention.

FIGS. 40B-40C illustrate schematically an RPPM and RPV system that can act as both a fluid multiplexer and demultiplexer and the summed flow of the system, according to one embodiment of the invention.

FIG. 41A shows schematically a profile view of a peristalsis system in microfluidics, according to one embodiment of the invention.

FIG. 41B shows schematically a single-channel RPPM design and a five-channel configuration, according to certain embodiments of the invention.

FIGS. 41C-41E show schematically three views of one embodiment of an RPPM system.

FIGS. 43A-43C show schematically a design for a multipump array, according to one embodiment of the invention.

FIGS. 46A-46C illustrate schematically the design and operation of an RPPM- and RPV-driven batch mode microformulator, according to one embodiment of the invention.

FIGS. 48A-48F illustrate the steps toward implementation of the embodiment of FIG. 47.

FIGS. 54A-54D illustrate schematically an RPPM device that maintains a constant flow rate without pulsatility, according to one embodiment of the invention.

DETAILED DESCRIPTION OF EXEMPLARY EMBODIMENTS

Figure 7:
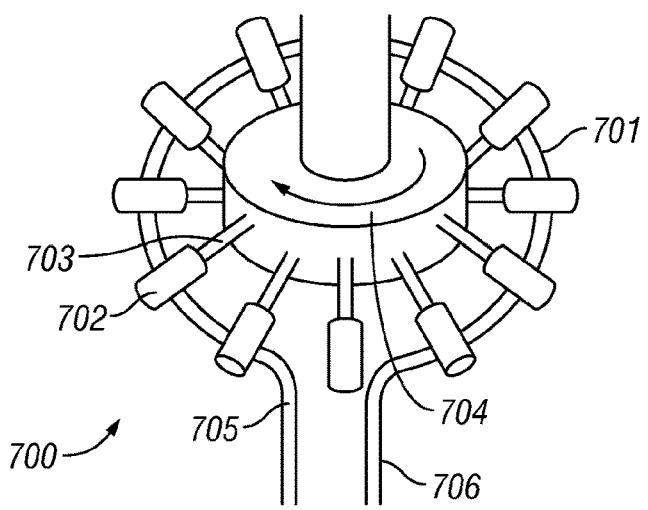
FIG. 7 shows schematically a peristaltic micropump that comprises a circumferential conduit or channel with an inlet, an outlet, and a series of rolling elements driven by a motorized hub, according to exemplary embodiments of the invention.

Referring now to FIG. 7, a peristaltic micropump 700 comprises a circumferential conduit or channel (701) with an inlet (705), an outlet (706) and a series of rolling elements (702) (e.g., roller bearings), driven by a motorized hub (704). During operation, rolling elements (702) engage and compress a circumferential channel (701) and pump a fluid from inlet (705) to outlet (706). In the power-off mode when the pump is not operating, one or more rolling elements prevent passive forward or reverse flow through the device. In certain embodiments, the circumferential channel (701) may be formed as a circle, and in other embodiments circumferential channel (701) may be formed as a polygon (e.g., a triangle, square, pentagon, hexagon, heptagon, octagon, etc.). It is understood that the circular or polygonal shape of circumferential channel (701) is used in general terms and describes the shape of circumferential channel (701) if circumferential channel (701) extended through the space between inlet (705) and outlet (706).

Figure 1:
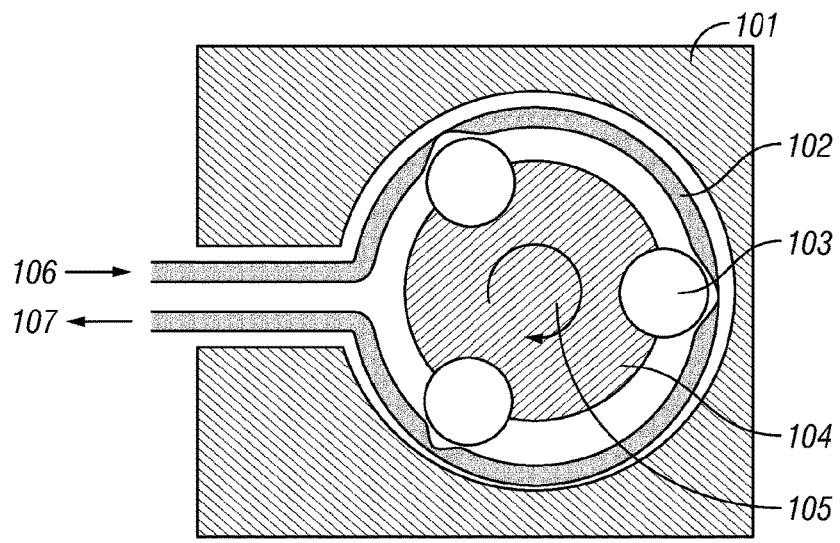
FIG. 1 shows schematically the classical, macroscopic peristaltic pump.
Figure 2A:
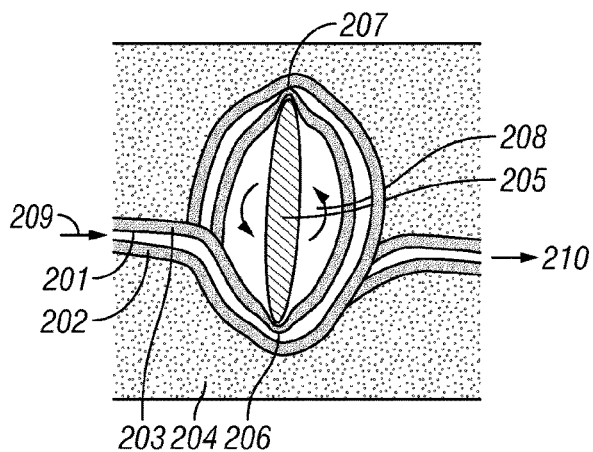
FIGS. 2A-2B show schematically two implementations of peristaltic pumping in microfluidic devices, as described in Darby et al. (2010).
Figure 2B:
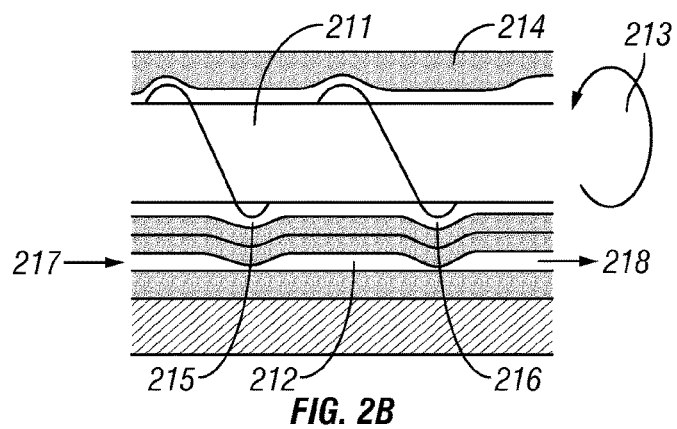
Figure 3:
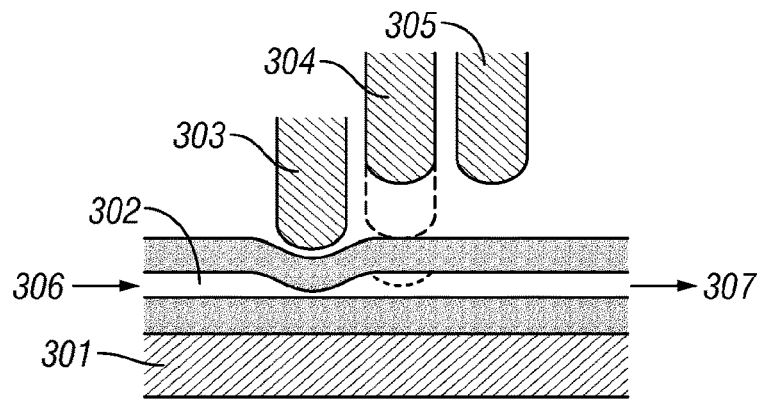
FIG. 3 show schematically two implementation of peristaltic pumping, as described in Gu et al. (2004) and Takayama et al. (2010).
Figure 4:
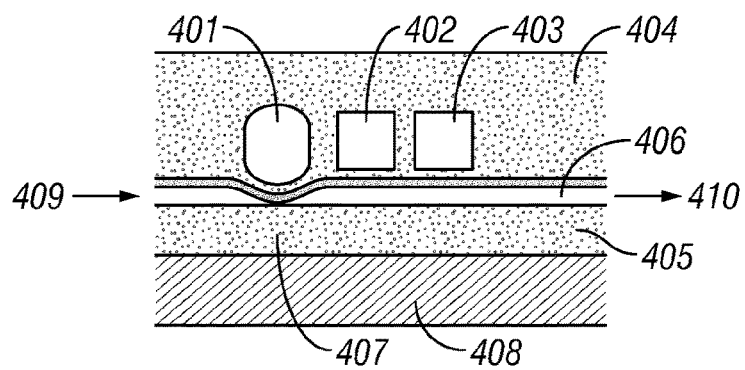
FIG. 4 shows schematically an implementation of peristaltic pumping, as described in Chou et al. (2001).
Figure 5:
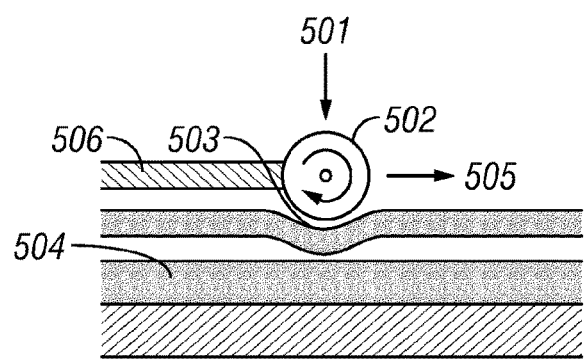
FIG. 5 shows schematically another means of inducing peristaltic compression, as described in Lim et al. (2004).
Figure 6:
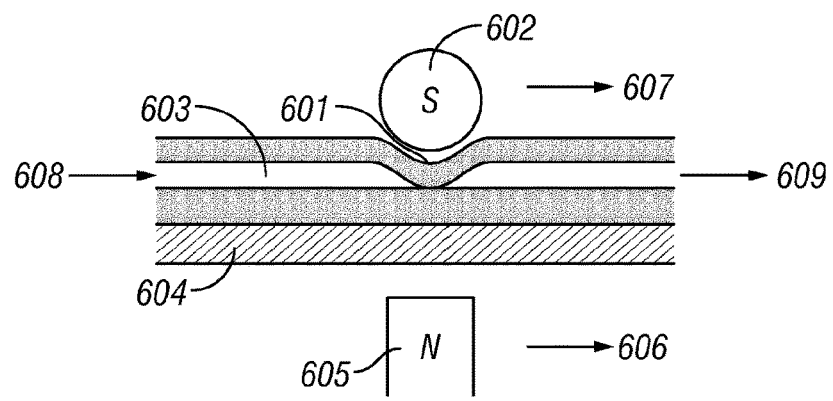
FIG. 6 shows schematically a means of creating continuous flow by using magnets and steel balls to create a circular compression zone that rotates along a circular pathway, as described in Yobas et al. (2008) and Du et al. (2009).
Figure 8:
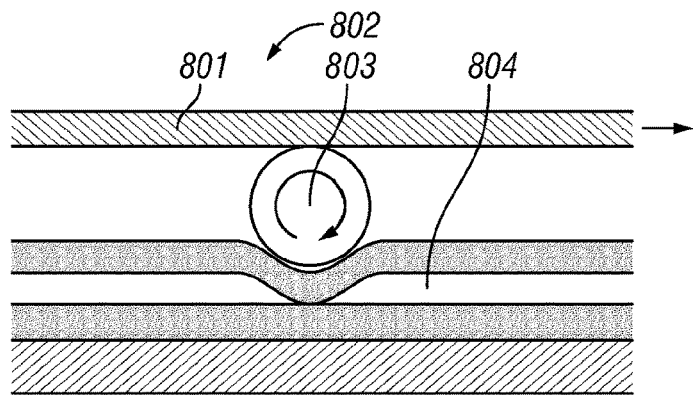
FIG. 8 shows schematically a means of causing rolling elements to rotate by turning a hard disk pressed against steel balls positioned over PDMS channels, according to certain embodiments of the invention.

During operation of pump 700, a z-axis stage control device can be used for variable compression as well as continuous flow capability. One limitation of this approach is the fabrication complexity and cost of the mechanical roller mechanism. In FIGS. 5 and 7, the rolling elements (502 and 702) are moved by a mechanical connection to the axle (506 and 703) that provides either translation (505) or rotation (704). In FIG. 6, the ball is moved by means of a rotating magnetic field gradient. FIG. 8 shows how the rolling balls could be caused to rotate by turning a hard disk (801) that is pressed (802) against steel balls (803) positioned over PDMS channels (804). This configuration, however, lacks an alignment system, which will eventually lead to the balls disengaging from the channel-disk system, and the differences in the coefficients of sliding friction and elasticity between the PDMS, the balls, and the hard plate could lead to the plate slipping against the balls, which then would not rotate or roll.

Figure 9:
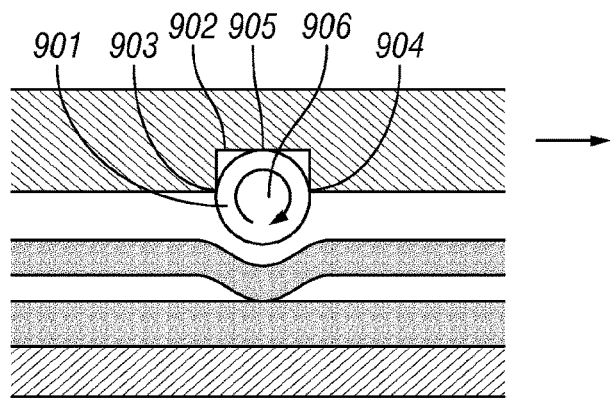
FIG. 9 shows schematically that a series of balls could be pushed simultaneously by capturing each ball in a circular array of sockets, i.e., a cage., according to certain embodiments of the invention.

FIG. 9 shows that a series of balls (901) could be pushed simultaneously by capturing each ball in a circular array of sockets (902) (a "cage"). This introduces a strict alignment system; however, it also could produce substantial sliding friction. Since the balls are captured by contact (903 and 904) with the sides of the cage (903 and 904) and the top (905), the sliding friction between the ball and the cage at these points opposes the balls' tendency to roll (906), introducing the possibility of the balls sliding across the PDMS surface rather than rolling. Because of this friction, the torque required for rotating a sliding ball and cage system is much greater than that of the rolling ball and cage system. Varying the cage's size introduces a trade-off between the ability of the ball to roll and the chances of a ball disengaging from the cage.

Figure 10:
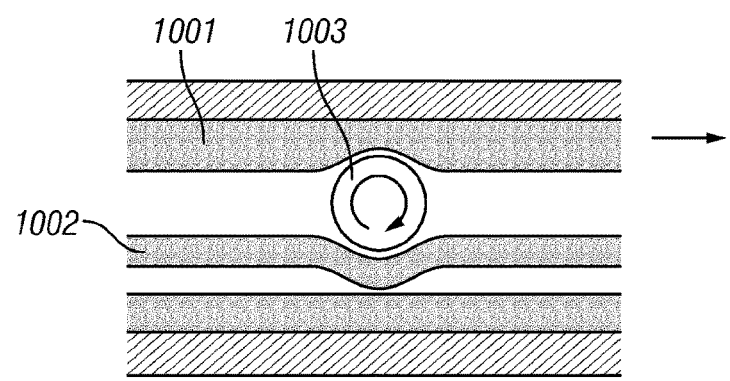
FIG. 10 shows schematically the use of a deformable rotating disk to drive rolling elements, according to certain embodiments of the invention.
Figure 11:
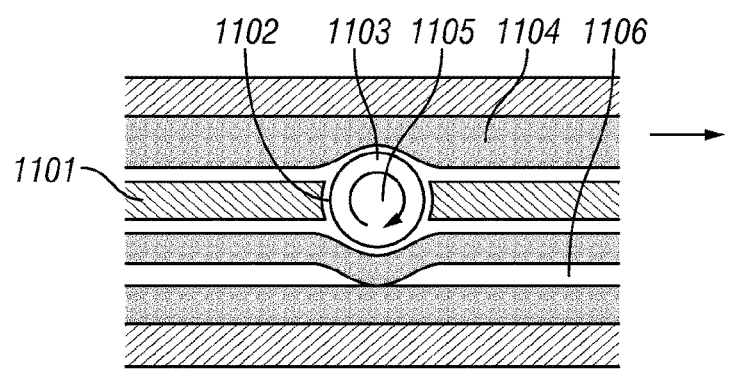
FIG. 11 shows schematically the use of deformable PDMS or another elastomer disk to provide the force that causes the array of balls to rotate, according to certain embodiments of the invention.

Embodiments of the present invention comprise numerous features that provide benefits over existing configurations. For example, certain embodiments of the present invention include the use of a deformable rotating disk to drive rolling elements, (e.g., steel balls in certain embodiments), as shown in FIG. 10. By using PDMS or another elastomer for both this driving disk (1001) and the microfluidic device (1002), the elastic deformations above and below the steel balls (1003) are matched, drastically reducing the incidence of sliding friction. The array of balls is kept in alignment by a cage (1101) with a circular array of openings (1102) for the balls (1103) (FIG. 11). The cage is free-floating and therefore does not provide the force that causes the array of balls to rotate. This force is provided instead by the deformable PDMS or other elastomer disk (1104), which results in the balls moving with rolling (1105) rather than sliding friction. A convenient analogy of the two means to roll the balls, i.e., with a rigid or deformable disk, is to consider rolling an apple between a book and the palm of the hand, versus between two hands. In the former case, the book is likely to slide against the apple due to the elastic forces provided by the lower hand and the smaller sliding friction between the book and the apple, as compared to that between the apple and the hand. In the latter case, the elastic deformations of both hands are matched to each other and the apple rolls easily. With the deformable driving disk, the balls actually drive the cage, and since little force is applied to the cage, little work is required to rotate it and hence there is little power dissipation associated with the cage. This system can in fact be constructed in the same manner as a thrust bearing. The balls act as bearings between the PDMS disk (1104) and channeled device (1106). The upper PDMS disk drives the thrust bearing over a circular path above the channels in the lower PDMS device. The cage simply keeps the balls aligned, both radially and tangentially.

Figure 12:
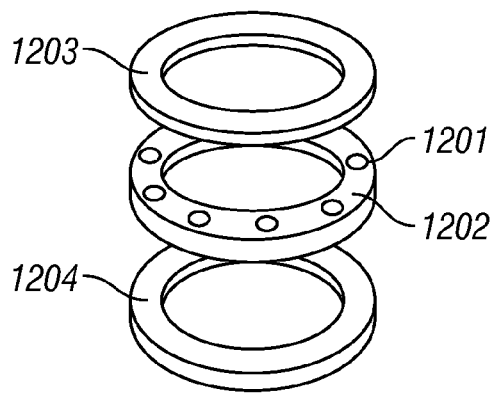
FIG. 12 shows schematically a thrust bearing that compresses the microfluidic channels, according to certain embodiments of the invention.
Figure 13:
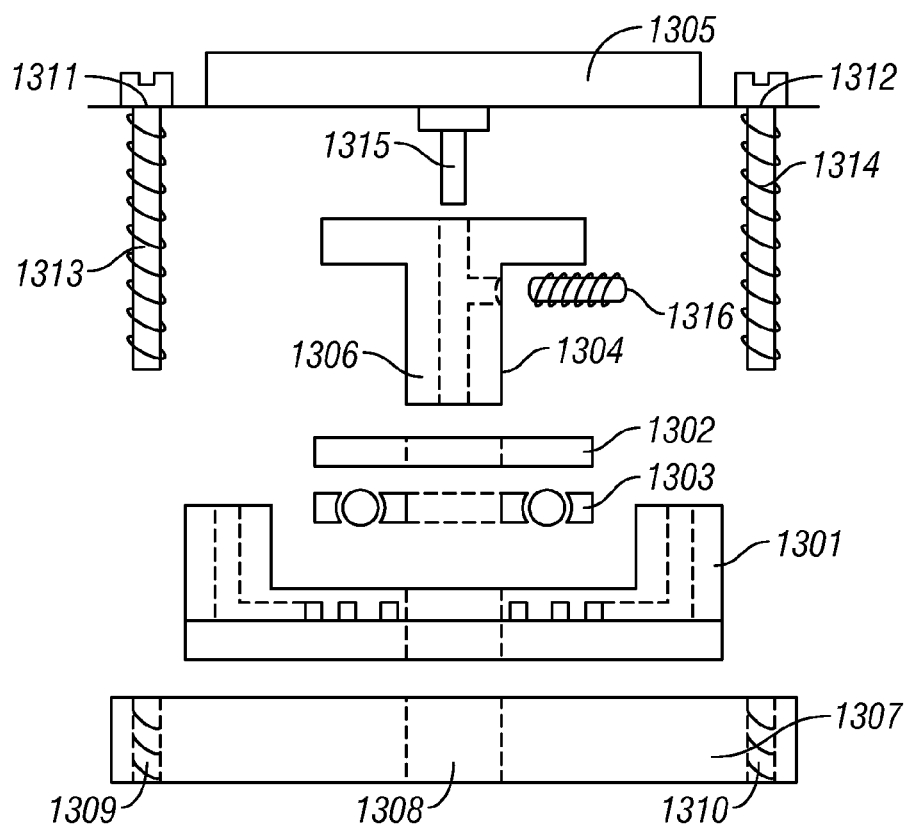
FIG. 13 shows schematically exemplary embodiments of the rotary planar peristaltic micropump (RPPM).

In certain embodiments of the present invention, the rotary planar peristaltic micropump (RPPM) uses a thrust bearing (FIG. 12) to compress microfluidic channels. As an upper disk is rotated, the balls (1201) within the thrust bearing roll to create the moving compressional wave that drives fluid through the underlying channels that could be contained within the lower element (1204) were it fabricated from an elastomeric material. The cage (1202) of the thrust bearing confines the balls as they roll, but does not provide enough friction to cause sliding. This is another advantage of the RPPM. Many previous peristaltic pumps, including that of Darby et al., involve significant frictional forces caused by the dragging of the compressing object along the surface, an issue that the matched rolling action of the RPPM's thrust bearing and the two matched deformable surfaces avoids. With rolling friction, the wear on the PDMS pieces, particularly the channeled device, is greatly reduced as compared to a design with sliding friction, allowing for prolonged use of the device. A standard thrust bearing also contains two inelastic washers (1203 and 1204), usually metallic in nature, that sit above and below the ball (1201) and cage assembly (1202). In exemplary embodiments of the RPPM design (FIG. 13), these washers are made of PDMS, with the bottom washer comprising the channeled PDMS microfluidic device (1301), and the top washer being the aforementioned disk (1302) that drives the rotation. The bearing (1303) is turned by the frictional forces acted on it by 1302, which is attached to a coupler (1304) that is turned by a stepper motor (1305). In specific embodiments, the coupler (1304) may be custom-machined metal or plastic.

In an ideal system with only rolling friction, the bearing cage turns at exactly half the rate of the motor. The coupler (1304) contains a shaft (1306) that provides axial registration for the PDMS disk (1302), the thrust bearing (1303), and PDMS device (1301). The shaft terminates within a circular opening at the center of a disk (1307) that serves as the ultimate base of the entire device. In certain embodiments, the disk (1307) may be formed from polycarbonate or other material. Along with the center hole (1308), disk (1307) contains tapped holes (1309 and 1310) along the edge that correspond to openings (1311 and 1312) on the mounting of the stepper motor. Altogether, the PDMS pieces, the stepper motor, the metal or plastic coupler, the polycarbonate base piece, and the mounting screws (1313 and 1314) comprise an exemplary embodiment of an RPPM system.

Figure 14:
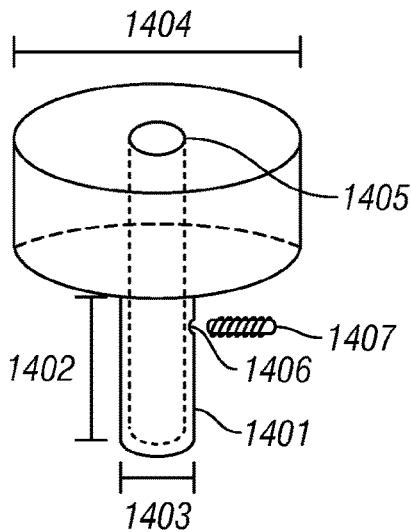
FIG. 14 shows schematically the coupler comprising a shaft and hub, according to one embodiment of the invention.

In the embodiment shown in FIG. 14, the coupler 1304 comprises a shaft (1401) with a diameter just under the inner diameter of the desired bearing and a hub (1404) at least as large as the outer diameter of the bearing. The length of the shaft (1402) determines the total allowable thickness of the PDMS washer, bearing, and PDMS channels. Taking into consideration these parameters, an additional distance (e.g., 2-5 mm) is needed so that the shaft extends into the polycarbonate base. The diameter of this shaft (1403) is determined by the inner diameter of the bearing used. The shoulder on the coupler is of a diameter (1404) that is larger than the bearing outer diameter. A center hole (1405) in the coupler provides a connection to the motor shaft, and a tapped hole (1406) and set screw (1407) secure the coupler to the motor.

Figure 15:
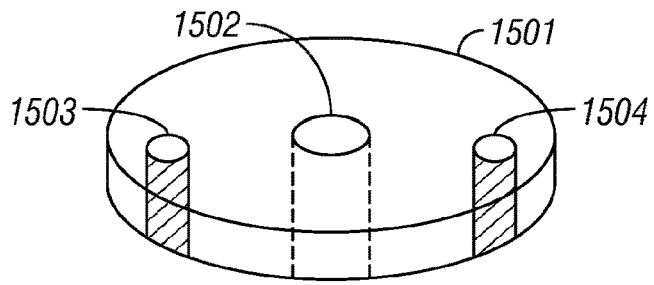
FIG. 15 shows schematically a configuration of the base piece, according to one embodiment of the invention.

The base piece (FIG. 15) shown here as a circular disk (1501) has a centered hole (1502) that is just larger than the metal or plastic shaft. Two threaded holes (1503 and 1504) match the holes on the motor mount (1311 and 1312), and provide and control compression to the device. Depending on the stability and configuration of the mount and motor used, this base piece may contain, for example, up to 4 mounting holes. Other configurations of the base, motor mount, and drive components are also possible in other exemplary embodiments.

Figure 16:
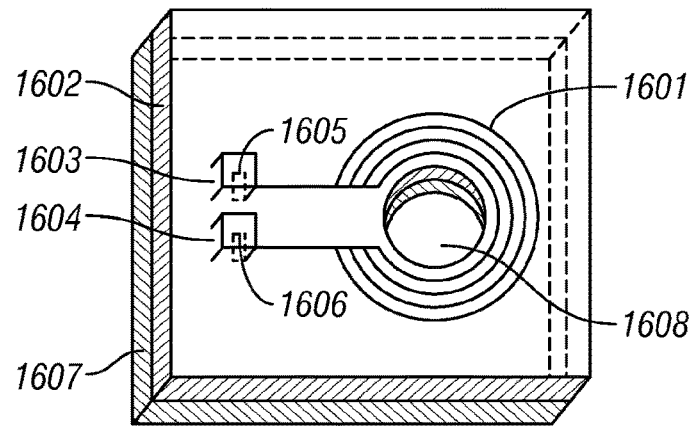
FIG. 16 shows schematically the microfluidic components fabricated using soft lithographic techniques and replica molding, according to one embodiment of the invention.

The fabrication of the microfluidic device (FIG. 16) can be accomplished with soft lithographic techniques and replica molding. In certain embodiments, the master mold can be created in a photolithographic process that uses a silicon wafer and SU-8 negative photoresist to produce a flat silicon base with raised patterned structures composed of cross-linked photoresist. The positive-relief pattern is created by shining UV light through a patterned mask onto a thin layer of SU-8 negative photoresist residing on the silicon wafer. Restricted by the usage of a thrust bearing, the microfluidic design requires a circular compression zone. The size of these radially arranged channels is determined by the size of the thrust bearing. Exemplary embodiments contain multiple concentric channels (1601) to ensure that a slightly off-center placement of the thrust bearing will still cause flow, or to allow increased flow rates for a given rotational velocity.

In one exemplary embodiment, to create the microfluidic device, a thin layer of PDMS (1602) (e.g., 100 µm in certain exemplary embodiments) is spun onto the silicon master. Pre-cured tubing-support cubes of PDMS (1603 and 1604) are then placed over the input and output holes of the master and the entire device is allowed to cure. The cured PDMS is then carefully removed from the wafer and I/O holes (1605 and 1606) are punched through the PDMS cubes. The punched device is then plasma bonded to another thin layer of cured PDMS (1607). Lastly, a hole for the metal or plastic shaft (1608) is punched at the center of the bonded device.

Altogether, the components described above comprise an exemplary embodiment of a rotary planar peristaltic micropump. Assembly instructions for the exemplary embodiment described above follow. It is understood that the following assembly description is merely one example of assembly, and that other suitable alternatives may be substituted for certain components or steps. For example, the retainers may be configured differently than shown and described.

To assemble the pump, the coupler (1304) is slid onto the motor's (1305) shaft (1315) and secured using a retainer (1316) (e.g., a set screw). The PDMS washer (1302) can then be added onto the shaft of the coupler (1304), followed by the thrust bearing (1303), followed by the channeled PDMS device (1301). The end of the coupler's shaft (1306) fits into the center hole (1308) of the base piece (1307). The pieces can then be secured together with adjustable retainers (e.g., machine screws) (1313 and 1314) passing through the motor mount (1311 and 1312) and terminating in the tapped holes (1309 and 1310) in the polycarbonate base (1307). Loosening or tightening the adjustable retainers (1313 and 1314) controls the amount of compression felt by the channels.

Exemplary embodiments of the present invention offer numerous advantages over other peristaltic pumps used in microfluidic devices. Many current microfluidic systems are driven by computerized mechanical pumps, for example, linear syringe pumps, or by banks of computer-controlled solenoids to deliver pressure to selected control channels. Compared to these expensive pumps, which require a computer or microprocessor and either complex mechanical actuators or expensive valve banks and a pressure regulator, exemplary embodiments of the present invention require a simple motor to turn the assembled device. In contrast to many peristaltic pumps in microfluidic devices, when the motor driving various embodiments of the present invention is turned off, regions of compression remain in the channels and block passive forward or reverse flow through the pump. Also, with peristalsis, the system does not directly pump from a reservoir, thus allowing for the possibility of a recirculating setup that addresses the problem of a finite reservoir and permits prolonged experimentation that requires little to no maintenance.

Figure 17A:
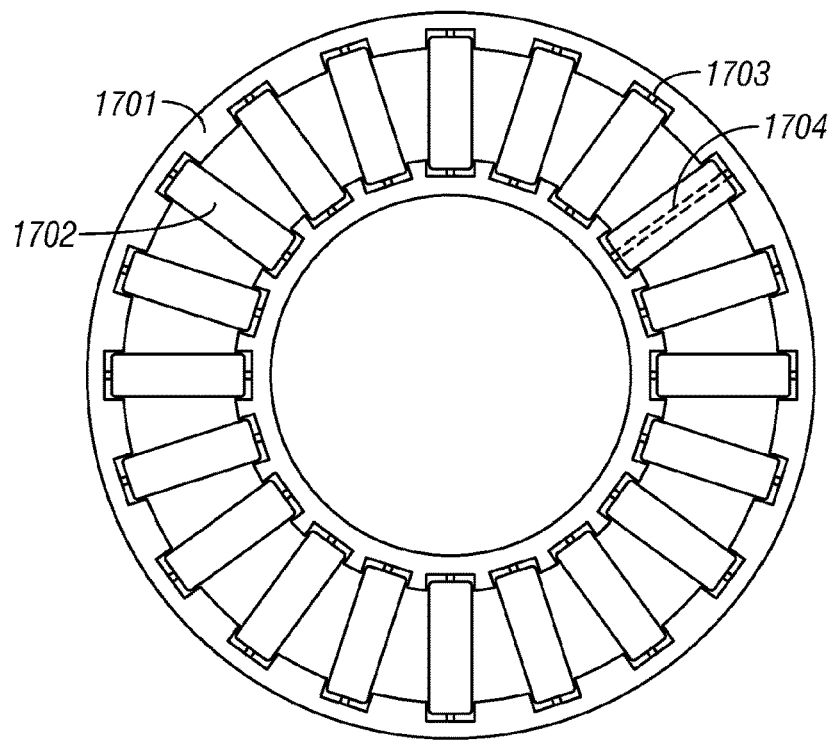
FIGS. 17A-17B show schematically a roller thrust bearing, in certain embodiments of the invention.
Figure 17B:
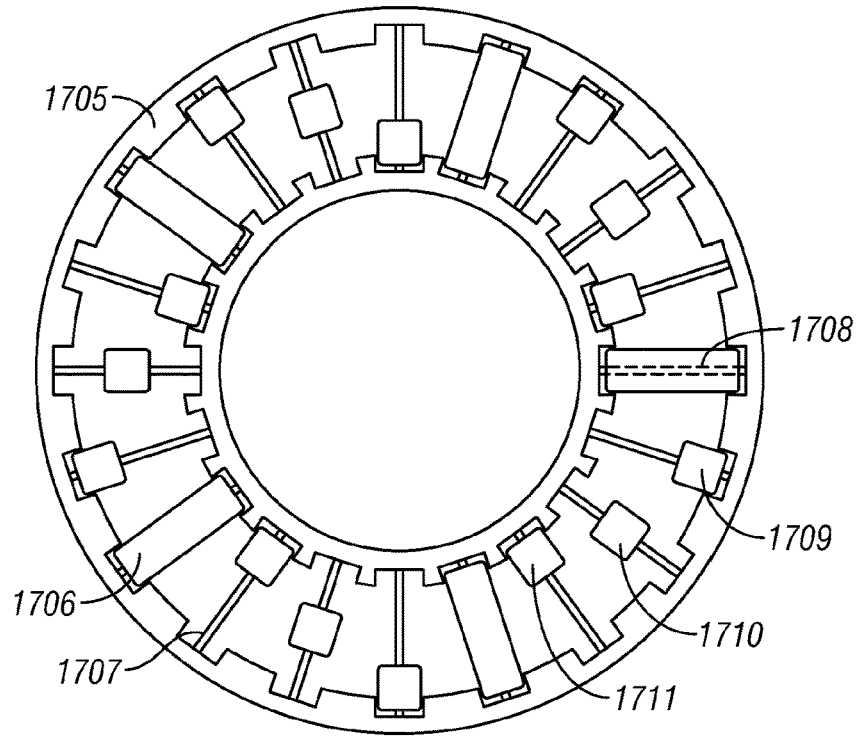

Exemplary embodiments of the present microfluidic peristaltic pump may be used for microfluidic mixing. By reconfiguring the channeled PDMS device and replacing the ball thrust bearing (FIG. 12) with a roller thrust bearing (schematics shown in FIGS. 17A and 17B), many different mixer designs can be fabricated. The roller thrust bearing features a cage (1701 and 1705) and rolling elements configured as cylindrical rollers (1702 and 1706) coupled, for example, to the cage via pins (1703 and 1707) that pass through a central hole (1704 and 1708) in each of the cylindrical rollers. FIG. 17B shows rollers of variable length and placement (1709-1711), which prove useful in mixing applications.

Figure 18A:
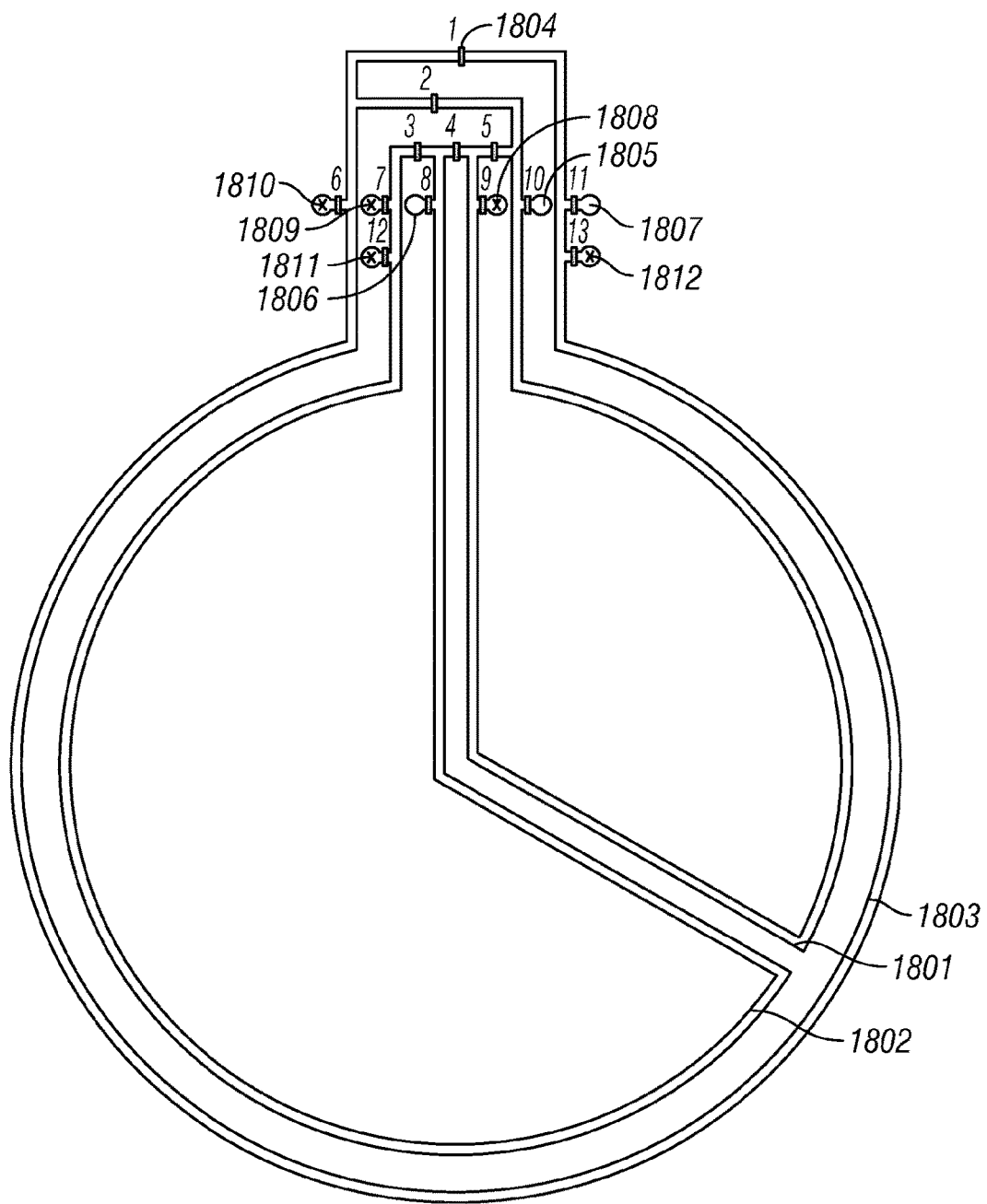
FIG. 18A shows schematically a multipath-design mixer, according to one embodiment of the invention.
Figure 19:
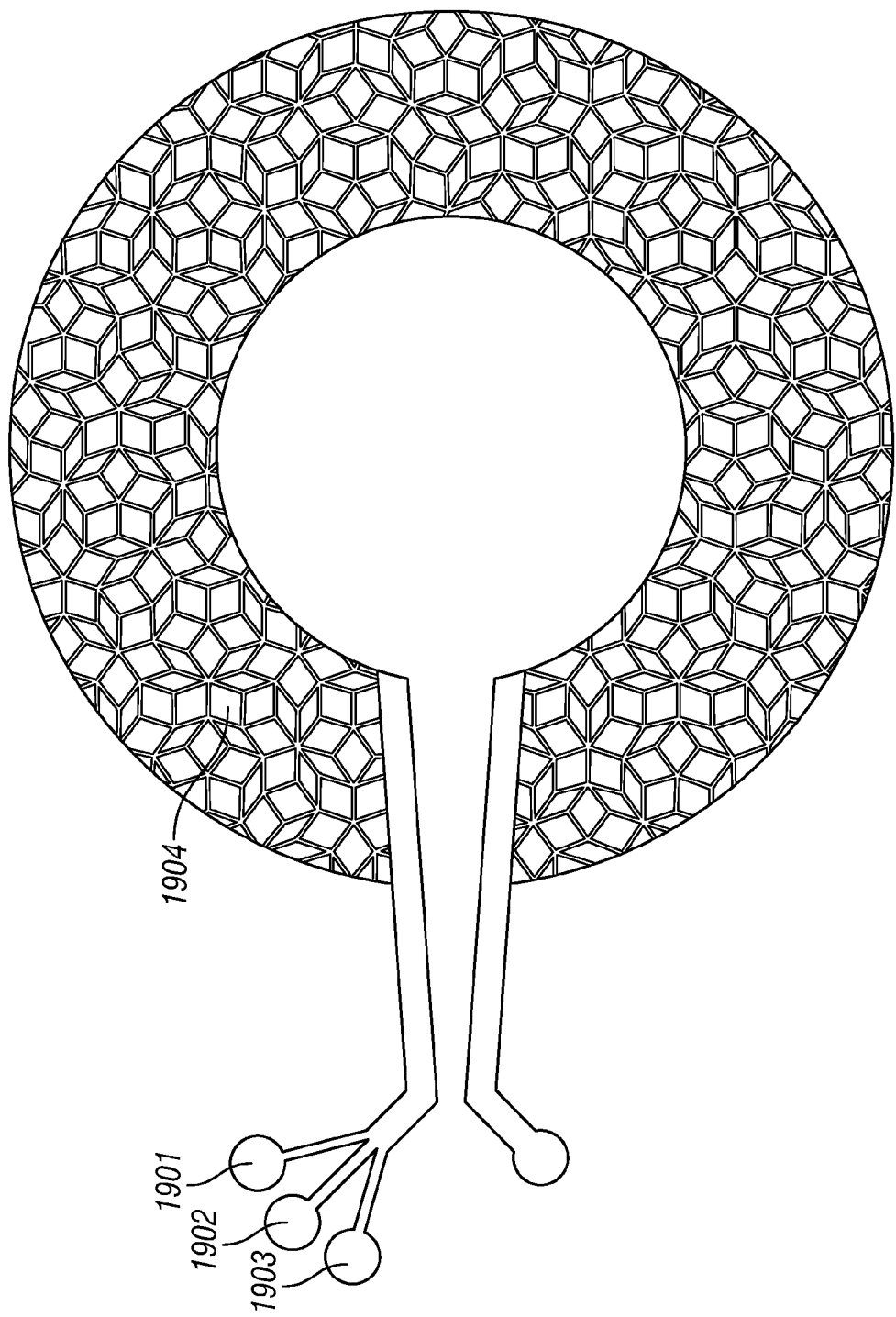
FIG. 19 shows schematically an aperiodic pattern of splitting and recombining flow streams in a circular Penrose design, according to one embodiment of the invention.

FIG. 18A shows a multipath-design mixer, with three channels (1801-1803) with a path length ratio of roughly 1:2:3. A series of 13 valves (depicted by rectangles, e.g., 1804) controls each of the six modes for the pump. One exemplary configuration of the valves for each mode is shown in FIG. 18B (Table 1). 1805-1807 are three possible inputs for this design, and 1808-1810 are the three possible outputs. The nodes denoted by asterisks (1811 and 1812) are connected via tubing and used only during the series recirculation mode. This design would most likely utilize the roller thrust bearing shown in FIG. 17A. A second possible mixer design would use a pattern derived from Roger Penrose's aperiodic set of thick and thin rhombus tiles. This design, shown in FIG. 19, has multiple inputs (1901-1903) to allow for parallel loading of mixing components, and a circular Penrose design (1904) that is compressed by a roller bearing as shown in FIG. 17A or 17B. A series of valves similar to those used in FIG. 18 could also be incorporated in this design for greater control of mixing modes. Using the variable length rollers (1709-1711) of FIG. 17B along with the aperiodic pattern of FIG. 19 can create a unique scenario of splitting and recombining flow streams that will increase mixing efficiency. The long rollers would ensure that the solution had a net tangential flow around the pump and was completely expelled from the pump at the end of the mixing process, and the short rollers would provide a local circulation that would enhance mixing efficiency. Combining either of the mixing designs with a valve bank would also allow for the fabrication of a rotary reagent formulator.

It is important in many biological and chemical research projects to be able to produce solutions that contain a large number of different chemical substances at differing concentrations. Historically, preparation of these solutions would be done by separate weighing, volume measurements, serial dilutions, and mixing. More recently, this process has been automated by the use of either manual pipetting with controlled dispensing, or by acoustic droplet generators.

Two main types of microformulator devices have been created. One type is a junction at which multiple input channels of fluid are combined into a single channel and then mixed, either by lateral diffusion over the length of a long channel, or by other mixing approaches, such as chaotic mixers or three-dimensional mixers. The concentration of each fluid can be controlled by the input velocity of their respective channels. Junction mixers are fast but are accurate for only two different fluid inputs. The second type is in the style of the Hansen et al. (2004) device, which at present represents the state of the art in microfluidic formulators. Hansen devised a microfluidic microformulator that utilized a large number of pneumatically operated valves and pumps to mix picoliter volumes from 32 reservoirs that could be loaded with different chemical solutions. In this type of microformulator, fluids from multiple input channels are serially loaded into a mixer system, the output of which is then pumped from the device. The Hansen-style microformulator creates accurate mixtures, although it is slow due to its serial nature. Other limitations of this system include the large number of valves, the low volume of the device, and the time required to produce and mix a microliter of solution.

Exemplary embodiments of the invention using a rotary planar peristaltic micropump can be extended to create a microformulator of a different design: a system that can rapidly combine, mix, and dispense a solution that contains an arbitrary number of solutions combined at controlled volumes to achieve the desired concentration of each component.

The rotary planar peristaltic micropump (RPPM) (FIGS. 13-16) can be combined with microfluidic channels and a loading system to form a microformulator, identified as a rotary microformulator. The use of the RPPM as the driver of a microformulator is an improvement of current microformulators, in part due to its speed, versatility, accuracy, and small size.

Figure 20:
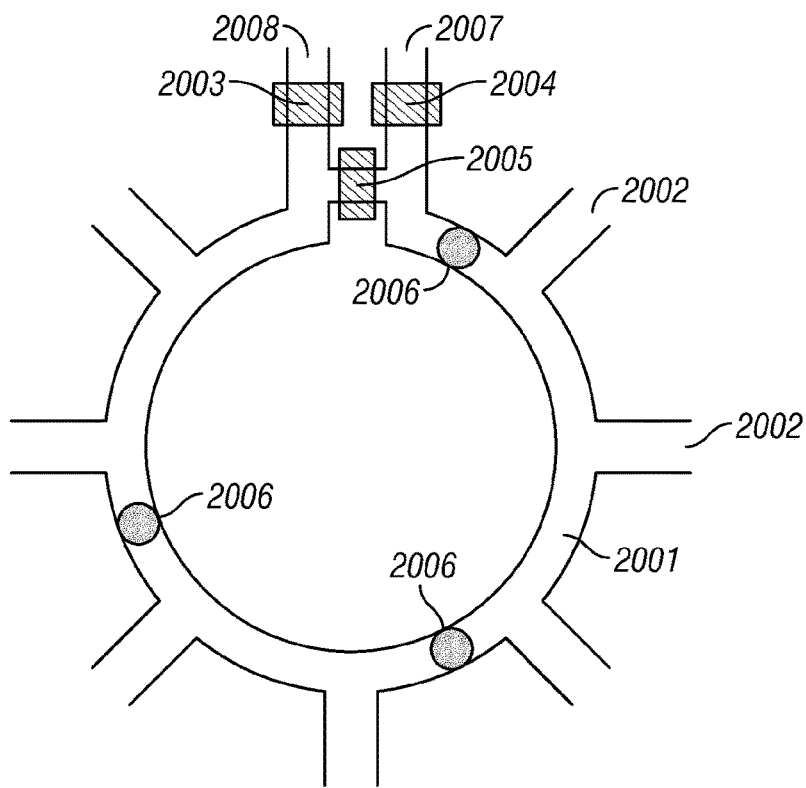
FIG. 20 shows schematically a rotary microformulator, according to one embodiment of the invention.

The functionality of the rotary microformulator (FIG. 20) is accomplished with a circular channel (2001) containing radially arranged inputs (2002). The RPPM compresses this channel to cause fluid flow. The rotation of the bearings (2006) or rollers of the RPPM over the flow channel (2007) causes fluid to be pumped through the channel. This driving action of the bearings allows for precise control over the flow rate of the fluid, facilitating precise metering of both input and output solutions. The RPPM also allows for high flow rates compared to those of alternative methods, allowing for fast mixing of larger volumes of liquid.

Valves are used to control the flow configuration of the rotary formulator. When the valve on the connecting or bypass channel (2005) is closed and the others are open, fluid flows from the input channel (2007) to the output channel (2008). When the input valve (2004) and the output valve (2003) are closed and the connecting valve (2005) is open, the main channel forms a closed path through which the RPPM can induce continuous recirculatory flow. The recirculation of flow allows for rapid solution mixing. Multiple input solutions can be loaded into the channel either in flow configurations using methods involving such structures as multiplexers or in radially arranged inputs (2002).

Alternatively, the device can be used to mix an arbitrary number of solutions in a strictly linear path as opposed to a recirculating loop. The RPPM can draw fluid in from a multiplexer or radially positioned inputs, which lets various solutions into the mixture in quantities controlled by varying the time and frequency that the channel to each reservoir of solution is open. As the pump runs, it draws in each solution in proportion to the time that each reservoir channel is open. To facilitate the mixing process, the opening of the reservoirs is alternated so that the distance that each bolus of solution must diffuse is minimized. Once the correct ratios of solutions are drawn from their respective reservoirs, the mixture is pumped through a long, meandering pathway so that when the fluid is pumped out of the device, it is fully mixed. Using such a device, the composition of the mixture can be dynamically varied (i.e., sinusoidal variation of certain solutions) simply by varying the solution inputs. Such a device would be advantageous because the rotary planar peristaltic micropump eliminates the need for multiple pumps, while still maintaining a high pumping rate.

An almost sinusoidal concentration of an output mixture of two solutions is accomplished with two converging channels whose widths vary according to sinusoidal relationships. The flow rate of the channels produced by the rotating bearings or rollers of the RPPM varies according to the widths, causing the converged mixture to have sinusoidal concentrations over time.

Solution input into the device is accomplished by connecting channels to the main fluid flow channel. Valves are used to control the opening and closing of these input channels. Implementations of this general input structure can be accomplished in a number of ways. The simplest approach that is sufficient for serial output of mixtures is the use of a single multiplexer that connects to the input of the device, functioning similarly to the Hansen et al. (2004) formulator. The bearings rotate a certain amount to load solutions from the multiplexer serially to achieve the desired mixture. A multiplexer can also be used along the perimeter of the circle to allow for very rapid input. In this configuration, the multiplexer loads channels connected to the main fluid flow path in defined amounts. As the RPPM rotates, the fluid is drawn in.

Figure 21:
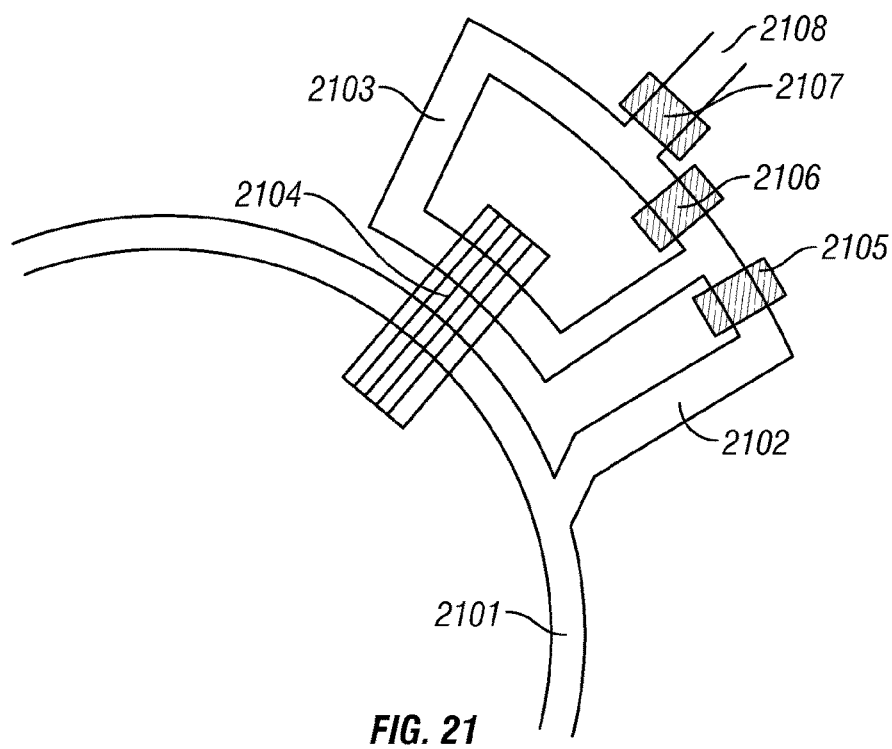
FIG. 21 shows schematically the use of recirculating fluid input holder channels that remain in contact with the rollers of the RPPM for metering the addition of a solution to the mixer, according to one embodiment of the invention.

Another method for fluid input, shown in FIG. 21, is through the use of recirculating fluid input holder channels (2103) that remain in contact with the rollers (2104) of the RPPM. The fluid input holder channel (2103) is connected to the main flow channel (2101) through a valved angled channel (2102). When a single path is formed between the fluid input supply (2108) and the main fluid channel (2102) by closing only one valve (2106), the roller meters solution into the mixture. When the path is closed from the fluid input supply (2108) to the fluid channel (2101) by closing the connecting valve (2105) and the supply valve (2107), the fluid in the input holder (2103) simply recirculates along the closed path. Hence the roller is continuously moving fluid in a peristaltic fashion, and the selection of which valves are open or closed determines whether injection or recirculation is recurring, but in no case are large pressures developed by having a peristaltic pump attempt to move fluid past a closed valve.

Figure 22:
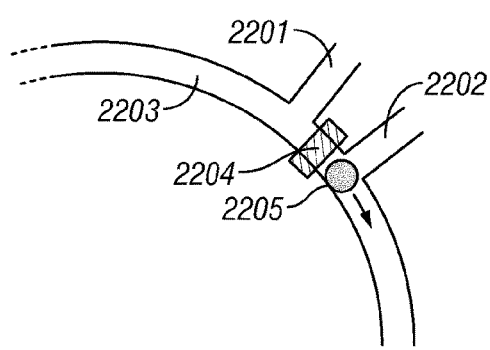
FIG. 22 shows schematically a fluid input method using a valve with an input and output channel on either side, according to one embodiment of the invention.

An additional fluid input method, shown in FIG. 22, uses a valve (2204) with an input (2202) and output (2201) channel on either side. As a roller (2205) of the RPPM rolls over the valve (2204) and past it, fluid in the main channel (2203) is directed out of the output channel (2201) and fluid from the input channel (2202) is directed into the mixer at main channel (2203).

Figure 23:
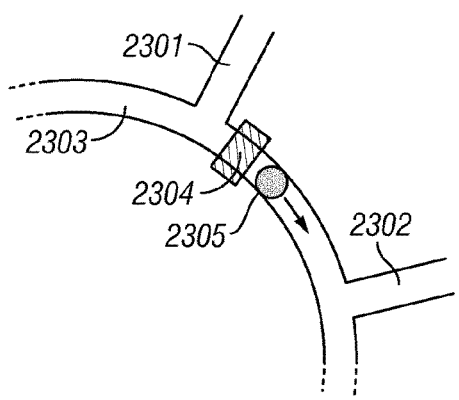
FIG. 23 shows schematically a radial arrangement of fluid inputs along the perimeter of the circular channel, according to one embodiment of the invention.

Alternatively, as shown in FIG. 23, the fluid inputs can be arranged radially along the perimeter of the circular channel (2303), each inlet (2301) being immediately preceded by an outlet (2302) and a valve (2304). To load fluid, the device is initially loaded with an arbitrary solution, such as water. As a roller (2305) moves across the valve, the valve blocks the main channel and forces fluid out through the outlet (2302). A vacuum is then formed between the PDMS and the substrate, so when the rollers move past the solution inlet (2301), fluid is drawn in. Using this method, the volume of each solution input can be varied by actuating the valves in a certain sequence and precisely varying the rotation of the bearings.

The use of pneumatic microfluidic valves with the rotary microformulator can be accomplished with a multi-layer PDMS device. In the multiple layers the control channels of the valves are protected such that compression of the closed valve does not fully close the control channel. This allows a channel to be compressed by the RPPM despite being closed.

Figure 24:
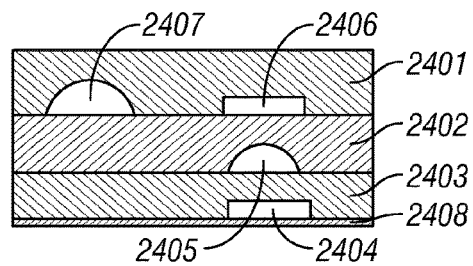
FIG. 24 shows schematically an implementation of valve protection for a valve outside of the main flow loop, according to one embodiment of the invention.

An implementation of this valve protection for a valve outside of the main flow loop is shown in FIG. 24. As rollers depress the pump channel (2407), the valve channel cover (2406) is also depressed, therefore protecting the valved channel (2405). The four-layer PDMS structure shown consists of a pump layer (2401), a valved channel layer (2402), a control layer (2403), and a base layer (2408). The channel in the control layer (2403) contains the control channel (2404), which expands with air to close the valved channel (2405). The pump channel (2407) is in the same layer as the valved channel cover (2406).

Figure 25:
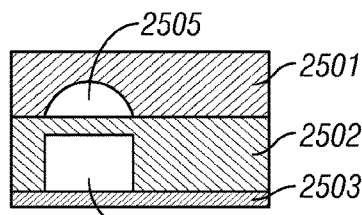
FIG. 25 shows schematically an implementation for a valved pump channel, in one embodiment of the invention.

An implementation for a valved pump channel is shown in FIG. 25. Whether or not the main flow channel (2505) in the pump layer (2501) is compressed by the control valve (2504), there remains sufficient space in the control valve (2504) in the control layer (2502) for proper functionality, regardless of the RPPM state. The base of the control valve (2504) is provided by the base layer (2503).

Figure 26:
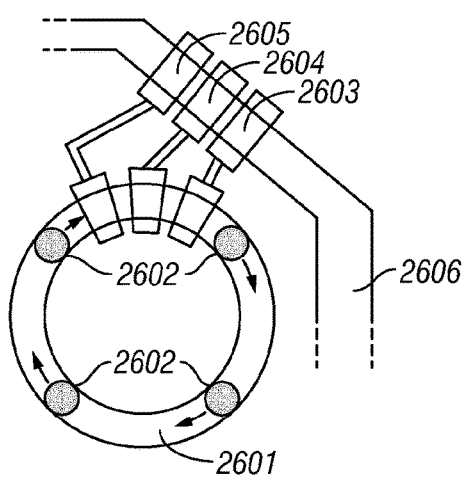
FIG. 26 shows schematically an implementation of rollers or bearings designed in conjunction with external structures such as closed channels that, for example, can be used to control metering, according to one embodiment of the invention.

The rollers or bearings can be designed in conjunction with external structures, such as closed channels, to provide functionality in addition to the pumping. This can be used, for example, to control metering. FIG. 26 shows an implementation of this hardwired functionality. As the rollers of the RPPM (2602) rotate around the flow channel (2601), they sequentially depress the closed valves (2605, 2604, 2603). The compression of the closed valves on one side by the rollers (2602) allows the closed valves to act as a pneumatically actuated peristaltic pump on a different channel (2606). Using this technique, an entire sequence of fluid flow handling events can be encoded in the rotation of the RPPM. This allows for complex devices to be controlled by a simple motor running at an arbitrary rate.

A mixer driven by an RPPM can be useful in experiments requiring a steady flow of a precise combination of solution components, even when those components must be dynamically and precisely varied. Previous mixers have used either a single pneumatically actuated microfluidic pump to draw fluid from different reservoirs, which cannot handle higher flow rates, or individual syringe pumps for each input solution, which are costly and complicated. Our device eliminates both of these limitations by using a single high flow rate peristaltic pump to draw each solution, eliminating the expense of multiple pumps. In addition, the use of an easily controlled motor and the lack of pressure-actuated valves allow the device to remain compact and suitable for on-site or low-resource settings. The device can be used to expand the repertoire of fluid flow operations that point-of-care microfluidic devices can perform.

Figure 27:
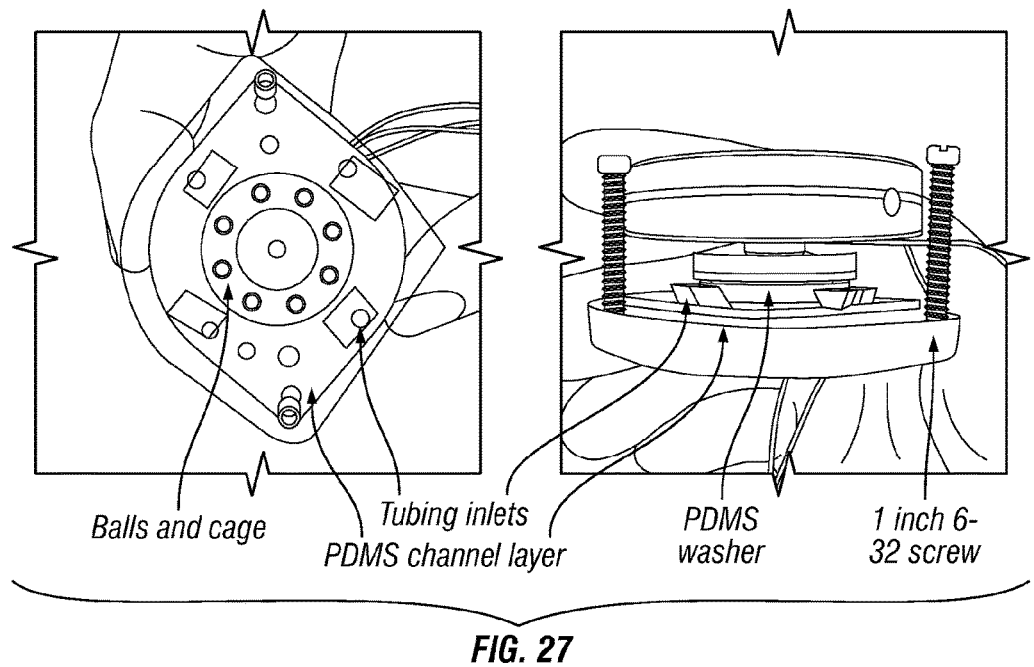
FIG. 27 and FIG. 28 illustrate schematically the first implementation of the RPPM.
Figure 28:
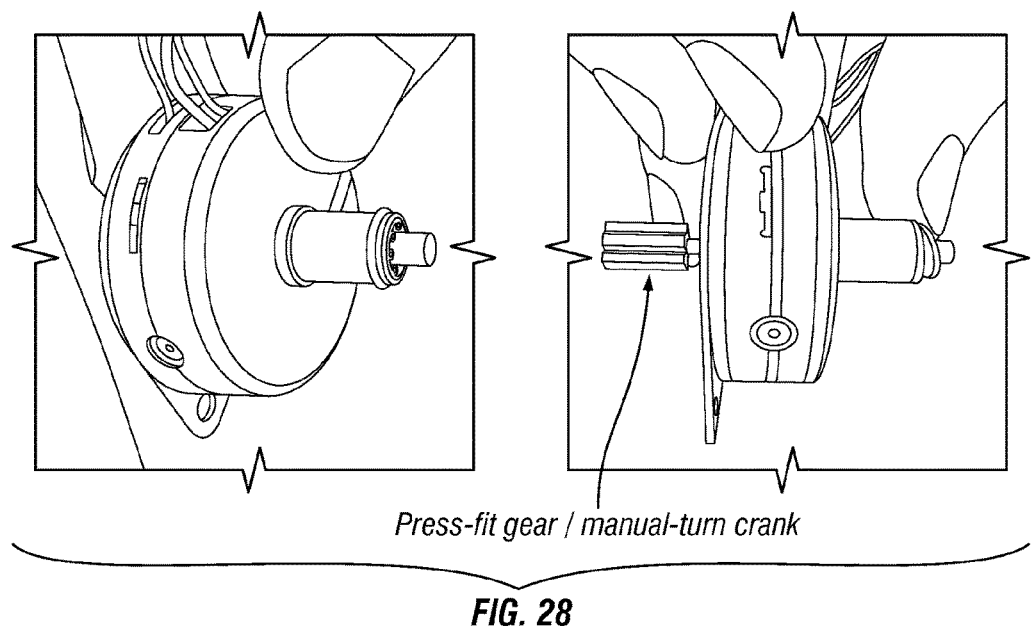
Figure 29:
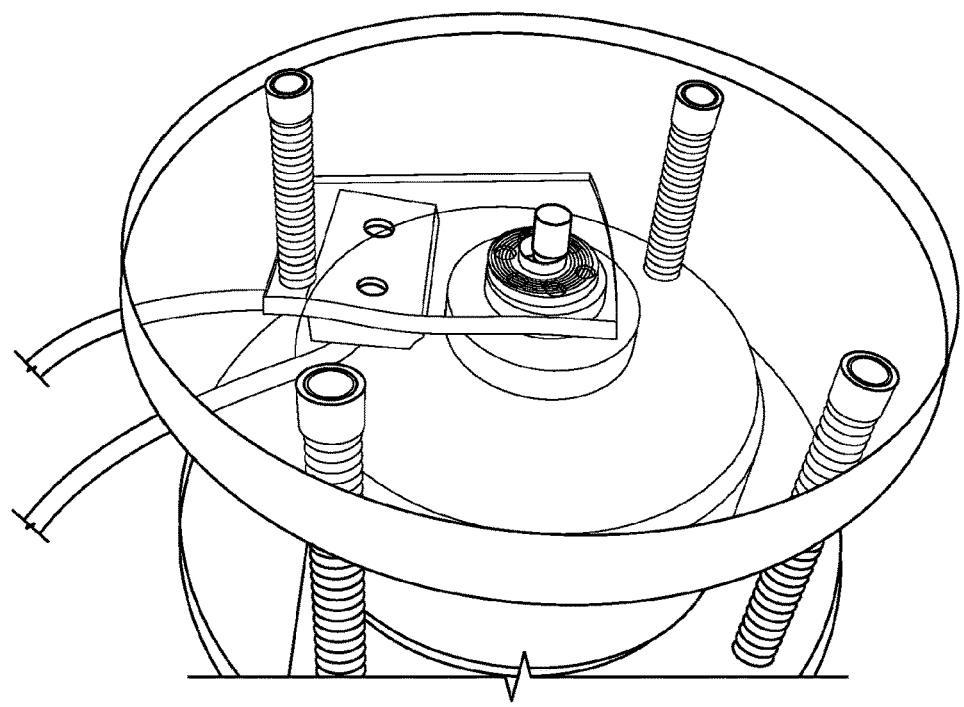
FIG. 29 and FIG. 30 illustrate schematically a simple rotary pump and a Penrose mixer, respectively, in a recent implementation of the RPPM.
Figure 30:
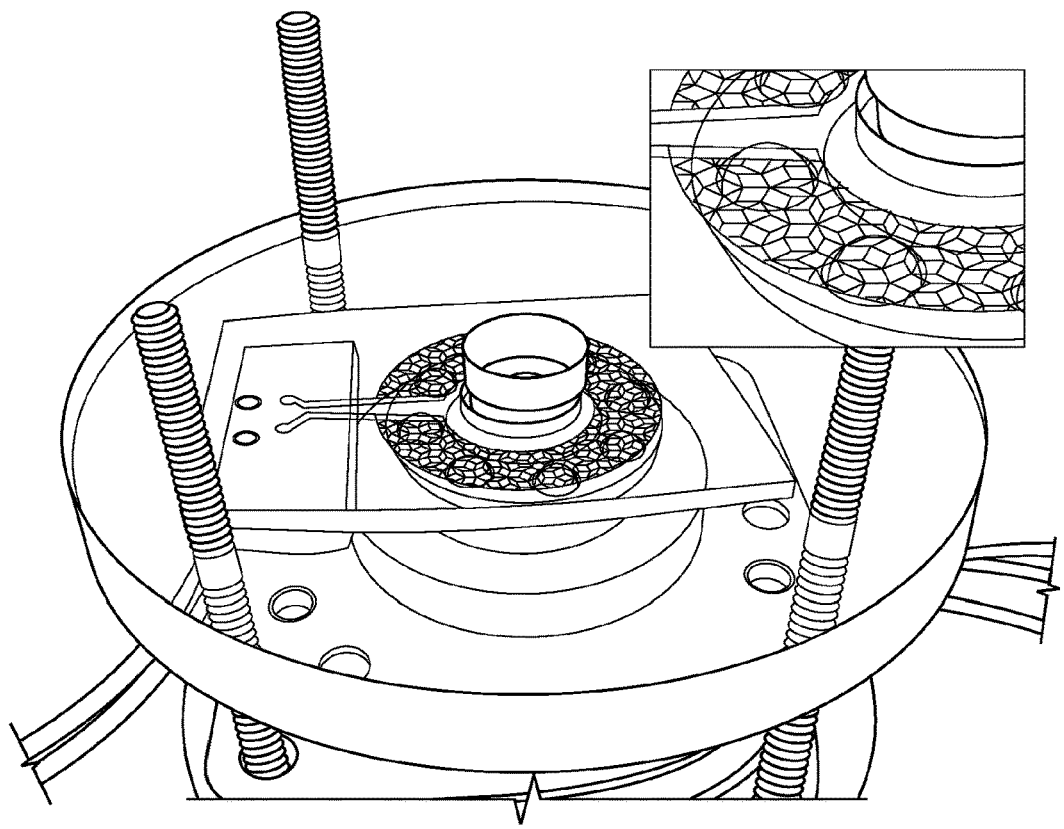

FIGS. 27 and 28 illustrate the first implementation of the RPPM, and FIGS. 29 and 30 show a more recent implementation, with FIG. 29 showing a simple rotary pump, and FIG. 30 showing a Penrose mixer.

Figure 31:
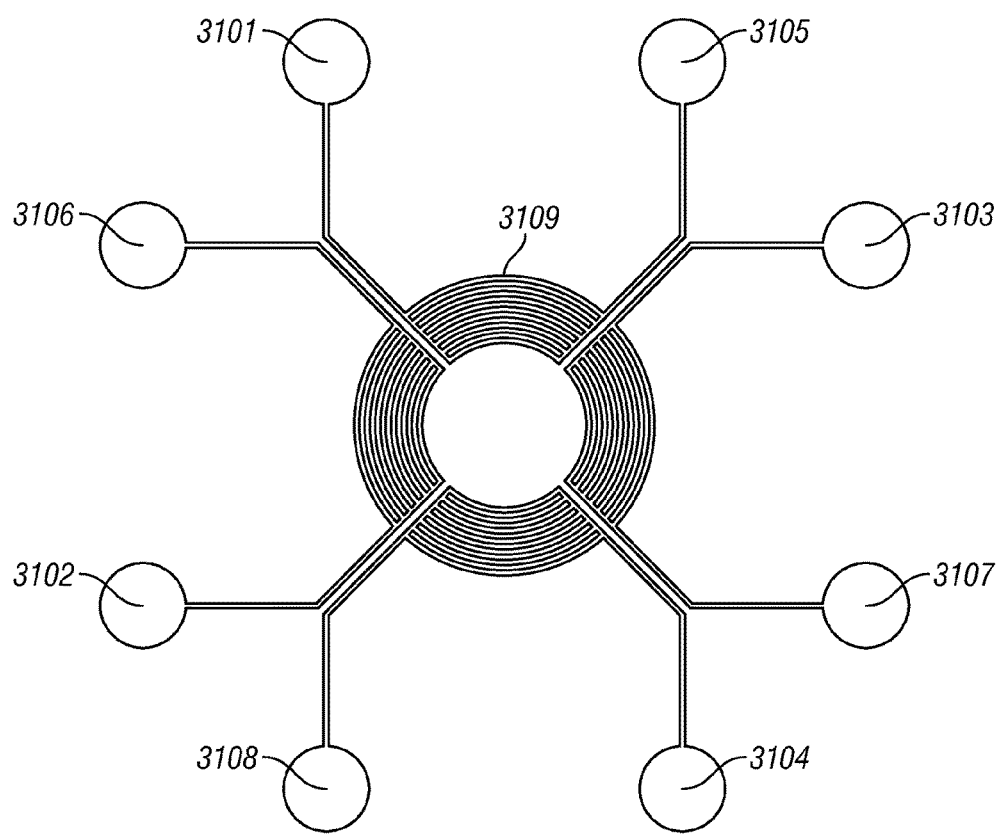
FIG. 31 shows schematically a configuration of the RPPM that provides support for separate, simultaneous pumping for multiple external devices, according to one embodiment of the invention.

Referring now to the exemplary embodiment shown in FIG. 31, the microfluidic portion of the RPPM can be configured to provide support for separate, but simultaneous pumping for multiple external devices. Fluid can be drawn in through the inlets or inputs (3101-3104) and pumped through concentric channels (3109) to the outlets or outputs (3105-3108). The angular extent of the channels (3109) in each section can be different to provide different pumping rates or duty cycles, depending upon the configuration of rollers (FIGS. 17A and B).

Figure 32A:
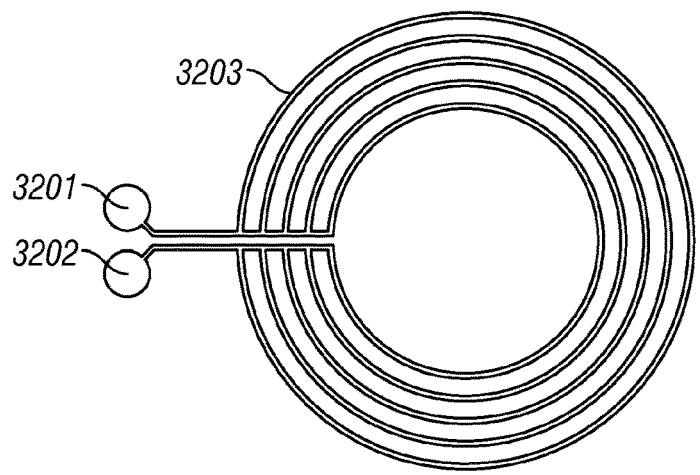
FIGS. 32A-32C show schematically variations of a microfluidic design having multiple concentric channels, according to certain embodiments of the invention.

In the exemplary embodiment of FIG. 32A, a microfluidic design is shown that could be used with the RPPM to pump a fluid from 3201 to 3202. This embodiment has multiple concentric channels (3203) to increase flow rate and protect against channel blockage.

Figure 32B:
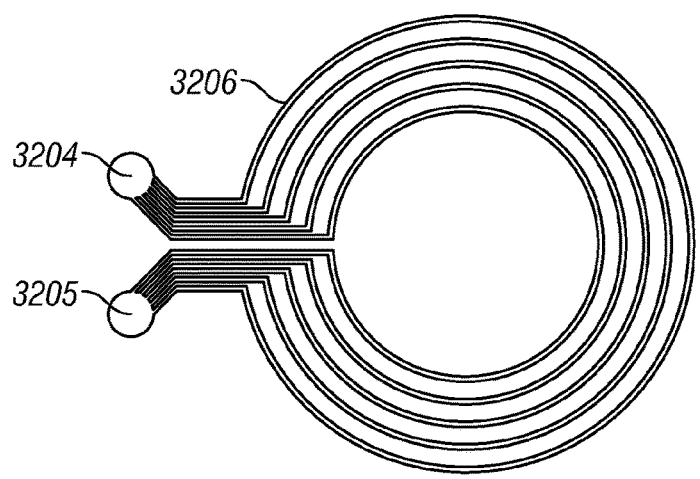

The embodiment illustrated in FIG. 32B shows a slight variation of 32A, with each of the concentric channels (3206) connected directly to the input (3204) and output (3205) nodes.

Figure 32C:
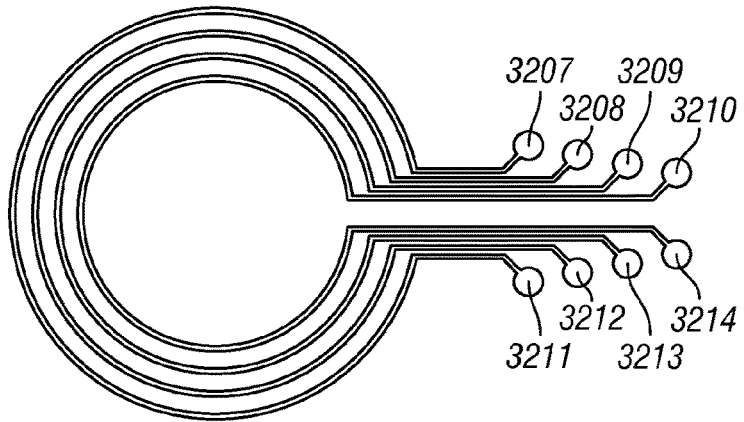

The embodiment of FIG. 32C provides a microfluidic design that could be used to pump several different fluids simultaneously and without crosstalk. Each of the inputs (3207-3210) has a corresponding output (3211-3214). In function, this embodiment is similar to the one shown in FIG. 31.

Figure 33B:
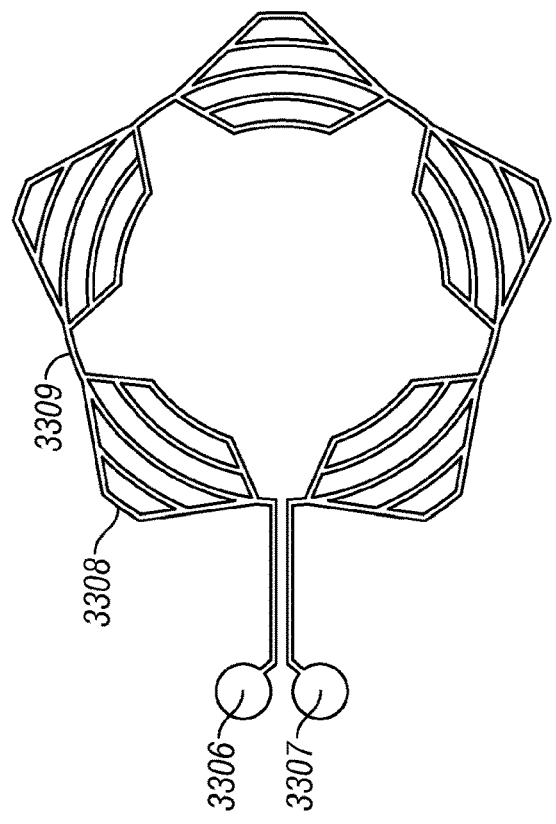
FIGS. 33A and 33B show schematically two embodiments of the invention with different microfluidic configurations for a multiple channel device that allows crosstalk between channels to allow, for example, mixing.
Figure 33A:
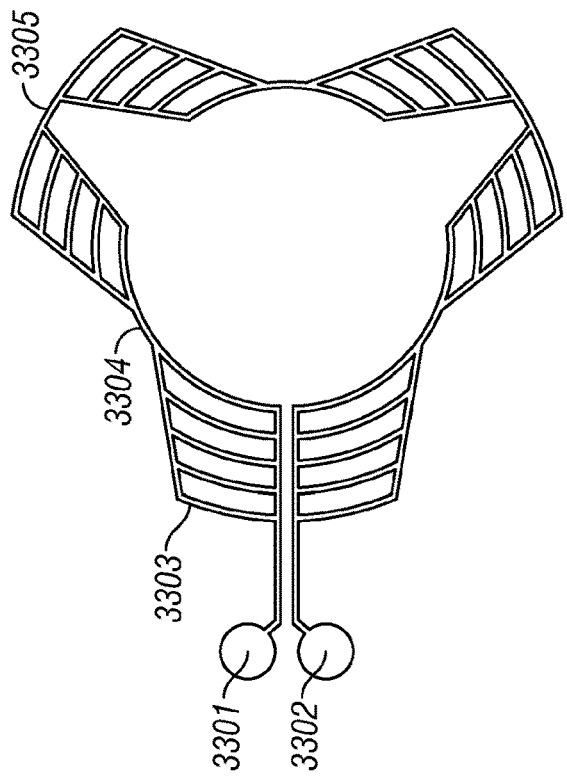

The embodiments shown in FIGS. 33A and 33B provide two different microfluidic configurations for a multiple channel device that allows crosstalk between channels, for example, to allow mixing. In FIG. 33A, fluid is drawn in through an input node (3301), allowed to split into multiple channels (3303), and then forced to recombine as the channels collapse to a single channel (3304) toward the center of the design. A flow is then allowed to split again and recombine at a single channel (3305) toward the outer rim of the design. During operation, the process can be repeated twice more until the fluid exits at 3302. The differences in path length result in longitudinal mixing.

In the embodiment of FIG. 33B, the splitting (3308) and recombination of the flow can occur in the middle of the concentric channel region (3309). Fluid enters at 3306 and exits at 3307.

Figure 34A:
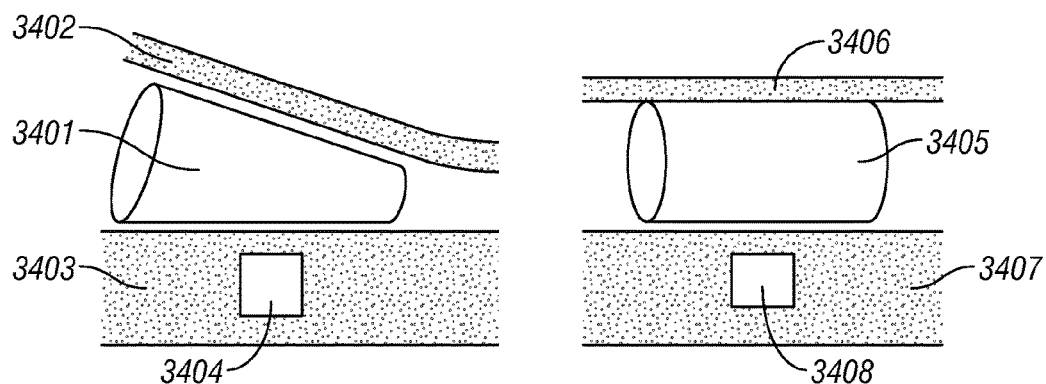
FIGS. 34A and 34B show schematically the use of conical and cylindrical rollers for a rotary pump, according to certain embodiments of the invention.

The embodiment of FIG. 34A shows a schematic of conical (3401) and cylindrical (3405) rollers between two layers of PDMS (3402 and 3403, 3406 and 3407). During operation, these rollers can be depressed so that they compress their respective microfluidic channels (3404 and 3408).

Figure 34B:
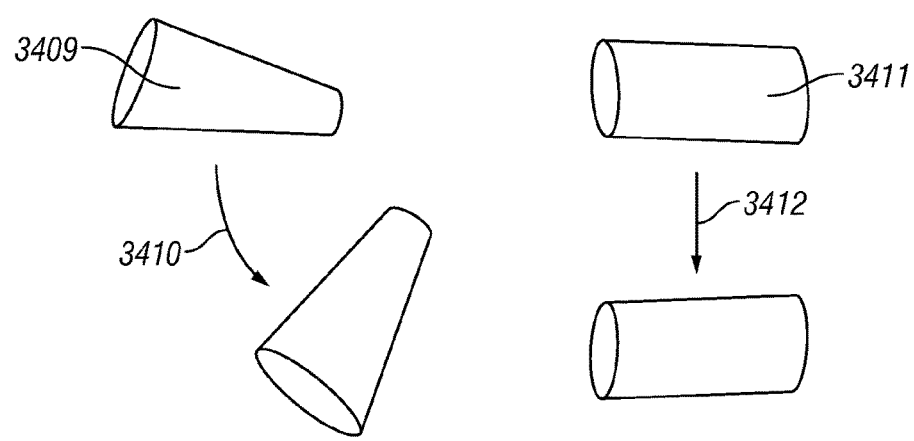

The embodiment shown in FIG. 34B illustrates some of the advantages of using conical rollers for a rotary pump. A conical roller (3409) rolls in a circle (3410) because of the differences in radii at its end points. A thrust bearing using conical rollers also has the advantage of being self-centering when depressed by the coupler and PDMS washer system. On the other hand, cylindrical rollers (3411) roll in a straight line (3412), implying that, when included in a thrust bearing, a restoring force on its outer edge is required for rotary motion, and that there can be differential slippage along the length of the roller if it is forced to roll in a circle.

The embodiments illustrated in FIG. 35 show a variety of cage designs for custom thrust bearings. The physical cage assemblies for the designs are denoted as 3501, 3503, 3506, 3508, and 3511.

The embodiments of FIGS. 35A and 35B show designs that would contain rollers. The equivalently sized and spaced openings (3502) in FIG. 35A would accommodate 20 rollers of equal length, whereas the smaller openings (3505) in FIG. 35B would accommodate shorter rollers in a staggered fashion. Longer rollers (3504) are inserted at regular intervals to push flow along.

FIGS. 35C, 35D, and 35E show embodiments that can contain spherical balls as the rolling elements. FIG. 35C shows an embodiment with a cage configuration for a standard ball thrust bearing, with openings at regular intervals (3507) for balls. The embodiment of FIG. 35D has a staggered configuration of openings (3509), akin to that shown in FIG. 35B. Three openings (3510), spanning from the inner to the outer radius, mimic the flushing action of the longer rollers. FIG. 35E uses the three-ball-span configuration (3512) around the entirety of the cage. Such a bearing has the low friction advantages of a spherical ball but would allow multiple concentric channels to be pumped at similar compression levels.

Figure 36B:
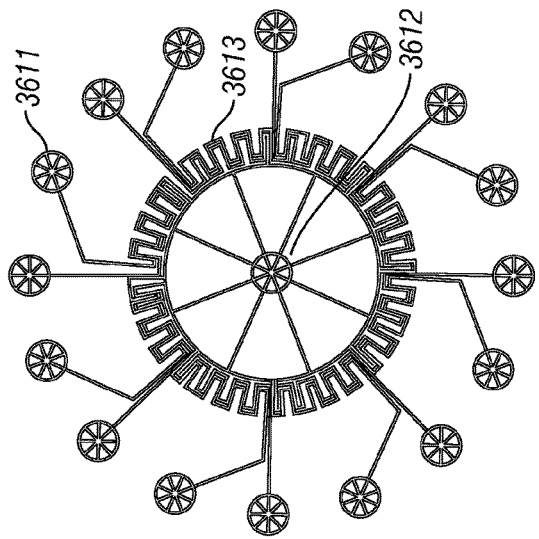
FIGS. 36A-36C illustrate schematically the principle of operation and a diagram of a rotary planar valve (RPV) microvalve, according to one embodiment of the invention.
Figure 36A:
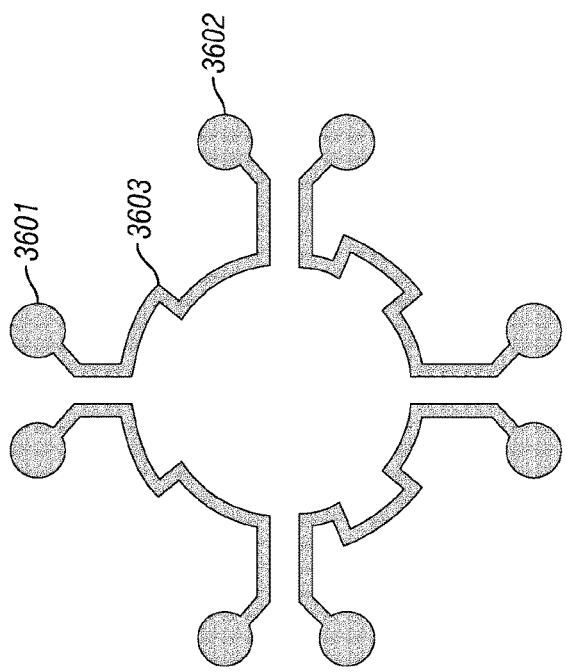
Figure 36C:
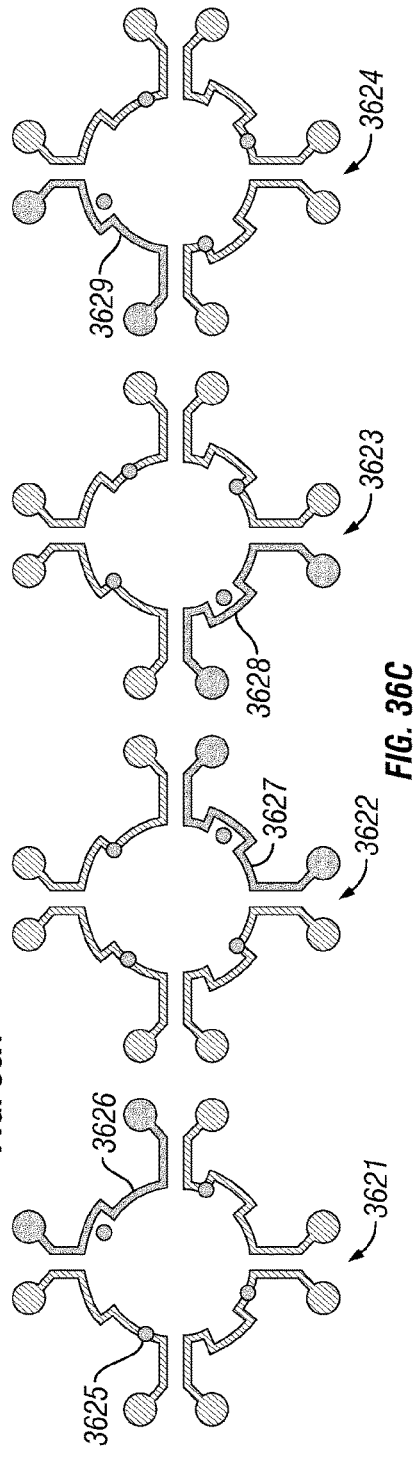

The principle of operation and a diagram of one embodiment of an RPV microvalve are shown in FIGS. 36A-36C. FIG. 36A illustrates a four-channel valve in which the fluidic connections between inputs (3601) and outputs (3602) are interrupted by compression from the ball in the bearing at certain locations and contiguous at other locations (3603) such that only one channel of the valve's four channels is open at any given rolling element position. The principle of operation is illustrated in FIG. 36C with four rolling elements (3625) shown in four different positions (3621-3624) in which only one channel (3626-3629, respectively) is open to flow between the inputs and outputs. FIG. 36B is a schematic drawing of a 16-port valve in which the outputs from 16 switched inputs (3611) are combined at a single point in the center (3612). The meandering channels (3613) crisscross the radial position of the rolling element compression zone and are precisely positioned such that at each of sixteen angular positions of 8 rolling elements, only one input channel is open to the output and the remaining channels are compressed by one or more rolling elements, forming a 16-port valve.

Figure 37A:
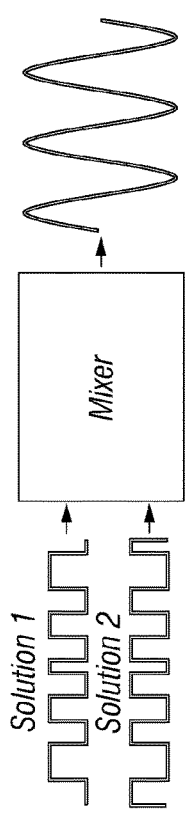
FIGS. 37A-37C show schematically the concept, design, and functioning of a pulse-width modulation RPV waveform generator, according to one embodiment of the invention.
Figure 37B:
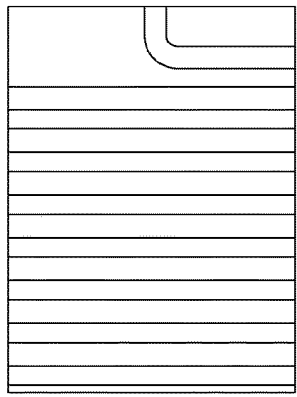
Figure 37C:
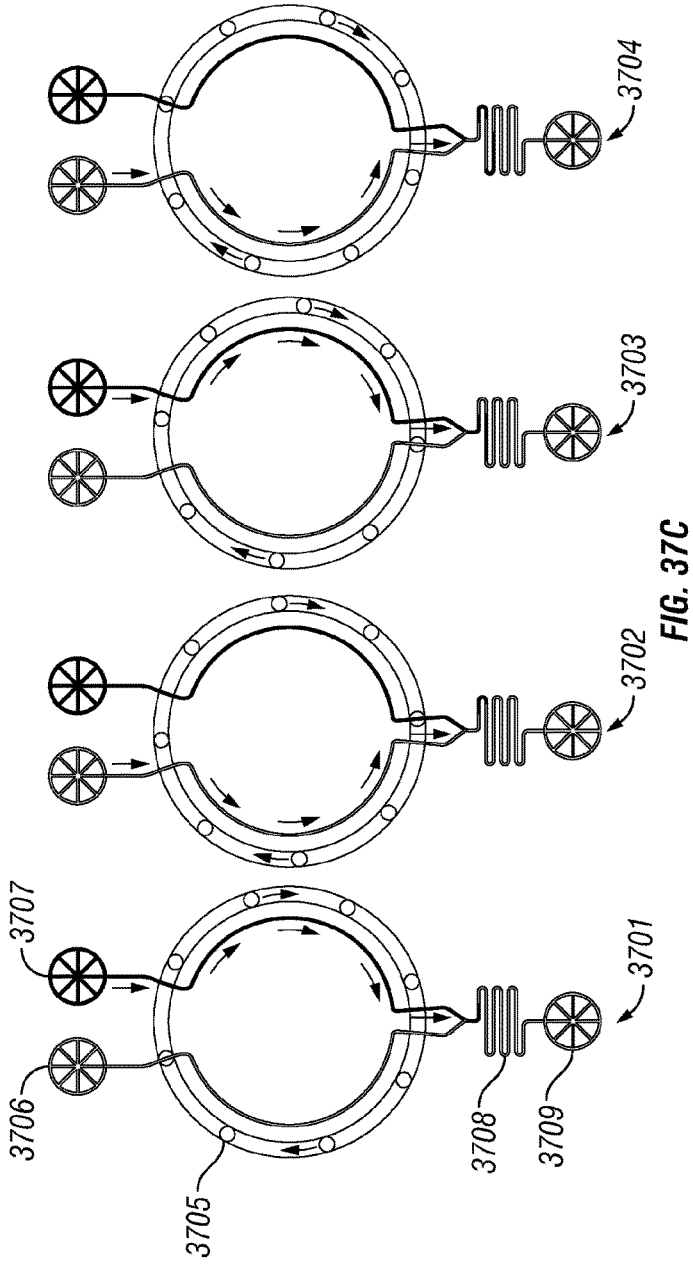

FIGS. 37A-37C show the concept, design, and functioning of one embodiment of a pulse-width modulation RPV waveform generator. FIG. 37A illustrates how the generator is composed of a continuous mixer that uses alternating discrete pulses of two solutions as inputs. The boluses mix together in a meander by diffusion and Taylor dispersion, forming an axial output concentration waveform. By dynamically changing the length of the discrete pulses, multiple different concentration waveforms can be produced at a wide range of temporal resolution. FIG. 37B is an image of an axial gradient in a meander produced by manually alternating between DI water and black dye. FIG. 37C is a schematic of the implementation of discrete bolus mixing of two solutions using RPVs. As the compression zones of the rolling elements (3705) rotate, the two channels (3706, 3707) are alternately closed. Positions 3701, 3702, 3703, and 3704 show the four different states of the device formed by 11.25 degree clockwise rotation of the rolling elements (3705). In positions 3701 and 3703, 3706 is closed, allowing fluid from 3707 to enter the meander (3708). In positions 3702 and 3704, 3707 is closed, allowing fluid to enter from 3706. The discrete boluses of the two solutions mix in the meander (3708) and exit through the output port (3709). By dynamically varying the speed of the motor, arbitrary bolus sizes can be created, allowing generation of different waveforms.

FIGS. 38A-38D illustrate the design and operation of a variable flow rate RPPM. FIG. 38A illustrates a device that pumps two fluids through two separate channels (3807, 3808) from respective fluid inputs (3801, 3803) to fluid outputs (3802, 3804), using two rolling elements (3805, 3806) rotating at constant speed around a central axis and positioned opposite each other such that each fluid channel is always compressed by exactly one bearing. FIGS. 38B-38D illustrate device operation, as the rolling element (3812) traverses the fluid channels (3811, 3821, 3831) and encounters an increasing number of channels as it progresses from FIGS. 38B-38D. As the number of channels that rolling element (3812) compresses changes, pumping speed through the fluid channel changes proportionally, such that any flow waveform can be created with a specific variation in channel multiplicity.

FIGS. 39A-D illustrate a pulse regulating device with an input (3905) and an output (3906). As shown in FIG. 39A, when the standard device (3901) is operated, there is a period where the rolling element (3902) occludes the channels as they exit the device, which causes a stoppage in flow (3903). This in turn causes the flow from the device (3901) to be pulsatile. However, the pulse regulator design shown in FIG. 39B phases the channels out at different stages of rotation (3904), decreasing the pulsatility of flow from input (3905) to output (3906). A detailed view of the phased exits is shown in FIGS. 39C-39D. As shown in FIG. 39C, the rolling element (3902) is early in the cycle, and is occluding the exit of the third channel (3909) while the others remain open and allow flow. FIG. 39D shows the rolling element (3902) late in the cycle of rotation, labeled as 3910 occluding the exit of the last channel (3911).

Figure 40A:
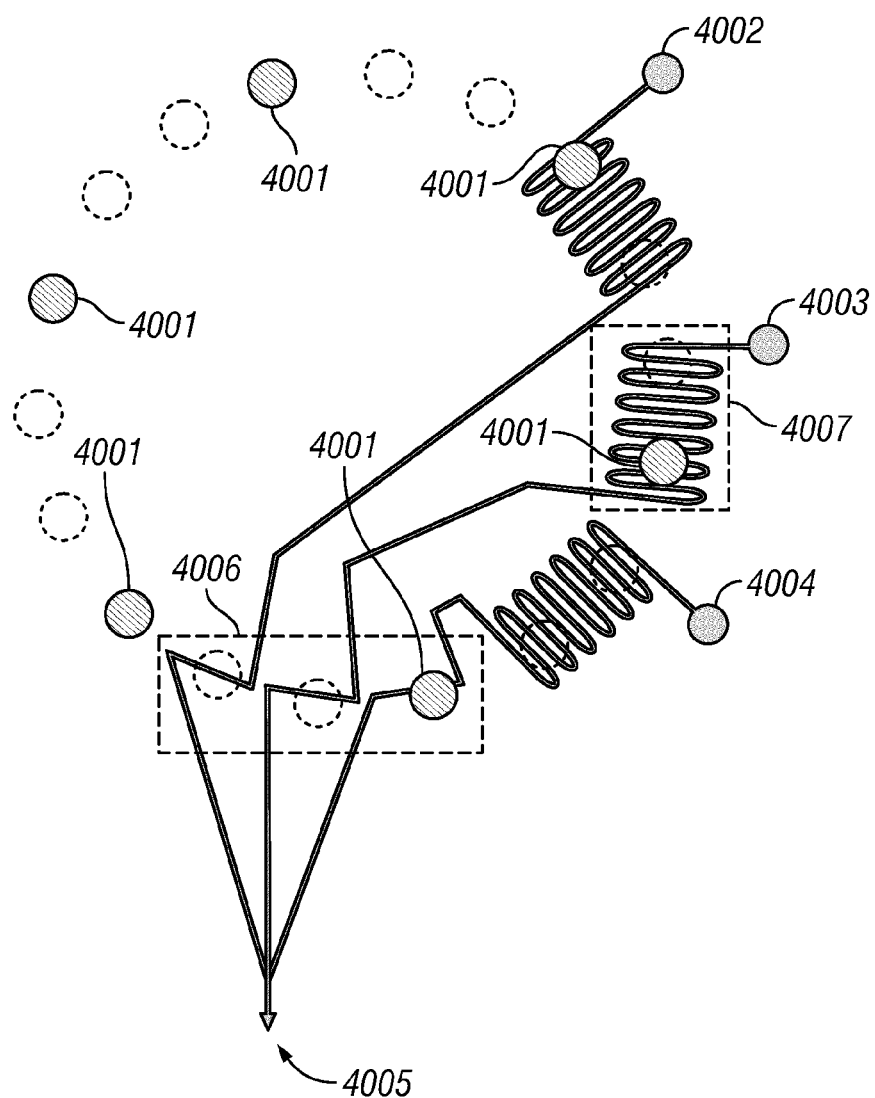
FIG. 40A shows schematically an RPPM configured as a two- or three-phase droplet generator, according to one embodiment of the invention.

FIG. 40A illustrates an RPPM configured as a two- or three-phase droplet generator. During operation, the actuator with six rolling elements (4001) (shown filled with hatch marks) rotates in a clockwise direction. The compression zones for each of the six rolling elements move continuously around the radius defined by the bearing geometry. Three compression zones for each rolling element (eighteen total) are depicted as unfilled circles. Three microfluidic channels with inputs (4002-4004) follow precise pathways through the bearing compression zones and converge at a single output (4005). Fluid can be pumped from the inputs of all three channels to the output in the pumping zone (4006) in reverse sequential order (4004, then 4003, then 4002).

During operation, each channel is occluded to prevent backflow with meanders in the compression zones of non-pumping rolling elements (4007). The positioning of the compression zones ensures that the channel being pumped in the pumping zone is not occluded, while the other two channels are occluded. This can ensure forward flow at the nexus and an interleaving of fluids from the three input channels. If immiscible liquids are used on the inputs, droplets can be formed on the outputs. Two-phase droplet mixtures can be obtained by eliminating one of the three microfluidic channels, and if desired, enlarging the remaining two to maintain continuous, uninterrupted flow. If more than three fluidic phases or solutions are desired, additional channels may be added in a similar configuration.

FIG. 40B illustrates an RPPM and RPV system that can act as both a fluid multiplexer and a demultiplexer, depending upon the direction of rotation. This extends the concept shown in FIG. 40A and demonstrates the use of a single set of ball actuators to work as both a pump and a valve. With the balls rotating in a clockwise direction, the device acts as a multiplexer and draws fluid from three inputs and expels it through a single output. Fluid is first drawn from port 4011, with the pumping section 4014 providing the pressure to move the fluid, in contrast with the device in FIG. 40A where an external pressure source is required. The return path 4016 allows the fluid to flow through to the output 4017 by crossing the path of the balls at a location where the flow is not blocked by a ball when that section is pumping. After the ball moves from position A to position C, the pumping from 4011 stops because the ball (shaded) encounters the blocking valve section 4015. Fluid is pumped from input 4012 when another ball reaches position B, and continues until that ball passes position A. Fluid is pumped from input 4013 when another ball reaches position C, and continues until that ball passes position B. The output 4017 contains the summed flow from 4011, 4012, and 4013, as shown in FIG. 40C. The exact timing of the beginning and end of each pumping phase is determined by the exact angular position of the pumping and blocking valve regions, and can be adjusted as desired in the design of the device. Hence, in this configuration, three different solutions can be multiplexed from the three inputs into a common output. Similarly, rotation of the balls in a counterclockwise direction causes the device to act as a demultiplexer that draws fluid from a single input 4017 and expels it through three separate outputs 4011-4013. Other embodiments could produce multiplexers and demultiplexers with different numbers of solutions and different timing.

FIG. 41A shows a profile view of one embodiment of a peristalsis system in microfluidics. The microfluidic channel (4101) is compressed by a rolling element (4102) (e.g., a ball bearing in certain embodiments) that is receiving downward force applied by a brass flange (4103) and a PDMS washer (4104). As rolling element (4102) rotates and moves along the microfluidic channel, the fluid or contents of the channel also move along. FIG. 41B shows two schematics of embodiments of the RPPM. In the upper schematic, a single channel design depicts input and output punch pads (4111, 4112). Rolling elements (4113) show theoretical placement of the balls within a thrust bearing. The lower schematic of FIG. 39B replaces a single channel configuration with five concentric channels (4114) that combine on ends. FIG. 41C is an exploded profile view of one embodiment of an RPPM system. In this particular embodiment, a stepper motor (4121) is attached to a polycarbonate base piece (4122) by a set of four M3 screws (4123), and a brass flange (4124) is attached to the motor shaft by a 0-80 screw (4125). In the embodiment shown, the brass flange's shaft provides alignment and support for the PDMS washer (4126) and thrust bearing (4127). The microfluidic pump (4128) with tubing (4129) is placed between the thrust bearing and polycarbonate piece. FIG. 41D is a assembled version of FIG. 41C, while FIG. 41E shows a perspective view.

Figure 42B:
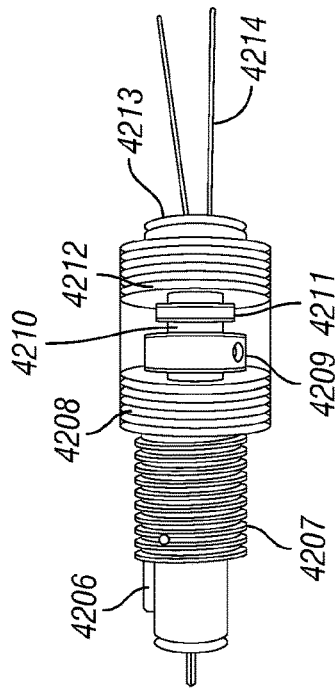
FIGS. 42A-42B show schematically a compact RPPM and its physical implementation, respectively, according to one embodiment of the invention.
Figure 42D:
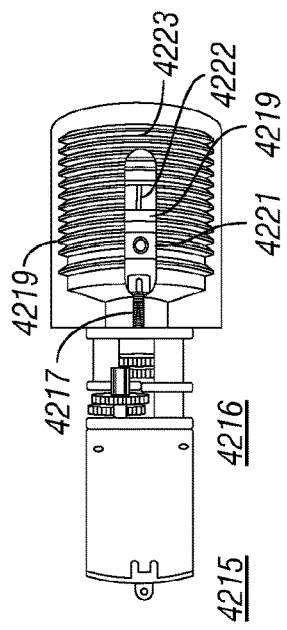
FIGS. 42C-42D show schematically the unassembled parts of an RPPM and the assembled device, respectively, according to another embodiment of the invention.
Figure 42A:
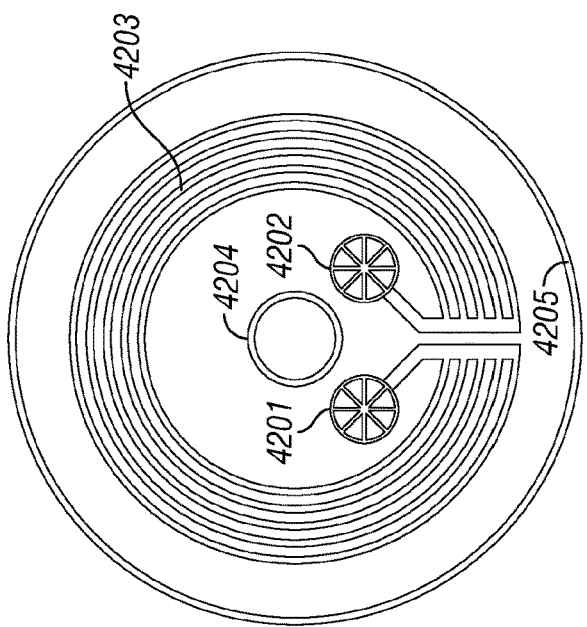

FIG. 42A shows a schematic for a compact embodiment of an RPPM. 4201 and 4202 are the input/output ports for this design, which are connected to 5 concentric channels (4203). Additional concentric circles (4204, 4205) are included for alignment. FIG. 42B shows the physical implementation of the compact embodiment illustrated in FIG. 42A. This implementation includes a small stepper motor (4206), which is enclosed in a hollow threaded rod (4207, secured to the motor housing with a set screw) and is screwed into the top half of a partially threaded hollow sleeve (4208). A brass flange (4209, secured to the motor shaft with a set screw), allows a PDMS washer (4210) and ball thrust bearing (4211) to be placed concentric to the motor's axis of rotation. The PDMS microfluidic device (4212) is placed on top of another hollow threaded rod (4213), which is then screwed into the bottom half of 4208. Tubing (4214) can then be added to facilitate fluid flow. Threaded rod (4213) provides structural support and height adjustment to microfluidic device (4212). Both threaded rods (4213) and (4207) can be used to control the amount of compression between the thrust bearing (4211) and PDMS microfluidic device (4212), which is a major factor in controlling flow.

Figure 42C:
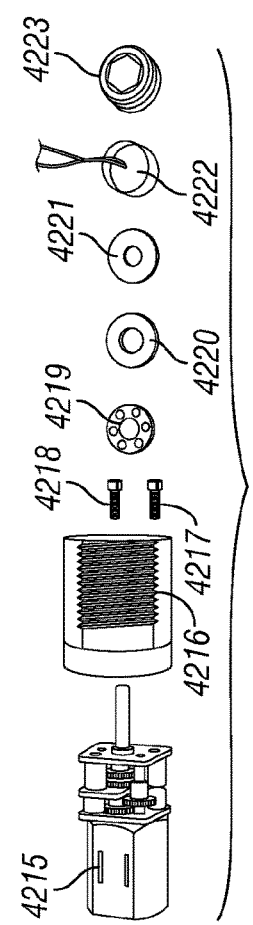

FIG. 42C shows the unassembled parts used in another implementation of the embodiment shown in FIG. 42A. In this embodiment, a motor (4215) is directly attached to an acrylic housing (4216) with two hex socket head screws (4217, 4218). A brass adapter (4221) is attached to the shaft of the motor with a set screw and supports the PDMS washer (4220) and thrust bearings (4219). In this embodiment, the microfluidic device and tubes (4222) are presented to the bearings and held in place by a hollow set screw (4223). FIG. 42D shows the assembled device, including 4215-4223.

FIGS. 43A-C show a design for a multi-pump array. This embodiment includes three pairs of two pumps (4301 and 4302, 4303 and 4304, 4305 and 4306), each of which is run through serpentine mixers (4307-4309). The middle pair is also run through a meander (4310) to allow for contemporaneous flow. In this embodiment, the three channels are then combined in a fourth serpentine mixer (4311). Parts of the larger structure (FIG. 43C) are shown with dotted lines. These include screws (4312), motor heads (4313), and fastening plates (4314). FIG. 43B shows the motor used in the array (4315). FIG. 43C shows a 3-D cutaway model of the array, which shows the motor for the array (4315), the fastening plates (4316), brass adapters (4317), PDMS washers (4318), thrust bearings (4319), PDMS device layer (4320), glass base (4321), and metal base (4322). The fastening plates are supported by springs from underneath and held down by adjustable screws.

Figure 44:
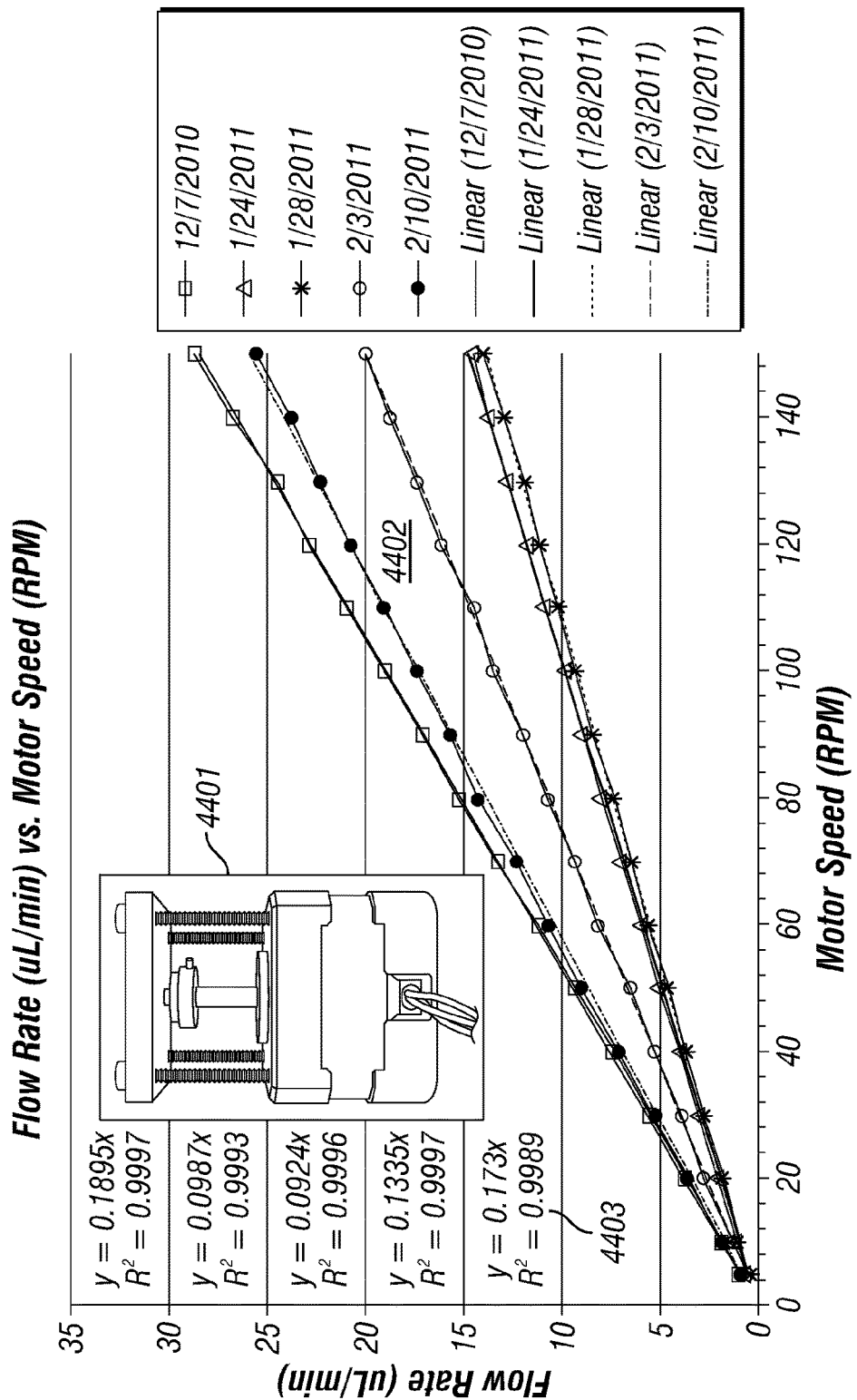
FIG. 44 presents the linear relationship between flow rate and motor speed exhibited by one embodiment of the invention.

FIG. 44 shows the excellent linear relationship between flow rate (microliters/minute) and motor speed (revolutions/minute) exhibited by one embodiment of an RPPM. 4401 shows a schematic of the pump used to gather this data. Each set of points (4402) (e.g., square, triangle, asterisk, open circle, and closed circle data points, as shown from top to bottom in the legend) has a linear trendline fitted to it. The equations and $R^2$ values for these trendlines (4403) are shown on the left-hand side of the graph.

Figure 45A:
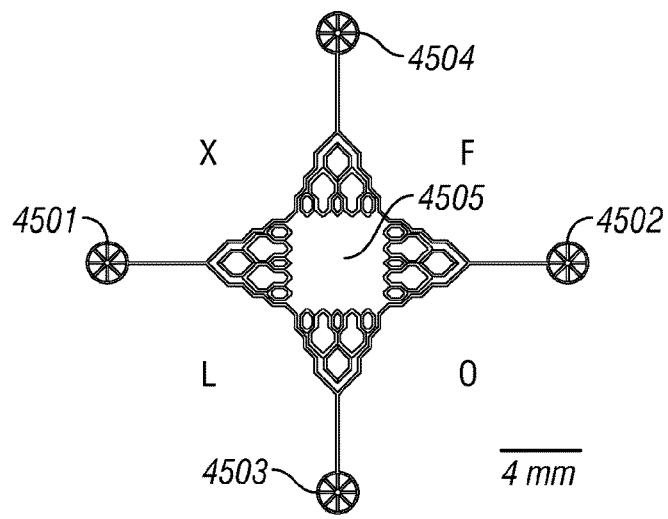
FIGS. 45A-45C show schematically and with kymographs how two RPPMs may be arranged to provide two-dimensional control of particles in a microfluidic device, according to one embodiment of the invention.
Figure 45B:
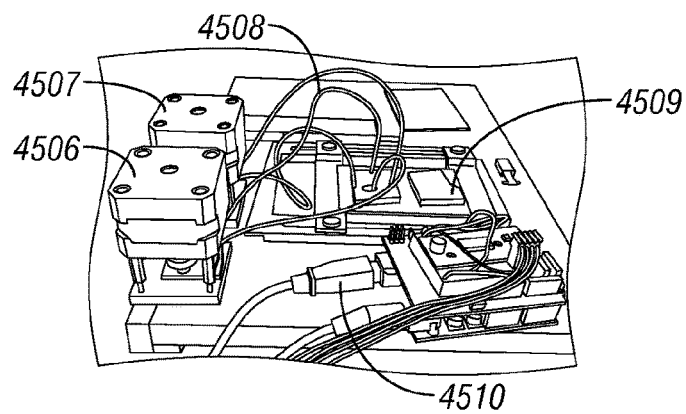
Figure 45C:
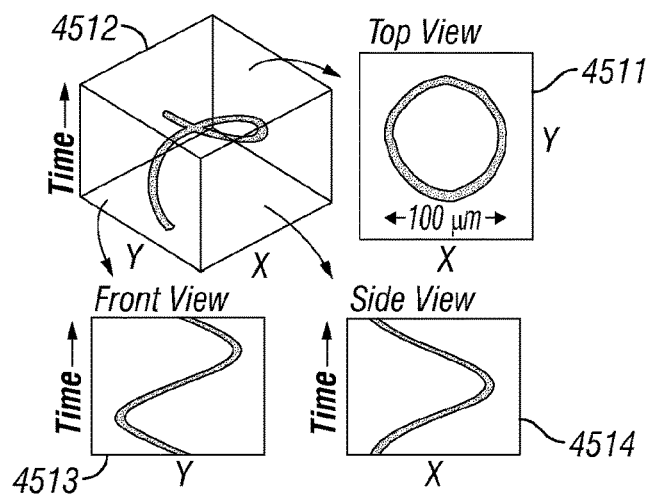

FIGS. 45A-45C show an embodiment exhibiting how two RPPMs may be arranged to provide two-dimensional control of particles in a microfluidic device. FIG. 45A shows a schematic for the microfluidic device (known as a "crossflow" divide) used in 2-D control. One input and one output of the first pump are connected via tubing to ports (4501) and (4502), respectively. The second pump's input and output are connected to ports (4503) and (4504). The open chamber (4505) in the middle of the device allows particles to move freely based on the flow streams provided by the two RPPMs.

FIG. 45B shows the crossflow device and two RPPMs (4506 and 4507) configured to perform a 2-D control experiment. Tubing (4508) connects the two pumps to the crossflow device (4509). The microcontroller platform used to control this pump system (4510) is also shown. FIG. 45C shows several kymographs created using this 2-D crossflow setup. By setting each RPPM to provide a sinusoidal input stimulus (with a 90 degree phase shift between the two), particles can be moved in a circle, as shown in 4511. The 3-D graph (4512) shows the path of the particle in the x- and y-axis and the progression of time in the z-axis. 4513 and 4514 show 2-D side views taken from the 3-D kymograph.

FIGS. 46A-46C illustrate the design and operation of one embodiment of an RPPM- and RPV-driven batch mode microformulator. In this embodiment, fluid inputs are selected from inputs (4601) of a rotary multiplexer (4602) and are drawn with an RPPM (4605) into a loading shuttle (4603) that holds inputs while RPPM (4605) flushes rotary multiplexer (4602) with solvent to the waste port (4606). Inputs in loading shuttle (4603) are then drawn into the mixing chamber (4604) and recirculated with RPPM (4605) until sufficiently mixed, at which point they are pumped out with RPPM (4605) through the output port (4607). In this exemplary embodiment, mode switching of the device is achieved with an RPV (4608) that sequentially opens and closes channel paths with a thrust bearing located in the compression zone (4609). FIGS. 46B and 46C illustrate RPV operation, as rolling elements (4611, 4612, 4621, 4622) sequentially pass over compression zones (4613, 4623) of fluid channels (4614, 4615, 4624, 4625) and successively open and close channel paths to switch between device operation modes.

Figure 47:
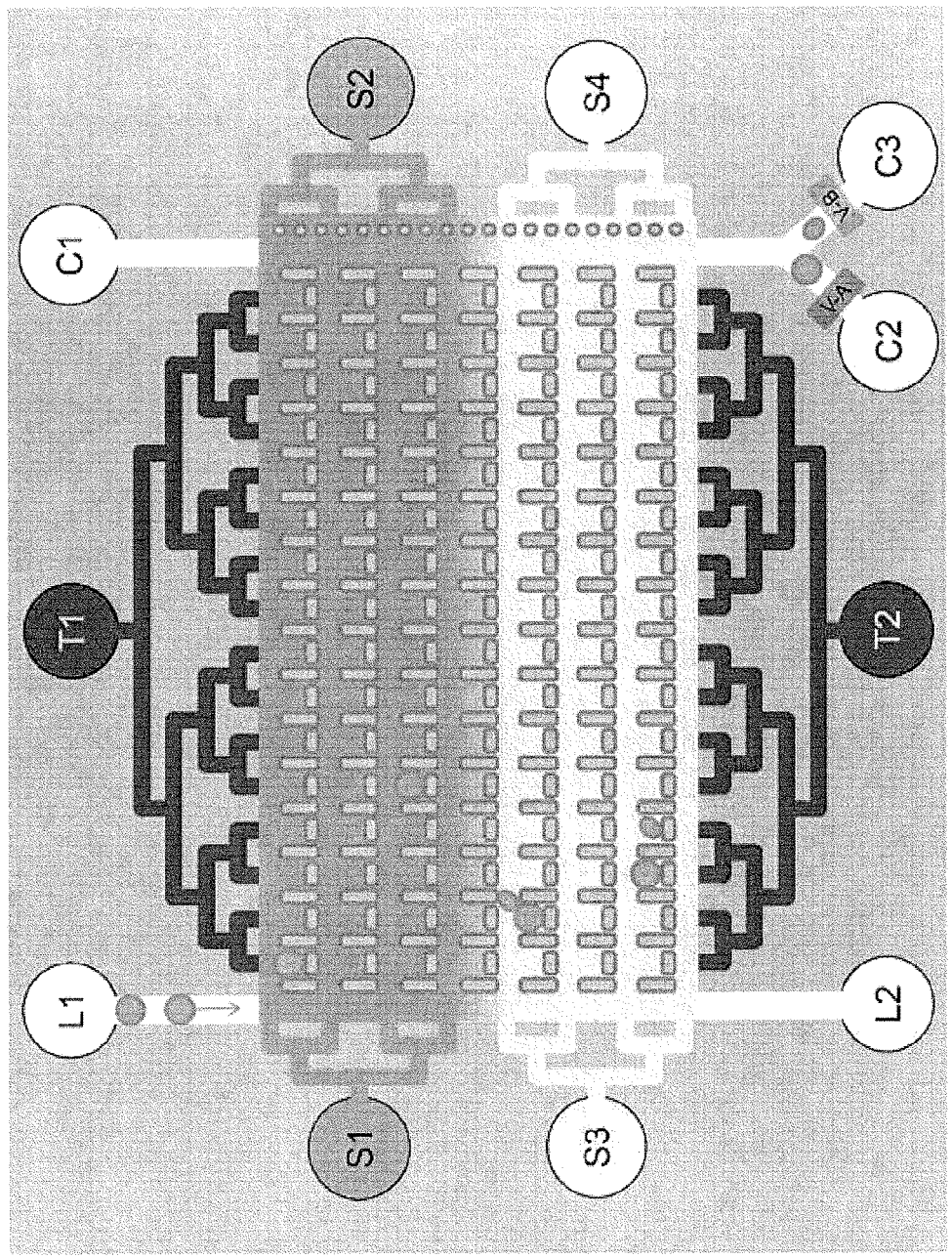
FIG. 47 illustrates schematically a high-density array of microfluidic single-cell yeast traps, according to one embodiment of the invention.

FIG. 47 is a schematic representation of an alternative embodiment of a high-density array of microfluidic single-cell yeast traps. In this schematic, 112 traps are shown in 7 rows of 16. In this exemplary embodiment, each trap is 10 μm×10 μm, and the channel above each trap is 10 μm wide. The ports are configured as pairs connected to a push-pull pump, using an on-chip peristaltic pump with either pneumatic or rotary mechanical actuation or a syringe pump pair, so that the flow from one port is matched by the fluid removed from the other port of the pair. In one exemplary method of use, a small number of yeast cells can be loaded by laminar flow along L1-L2 while all other ports are blocked. Once the yeast cells are loaded in a line along the left edge of the array, pumps S1-S2 and S3-S4 are actuated transiently to move these cells from left to right into the array.

In this embodiment, actuation of the transverse parallel flow from T1 to T2 will sweep the cells into the nearest trap. Adjustment of the T1-T2 transverse flow can control the ability of the device to hold cells in the traps, or modulate the trapping efficiency. S1-S2 and S3-S4 can pump different media formulations, e.g., different glucose concentrations. A gradient generator could be used to provide a different concentration for each row. In this schematic, there are four adult yeast cells trapped, one of which is budding, and another whose bud has already moved to the adjacent downstream trap.

In the embodiment shown, adjustment of the pumping rates of S1-S2 and S3-S4 relative to T1-T2 can lead to cells being trapped or swept all the way to the right, where a vertical fence of small posts detains the cells. Then optical sensing and computer-controlled valves V-A and V-B can direct flow from C1 cells to either outlet ports C2 or C3, depending upon the cell type or genealogy. More outlet ports can be used to sort into more categories. Adequate perfusion for low-density cultures can be readily maintained with total flow through S1-S2 and S3-S4 of only 2 mL/min. Activation of T1-T2 can provide perfusion without translation. Alternatively, flow from S1 to S2 and S3 to S4 will shift to the right cells displaced from a trap by division. At 20× magnification, a typical automated fluorescence microscope can, in 40 ms, image a 430 μm×345 μm field of view (FoV, each) in four colors with 0.3 μm×0.3 μm pixels. By sequentially imaging 12 fields of view in 10 seconds, the high-speed translation of an automated microscope can allow a user to image 4000 traps over a 1.3 mm×1.4 mm area in 10 seconds. The imaged area can either be configured as one large trap array, or multiple, individually controllable trap sub-arrays. One advantage of the latter is that vertical perfusion can be continuous for all traps, but horizontal flow could be limited to the interval where each sub-region is being viewed multiple times by the microscope to track the cells as they move.

FIGS. 48A-F illustrate steps towards implementation of the embodiment of FIG. 47. FIG. 48A illustrates an overall schematic of the device, while FIGS. 48B-48F provide more detailed views of different sections. While the figures in the present disclosure are generally not to scale, FIGS. 48A-48E are shown to scale for one exemplary embodiment. In FIG. 48A, the scale bar represents 1 cm. In FIG. 48B, fluid flow is driven by an on-chip RPPM, and the scale bar is equal to 500 μm. In FIG. 48C, a Moire interference pattern for accurate low-cost mask alignment is illustrated, with a scale bar equal to 400 μm. In FIG. 48D, a valve system that allows integrated cell sorting is shown. In this figure, the scale bar equals 800 μm. In FIG. 48E, an array of cell trap devices is illustrated with a scale bar equal to 60 μm. FIG. 48F illustrates a Comsol hydrodynamic model of cell retention force under perfusion in a selection of trap designs. Surface shading represents fluid velocity magnitude, and vector arrows represent normalized average total shear stress on primary trapped cells (top row) and secondary trapped cells (bottom row).

Figure 49A:
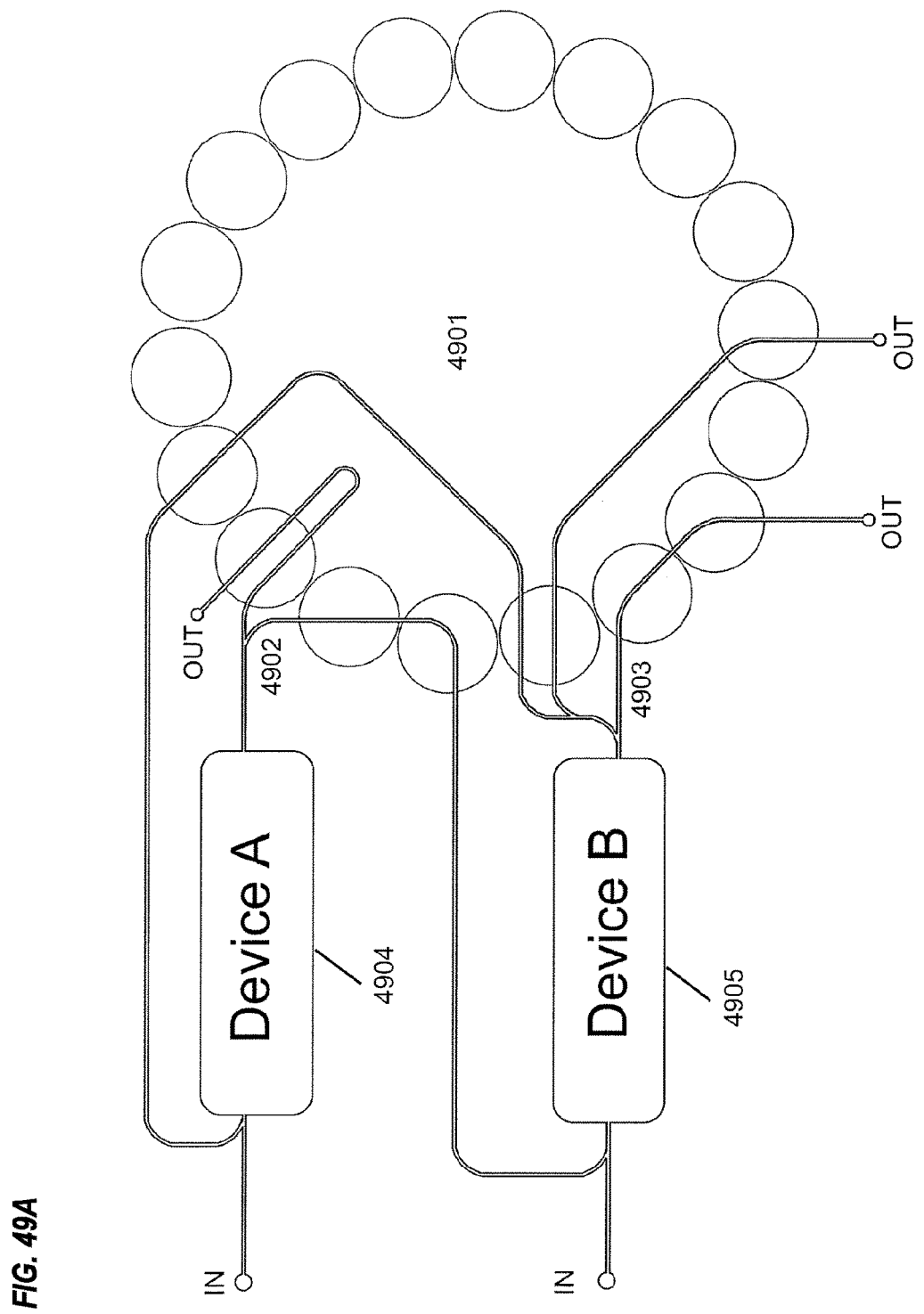
FIG. 49A shows schematically the utilization of rotary thrust ball bearings as planar valves to drive serial switching between three different flow configurations, according to one embodiment of the invention.

FIG. 49A shows an embodiment utilizing rotary thrust ball bearings as planar valves to drive serial switching between three different flow configurations. In this embodiment, rolling element spacing within the cage (4901) allows for three unique positions. Rolling element spacing can be modified to allow for more configurations. Additionally, this configuration of nanobioreactor and channel positioning can be arrayed around the cage to control multiple switching events in a single rotation. A compression between the rolling element-PDMS interface forces any underlying microfluidic flow channels shut. Rotation of the bearing cage allows for only one open flow path at branch sites (4902, 4903) so that nanobioreactor A and B (4904, 4905) can operate separately, as shown in FIG. 49B, or in series, as shown in FIGS. 49C-49D.

Figure 49B:
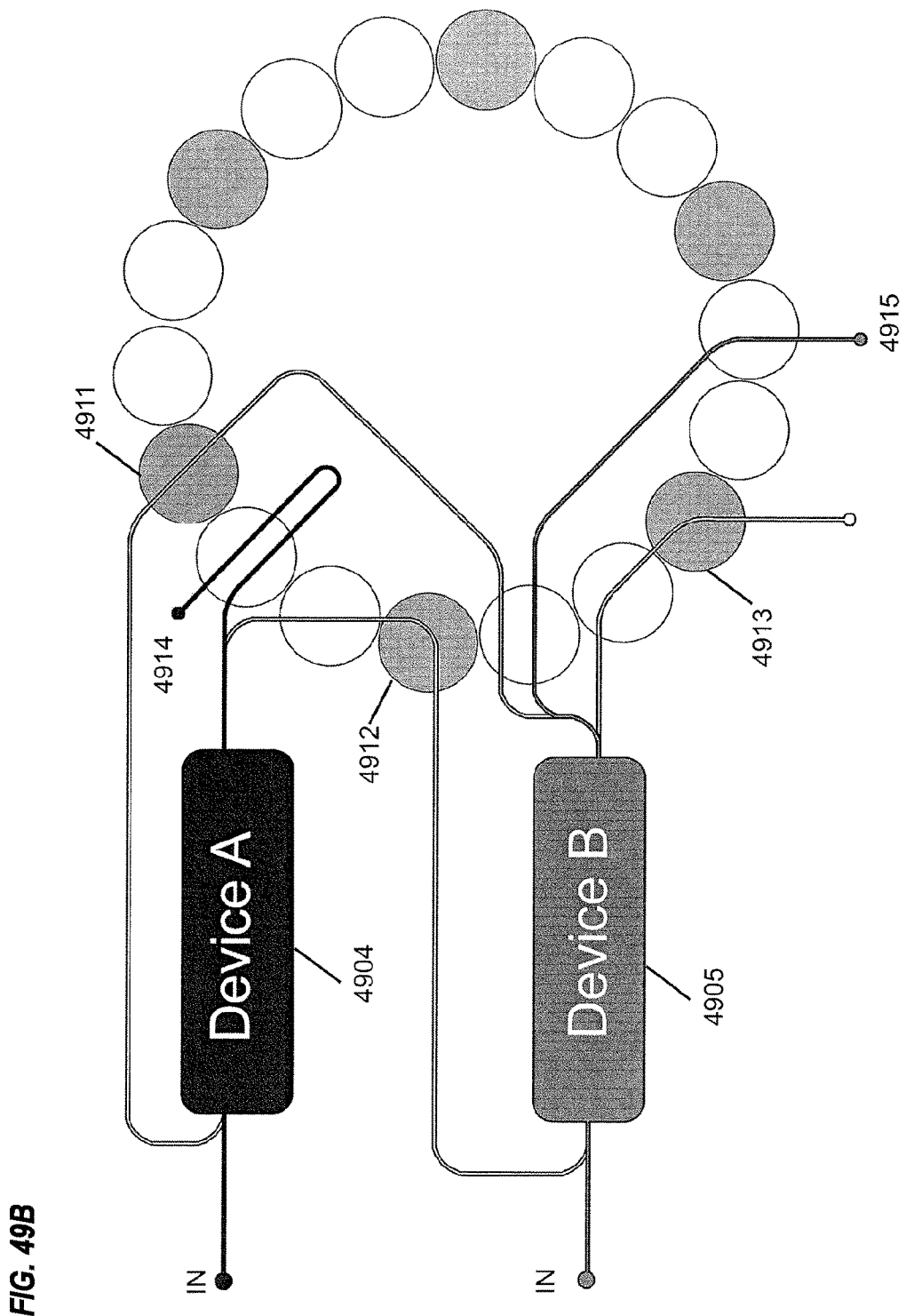
FIG. 49B shows schematically a rolling element configuration that allows independent perfusion of the nanobioreactors in FIG. 49A, according to one embodiment of the invention.

FIG. 49B shows a rolling element (e.g., ball bearing) configuration that allows for independent perfusion of nanobioreactor A and B (4904, 4905). These unique rolling element positions close off channels that connect flow between the nanobioreactors (4911, 4912) and the outlet port used while operating in series from nanobioreactor A to B (4913). Thus, this rotation state leaves only two open outlets (4914, 4915) for independent perfusion of nanobioreactor A and nanobioreactor B.

Figure 49C:
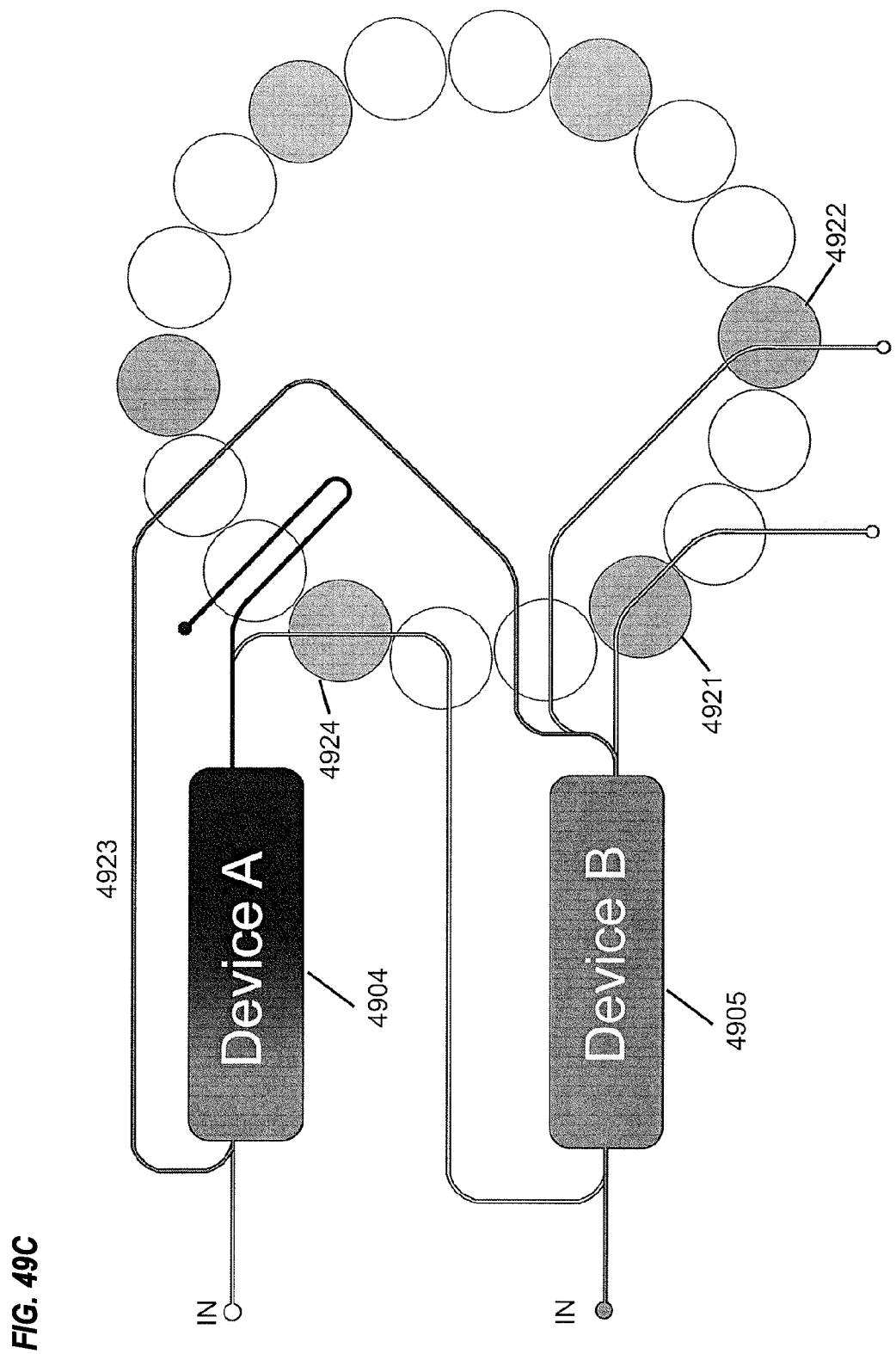
FIGS. 49C-49D show schematically the subsequent clockwise rotation of the rolling element cage of the embodiment shown in FIG. 49B to the next and last unique states, respectively.

Subsequent clockwise rotation of the rolling element cage to the next unique state is shown in FIG. 49C. Rolling element positions (4921, 4922) close output flow channels for nanobioreactor B and re-route output flow of B to nanobioreactor A (4923). Flow from nanobioreactor A to B is occluded as well (4924), forcing flow to a single output channel (4914).

Figure 49D:
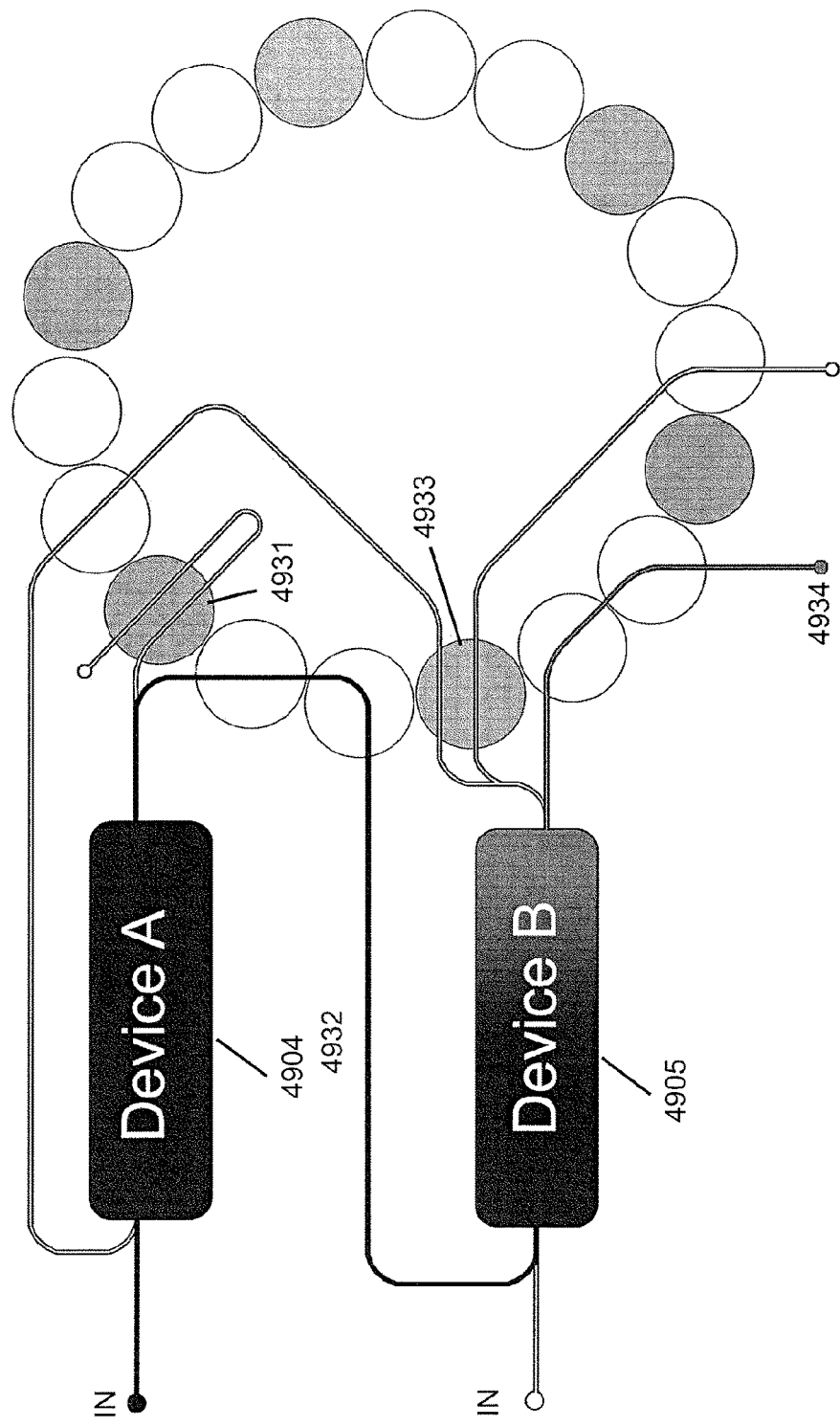

Further clockwise rotation of the rolling element cage to the last unique state is shown in FIG. 49D. Rolling element position (4931) blocks the outlet port downstream of nanobioreactor A, forcing flow through a connecting channel (4932) from A to nanobioreactor B. Series flow from nanobioreactor B to A is prevented as this channel (4932) is forced shut due to ball bearing compression (4933). Additionally, a single outlet port (4934) remains open as ball bearing (4932) shuts flow to the second outlet port of nanobioreactor B (4915).

Figure 50:
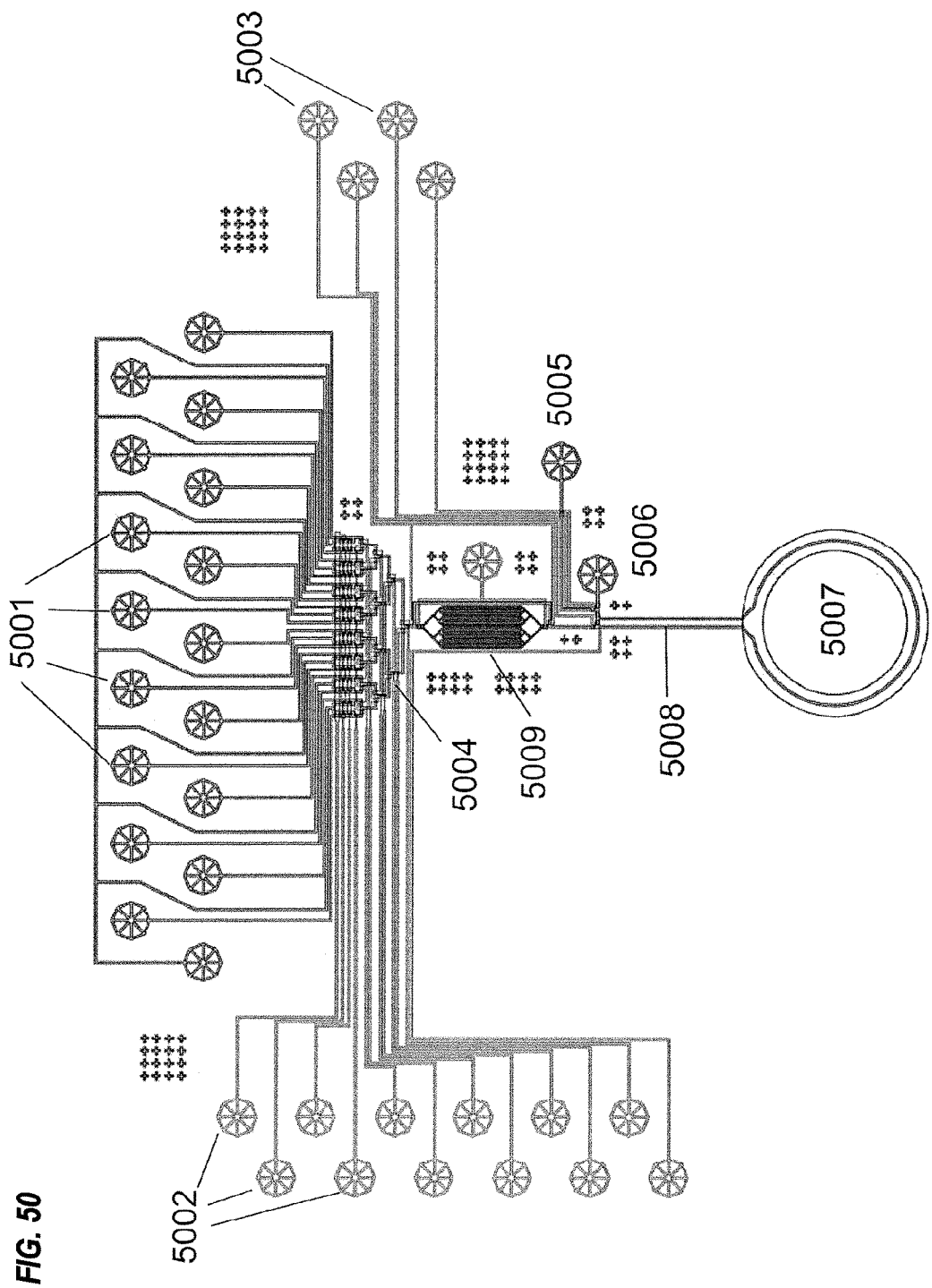
FIG. 50 illustrates schematically the design of an RPPM-driven and Quake-style valve-controlled batch mode microformulator, according to one embodiment of the invention.

FIG. 50 illustrates the design of an RPPM-driven and Quake-style valve-controlled batch mode microformulator. Fluid inputs are selected from inputs (5001) of a multiplexer (5004) controlled with Quake valve channels (5002) and are drawn with an RPPM (5007) into a loading shuttle (5009) that holds inputs while 5001 is flushed with solvent to the waste port (5005). Inputs in 5004 are then drawn with 5007 into the mixing chamber (5008) and recirculated with 5007 until sufficiently mixed, at which point they are pumped out with 5007 through the output port (5006). Mode switching is achieved with Quake valve channels (5003) that sequentially open and close channel paths.

FIG. 51 shows the concept, design, and operation of a Quantum Dot Hybridizer. FIG. 51A is a schematic showing the agglomeration of quantum dots (QDs) and antigens in a closed recirculating microfluidic channel. With each hybridization cycle, the agglomerates grow larger until they can be easily detected. FIG. 51B is a schematic showing how an RPPM and pneumatic valves are combined to implement re-circulatory flow. The device consists of connected flow channels (5104) and three control channels that act as valves (5101, 5102, 5108). When 5101 and 5108 are pressurized, the fluidic inputs (5103) are closed, allowing for circulation of fluid by rotation of the RPPM's bearings (5105). When only 5102 is pressurized, fluid can enter and exit the system through the fluid ports (5103). The branched mixer (5107), which is composed of multiple meanders of varied lengths (5106), allows for rapid mixing.

Figure 51B:
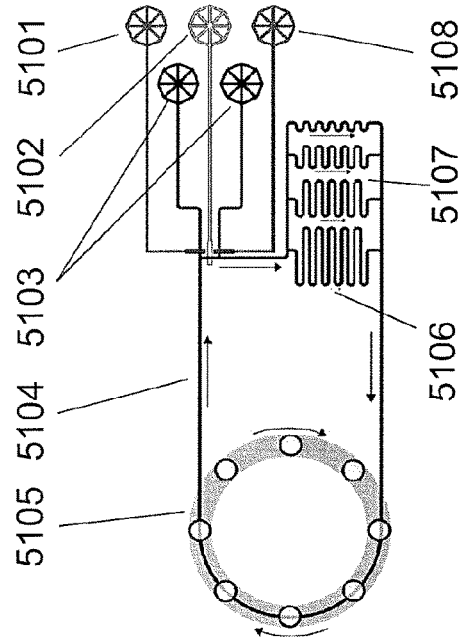
FIGS. 51A-51D show schematically and in images the concept, design, and operation of a Quantum Dot Hybridzer, according to one embodiment of the invention.
Figure 51D:
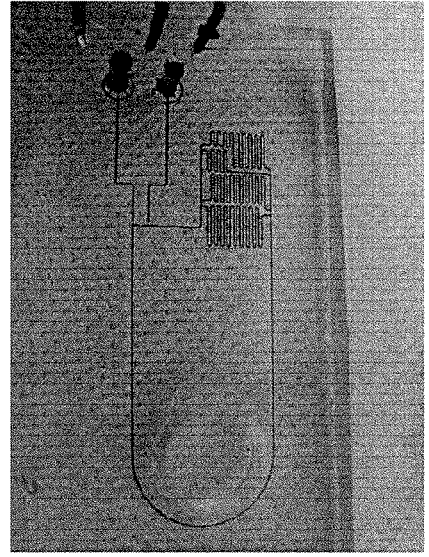
Figure 51A:
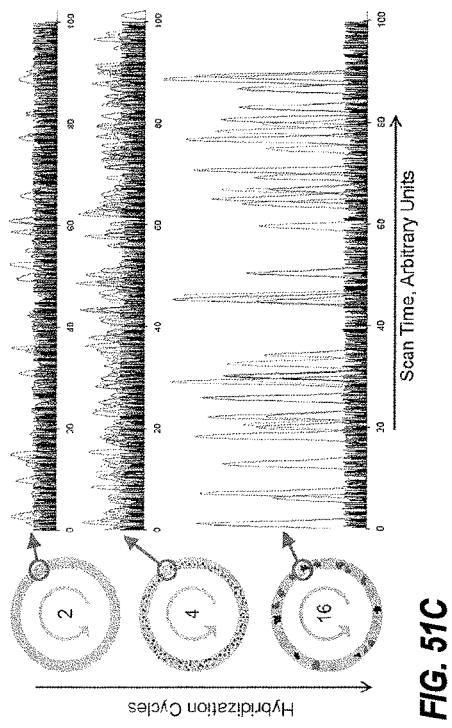
Figure 51C:
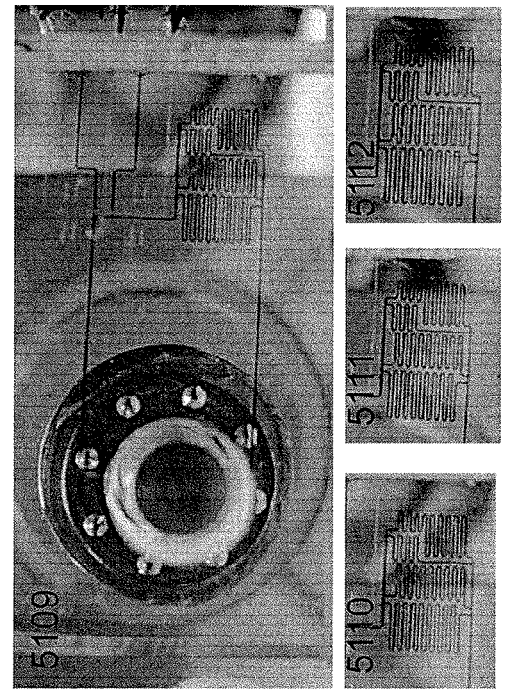

FIG. 51C shows the device (5109) with the motor and rolling elements set up to re-circulate and mix lighter and darker dyes (with the darker dyes being at the upper portions of the meanders). 5110, 5111, and 5112 are time series images of the mixer at the start, middle, and end of mixing by counter-clockwise rotation of the bearings. FIG. 51D is an image of the device after mixing lighter and darker dyes.

Rotary planar peristaltic micropump (RPPM) and rotary planar valve (RPV) technologies can also be combined into a well-plate assay controller. Since the same DC gear-head or stepping motor configuration can be used to drive both the RPPMs and the RPVs, the development on an integrated microfluidic control unit is attainable. The RPPMs and RPVs can be used in tandem to create general purpose instrumentation that can deliver, for example, within one minute a microliter of solution that is metered and mixed from multiple reservoirs whose relative contributions can be controlled on demand. The RPPMs can be used to drive the fluid through the systems and the RPVs will regulate flow to the desired inlet/outlets. Various reagent reservoirs for priming buffer, coating channels with desired matrix, cells, cell media, test sample and wash buffer will be considered to facilitate the implementation of assay protocols.

A typical well-plate assay with live cells can involve two modes. The first mode is a "preparation mode," which consists of priming the device, cell matrix injection, and cell injection followed by media injection until cells are confluent. A wash and suction step is integrated for waste removal. The second mode is an "assay mode," which refers to the test conditions where different samples (nutrients, xenobiotic compounds, drugs, and pathogens) are evaluated for their effects on the cells being cultured.

Figure 52A:
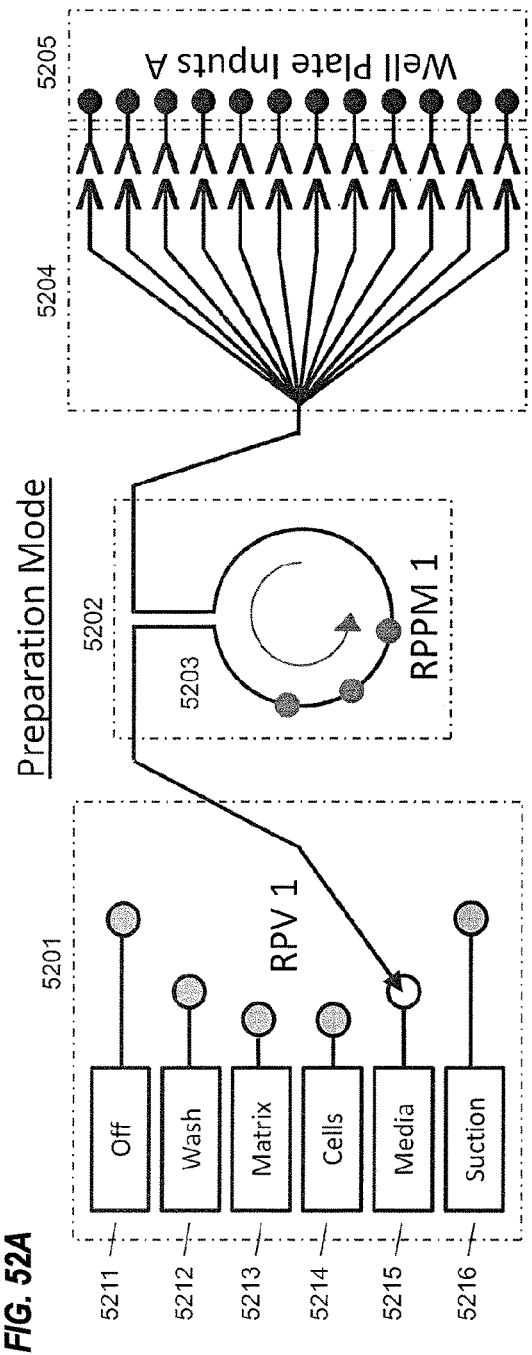
FIG. 52A shows schematically the Preparation Mode of a well-plate assay supported by an integrated RPPM-RPV device, according to one embodiment of the invention.

In this embodiment, each of these modes is supported by a separate RPPM-RPV device. FIG. 52A shows the device that supports the Preparation Mode. RPV 1 (5201) selects one of six inputs (5211-5216), RPPM 1 (5202) with rotating elements (5203) provides the pumping through the device, and a Y-channel or connector header (5204) provides the connection of the Preparation inputs to the input ports (5205) of the well plate, shown in FIG. 53. While 12 chambers are shown for convenience, the actual number could be different, either larger or smaller.

Figure 52B:
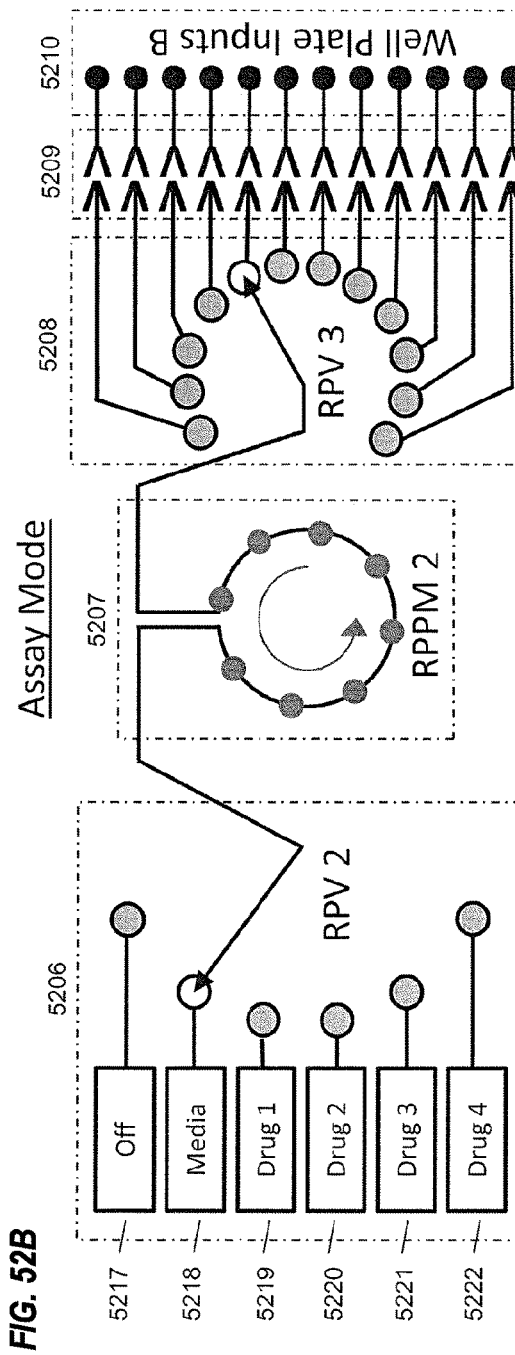
FIGS. 52B-52C show schematically alternative embodiments of the Assay Mode of the well plate of FIG. 52A.

The Assay Mode shown in FIG. 52B has RPV 2 (5206) that selects from six inputs (5217-5222), and the output of this valve goes to RPPM 2 (5207). The output of this pump then goes into a selector valve RPV 3 (5208), which determines which input fluid is injected through the connector 5209 and hence well-plate assay ports 5210 and then to the selected, individual chamber in the well plate.

Figure 52C:
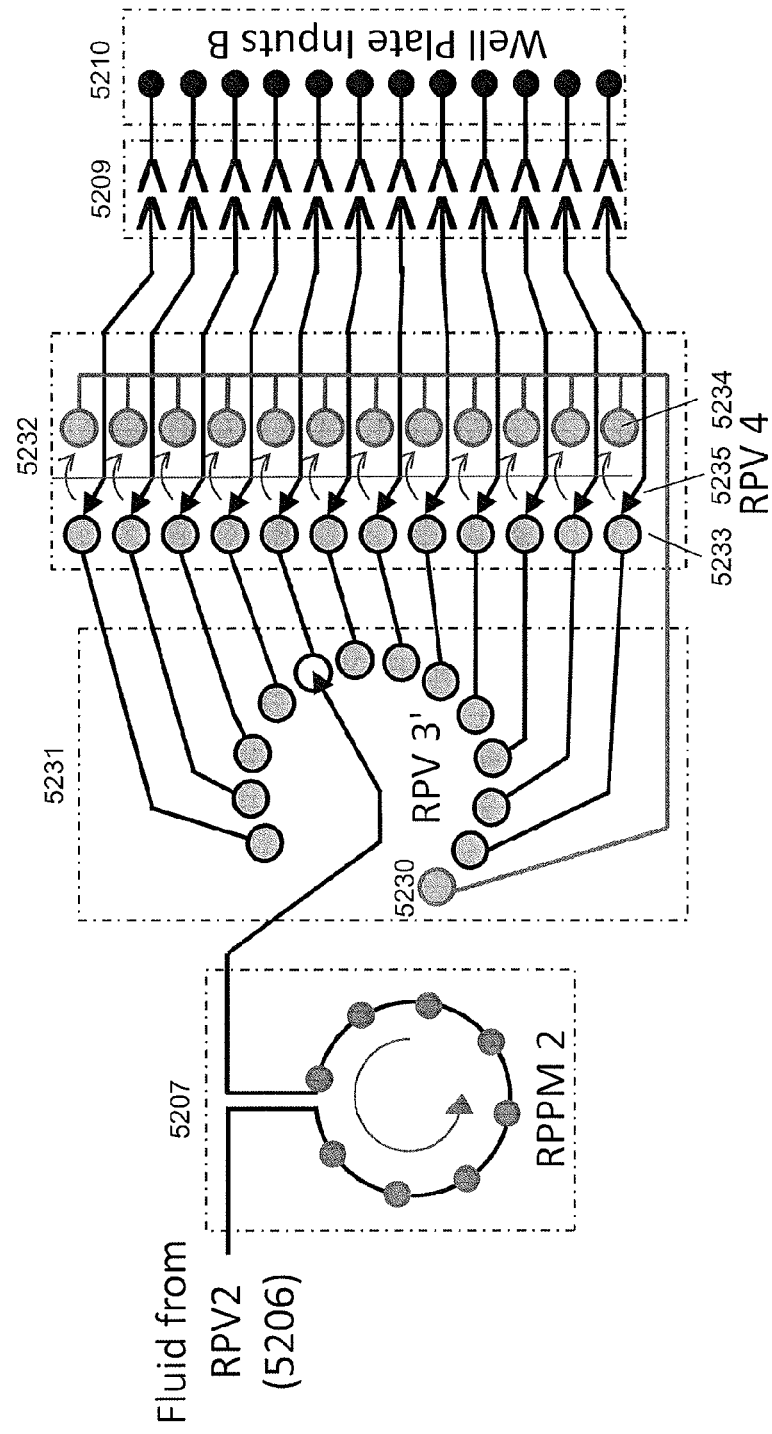

FIG. 52C shows an alternative embodiment for the Assay Mode, in which the output from RPPM 2 (5207) connects to RPV 3' that is similar to 5208 but with an additional valve position (5230) that is connected to a common set of ports (5234) in RPV 4 (5232). This 12-position RPV (5232) switches from random access to parallel flow for media flow, in a manner designed to eliminate crosstalk between the bioreactors until they are fed by the common line from the 13$^{th}$ position in RPV 3' (5231). For the serial loading of individual chambers in the well plate, as described in FIG. 52B, the selection of connections (5235) in RPV 4 (5232) connects each of the first 12 outputs of RPV 3' (5231) valve inputs (5233) to the corresponding well-plate connector and port in 5209 and 5210. In this embodiment, when RPV 4 is switched to the other position, the connections 5235 are made to the common ports (5234), and the output of RPPM 2 (5207) is directed in parallel to all twelve of the chambers through each line in 5209 and 5210. A particular advantage of this particular arrangement is that the 12 chambers in the well plate can be either addressed individually for loading, drug dosing, or analysis without cross contamination, or perfused in parallel to allow long-term culture without the need to use the RPVs actively to multiplex perfusion through all wells individually.

Figure 53:
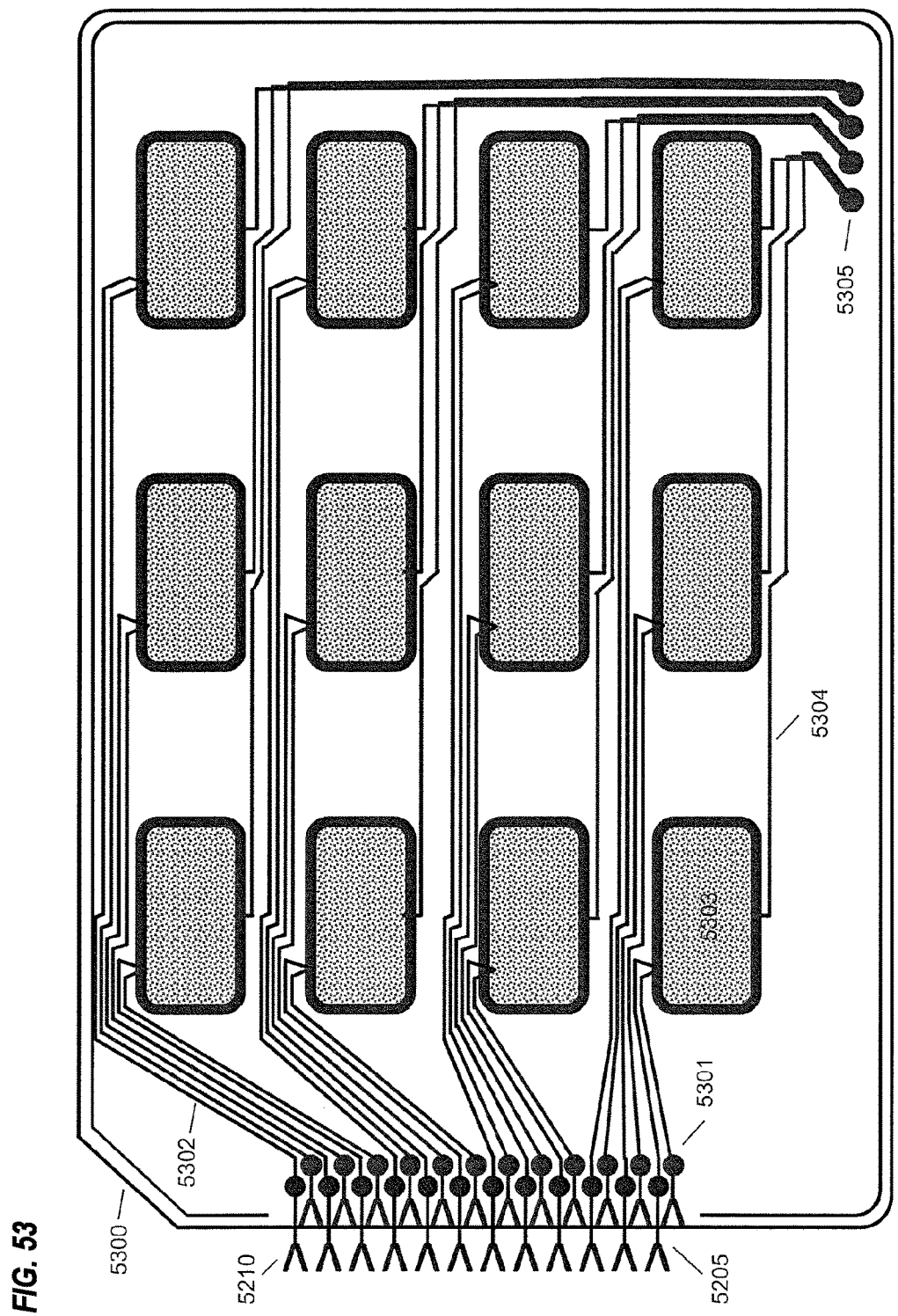
FIG. 53 shows schematically how the well-plate controllers of FIGS. 52A-52C could be connected to a 12-well plate, according to one embodiment of the invention.

The well-plate controllers in FIGS. 52A-C could be connected to the well plate in FIG. 53. The connector from the Preparation Mode controller (FIG. 52A) connects to the ports 5205, while those from the Assay Mode Controller (FIGS. 52B-C) connect to ports 5210. Each of these ports is connected to a perfusion line, for example, 5201 and 5202, respectively. The use of two separate lines reduces the possibility that cell debris or other materials from the loading process will interfere with the assay process and could be eliminated if desired. Each of the preparation and loading lines converges on an individual microfluidic chamber, device, or fluidic network, as shown for example by 5303. Each chamber, device, or network is connected to an individual drain line, e.g., 5304, and these lines are gathered together to form drain connections 5305 from the device. Other embodiments would be possible based upon this example.

The discussion below summarizes an automated well-plate loading and assay process, using the controller in FIG. 52 and the 12-well plate in FIG. 53 as an example. The process comprises the following sequences:

Preparation Mode

1. Stainless steel Y connectors into the inlet of each device with sealable plug to choose the port for injection in the 12 wells.

2. Four reservoirs for priming media, cell growth matrix, cells and cell culture media/harvesting media connected to a 6-position RPV for: Off, wash, matrix, cells, media, harvest.

3. An RPPM draws fluid from the valve and pressurizes the well plate for initiating the valve-based sequential operation.

4. A single tube goes to a disposable output connector with a built-in splitter for 12 Y-As. A blank termination tube goes to the 12 Y-Bs for use in the assay mode.

Assay Mode In this embodiment, we illustrate how to investigate the effects of four different drugs on a total of twelve separate cell populations.

1. Five reservoirs for media+four drug solution reservoirs.
2. Six-way RPV for Off, media, four drug solutions.
3. An RPPM interconnected to a 13-position RPV for individual well addressing or parallel addressing of all wells.
4. An RPV that can switch from serial individual loading to parallel, simultaneous perfusion.

Using the layout in FIG. 43, a set of six of motors that could be mounted in a manner to implement FIGS. 52A-C, with different microfluidic channels, to create a compact RPPM-RPV microfluidic control unit, which would thereby replace with a single unit all the hardware and tubing required by macroscopic laboratory implementations of microfluidic well-plate loading. Such a system would result in an integrated fluidic controller for a high-throughput assay. This system could then be utilized in standard microscopes, automated microscopes, high-throughput plate readers, and high-content screening automated microscopes, as well as being integrated into stand-alone instruments that contain the requisite optical and mechanical components.

One notable feature of this pump and valve system over other approaches is that a common motor and controller design can be used to control either a pump or a valve; the components are of sufficiently low cost that they can be implemented as individual support units for each well plate being assayed, and the devices are sufficiently compact that they could be placed inside a sterile, cell-culture incubator.

FIGS. 54A-D illustrate an embodiment of an RPPM device that maintains a constant flow rate without pulsatility. FIG. 54A depicts an RPPM with a U-shaped channel (5401) compressed by rotating bearings (5402) that pumps fluid from an inlet (5403) to an outlet (5404). FIG. 54B illustrates the mechanism by which pulsatility forms in such a device. As the bearing (5412) rotates and travels away from the fluid channel (5411), the area of the channel once compressed by 5412 is no longer compressed and expands to its normal height, thereby drawing in fluid to fill the expanding channel and temporarily reducing output flow. One method to eliminate this output pulse is to temporarily increase rolling element rotation speed as the event in FIG. 54B occurs, thus increasing output flow by an amount equal to the pulsed reduction in flow. FIG. 54C illustrates a second device, identical to FIG. 54A except for a channel modification (5431), designed to eliminate pulsatility while maintaining constant bearing rotation. FIG. 54D illustrates the function of the device, as rotating rolling elements (5441, 5444) compress a channel (5442) and pump fluid through 5442. As the last rolling element (5444) leaves the channel area, the previous rolling element (5441) compresses an expanded area of the channel (5443) and pumps an additional volume of fluid equal to the fluid lost through pulsatility.

While exemplary embodiments of the present invention have been shown and described in detail above, it will be clear to the person skilled in the art that changes and modifications may be made without departing from the scope of the invention. As such, that which is set forth in the preceding description and accompanying drawings is offered by way of illustration only and not as a limitation.

In addition, one of ordinary skill in the art will appreciate upon reading and understanding this disclosure that other variations for the invention described herein can be included within the scope of the present invention.

In the preceding Detailed Description of Disclosed Embodiments, various features are grouped together in several embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter lies in less than all features of a single disclosed embodiment. Thus, the following claims are hereby incorporated into the Detailed Description of Exemplary Embodiments, with each claim standing on its own as a separate embodiment.

REFERENCES

The following documents are incorporated herein by reference:

Chou, H. P., Unger, M. A., & Quake, S. R. A microfabricated rotary pump. Biomedical Microdevices 3, 323-330, (2001).

Darby, S. G., Moore, M. R., Friedlander, T. A., Schaffer, D. K., Reiserer, R. S., Wikswo, J. P., and Seale, K. T., A metering rotary nanopump for microfluidic systems. Lab on a Chip, 10, 3218-3226. (2010).

Du, M., Ye, X. Y., Wu, K. & Zhou, Z. Y. A peristaltic micro pump driven by a rotating motor with magnetically attracted steel balls. Sensors 9, 2611-2620, (2009).

Gu, W., Zhu, X. Y., Futai, N., Cho, B. S. & Takayama, S. Computerized microfluidic cell culture using elastomeric channels and Braille displays. Proceedings of the National Academy of Sciences of the United States of America 101, 15861-15866, (2004).

Hansen, C. L., Sommer, M. O. A., & Quake, S. R. Systematic investigation of protein phase behavior with a microfluidic formulator. Proceedings of the National Academy of the United States of America 101, 14431-14436, (2004).

Lim, K., Kim, S. & Hahn, J. H. Roller-type squeezing pump with picoliter handling capability. Sensors and Actuators B-Chemical 92, 208-214, (2003).

Takayama, S. et al. Integrated microfluidic control employing programmable tactile actuators. U.S. Ser. No. 07/745, 211 (2010). [0137] Yobas, L., Tang, K. C., Yong, S. E. & Ong, E. K. Z. A disposable planar peristaltic pump for lab-on-a-chip. Lab on a Chip 8, 660-662, (2008).

Oh, K W and Ahn, C H. A Review of Microvalves, J. Micromech. Microeng., 16, R13-R39 (2006).

Unger, M A, Chou, H P, Thorsen, T, Scherer, A, Quake, S R. Monolithic Microfabricated Valves and Pumps by Multilayer Soft Lithography, Science, 288, 113-116 (2000).

Melin, J and Quake, S R. Microfluidic Large-Scale Integration: The Evolution of Design Rules for Biological Automation, Annu. Rev. Biophys. Biomol. Struct., 36, 213-231 (2007).

Yobas, L, Tang, K C, Yong, S E, and Kye-Zheng Ong, E. A disposable planar peristaltic pump for lab-on-a-chip. Lab Chip, 8, 660-662 (2008).

What is claimed is:
1. A peristaltic micropump comprising:
one or more flexible channels configured to transfer one or more pumped fluids;
an actuator configured to engage the one or more flexible channels, and rotate about a central axis, wherein the actuator comprises at least one rolling element and a driving element configured such that the driving element operably rotates about the central axis and each rolling element operably rolls about a respective axis that is not parallel to the central axis; and the at least one rolling element is disposed between the one or more flexible channels and the driving element; and one or more valves, each of the one or more valves being coupled to a respective channel of the one or more flexible channels and being operably open so as to allow a fluidic flow to pass the valve, or closed so as to allow no fluidic flow to pass the valve, wherein one or more valves are configured to control flows of the one or more pumped fluids in the one or more flexible channels by selections of which valves are open or closed, wherein the one or more flexible channels contain at least a first fluid and a second fluid;

wherein the one or more valves are operably open or closed to control a flow rate of the first and second fluids during operation of the peristaltic micropump; and wherein the one or more flexible channels are in fluid communication such that the first and second fluids are operably mixed in varying proportions.

2. The peristaltic micropump of claim 1, wherein a first flexible channel of the one or more flexible channels comprises a bypass line configured to allow fluid to flow from an outlet of the first flexible channel to an inlet of the first flexible channel.

3. The peristaltic micropump of claim 1, wherein the one or more flexible channels are configured to provide sinusoidal or other output concentration waveforms.

* * * * *

UNITED STATES PATENT AND TRADEMARK OFFICE
CERTIFICATE OF CORRECTION

PATENT NO. : 10,487,819 B2
APPLICATION NO. : 15/820506
DATED : November 26, 2019
INVENTOR(S) : Parker A. Gould et al.

It is certified that error appears in the above-identified patent and that said Letters Patent is hereby corrected as shown below:

In the Specification

Column 1, Lines 15-18: should read as follows:
-- STATEMENT AS TO RIGHTS UNDER FEDERALLY-SPONSORED RESEARCH
This invention was made with government support under Grant No. DA028981, awarded by the National Institutes of Health and under Grant No. HDTRA1-09-1-0013 awarded by the Department of Defense. The Government has certain rights in the invention. --

Signed and Sealed this
Twenty-second Day of July, 2025

Coke Morgan Stewart
*Acting Director of the United States Patent and Trademark Office*